United States Patent
Allen et al.

(10) Patent No.: US 10,266,533 B2
(45) Date of Patent: Apr. 23, 2019

(54) 7-BENZYL-4-(2-METHYLBENZYL)-2,4,6,7,8,9-HEXAHYDROIMIDAZO[1,2-A]PYRIDO[3,4-E]PYRIMIDIN-5(1H)-ONE, ANALOGS THEREOF, AND SALTS THEREOF AND METHODS FOR THEIR USE IN THERAPY

(71) Applicants: ONCOCEUTICS, INC., Philadelphia, PA (US); PROVID PHARMACEUTICALS INC., Monmouth Junction, NJ (US)

(72) Inventors: Joshua E. Allen, New Haven, CT (US); Martin Stogniew, Blue Bell, PA (US); Richard S. Pottorf, Indianapolis, IN (US); Bhaskara Rao Nallaganchu, Hillsborough, NJ (US); Gary Olson, Mountainside, NJ (US); Yanjun Sun, Kendall Park, NJ (US)

(73) Assignee: Oncoceutics, Inc., Philadelphia, PA (US)

( * ) Notice: Subject to any disclaimer, the term of this patent is extended or adjusted under 35 U.S.C. 154(b) by 0 days.

(21) Appl. No.: 15/817,896

(22) Filed: Nov. 20, 2017

(65) Prior Publication Data
US 2018/0072729 A1    Mar. 15, 2018

Related U.S. Application Data

(60) Division of application No. 15/049,613, filed on Feb. 22, 2016, now Pat. No. 9,845,324, which is a continuation of application No. PCT/US2016/015817, filed on Jan. 29, 2016.

(60) Provisional application No. 62/109,737, filed on Jan. 30, 2015, provisional application No. 62/148,844, filed on Apr. 17, 2015, provisional application No. 62/233,757, filed on Sep. 28, 2015.

(51) Int. Cl.
| C07D 471/14 | (2006.01) |
| --- | --- |
| C07D 471/12 | (2006.01) |
| C07D 487/14 | (2006.01) |
| A61K 31/519 | (2006.01) |
| A61K 45/06 | (2006.01) |
| A61K 31/37 | (2006.01) |
| A61K 31/337 | (2006.01) |

(52) U.S. Cl.
CPC .......... *C07D 471/14* (2013.01); *A61K 31/337* (2013.01); *A61K 31/519* (2013.01); *A61K 45/06* (2013.01); *C07D 471/12* (2013.01); *C07D 487/14* (2013.01); *Y02A 50/387* (2018.01); *Y02A 50/463* (2018.01); *Y02A 50/467* (2018.01)

(58) Field of Classification Search
CPC .............. A61K 2300/00; A61K 31/337; A61K 31/519; A61K 45/06; C07D 471/12; C07D 471/14; C07D 487/14; Y02A 50/387; Y02A 50/463; Y02A 50/467
See application file for complete search history.

(56) References Cited

U.S. PATENT DOCUMENTS

| 4,642,345 A | 2/1987 | Temple, Jr. |
| --- | --- | --- |
| 4,783,450 A | 11/1988 | Fawzi et al. |
| 4,867,973 A | 9/1989 | Goers et al. |
| 6,869,958 B2 | 3/2005 | Li |
| 7,635,690 B2 | 12/2009 | Schinazi et al. |
| 8,673,923 B2 | 3/2014 | El-deiry et al. |
| 2004/0067953 A1 | 4/2004 | Stein et al. |
| 2007/0026402 A1 | 2/2007 | Noble et al. |
| 2007/0149571 A1 | 6/2007 | Stein et al. |
| 2008/0221135 A1 | 9/2008 | Voi |
| 2008/0254040 A1 | 10/2008 | Stefanic et al. |
| 2009/0022717 A1 | 1/2009 | Premack et al. |

(Continued)

FOREIGN PATENT DOCUMENTS

| DE | 2150062 A1 | 12/1973 |
| --- | --- | --- |
| WO | WO 2004/082570 A2 | 9/2004 |

(Continued)

OTHER PUBLICATIONS

Allen et al. "Dual Inactivation of Akt and ERK by TIC10 Signals Foxo3a Nuclear Translocation, TRAIL Gene Induction, and Potent Antitumor Effects", www.sciencetranslationmedicine.org vol. 5 Issue 171, 2013.

(Continued)

*Primary Examiner* — Erich A Leeser
(74) *Attorney, Agent, or Firm* — Pearl Cohen Zedek Latzer Baratz LLP

(57) ABSTRACT

This disclosure relates to methods of treatment using compound (1) or analogs thereof, and pharmaceutically acceptable salts thereof. Also disclosed are compounds of formula (10):

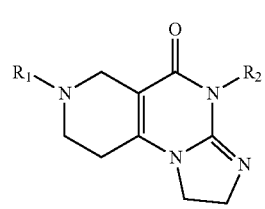

as defined in the specification, and pharmaceutically acceptable salts thereof, as well as pharmaceutical compositions comprising the same. Methods of treatment, such as for cancer, are provided that comprise administering the compounds and their salts to a subject in need of such treatment.

15 Claims, 6 Drawing Sheets

(56) References Cited

U.S. PATENT DOCUMENTS

| | | | |
|---|---|---|---|
| 2010/0266540 | A1 | 10/2010 | Craven |
| 2011/0287001 | A1 | 11/2011 | Holland et al. |
| 2012/0128732 | A1 | 5/2012 | Trieu et al. |
| 2012/0276088 | A1 | 11/2012 | El-Deiry et al. |
| 2013/0172314 | A1 | 7/2013 | Chen et al. |
| 2013/0209518 | A1 | 8/2013 | Desai et al. |
| 2014/0271540 | A1 | 9/2014 | Stogniew et al. |
| 2014/0335048 | A1 | 11/2014 | Stogniew et al. |
| 2015/0202206 | A1 | 7/2015 | El-deiry |
| 2017/0107221 | A1* | 4/2017 | Janda et al. ......... C07D 471/14 |
| 2018/0141946 | A1 | 5/2018 | Xu et al. |

FOREIGN PATENT DOCUMENTS

| | | |
|---|---|---|
| WO | WO 2011/144622 A1 | 11/2011 |
| WO | WO 2012/010704 A1 | 1/2012 |
| WO | WO 2012/149546 A2 | 11/2012 |
| WO | WO 2015/153468 A1 | 10/2015 |

OTHER PUBLICATIONS

Allen et al. "First-In-Class Small Molecule ONC201 Induces DR5 and Cell Death in Tumor but Not Normal Cells to Provide a Wide Therapeutic Index as an Anti-Cancer Agent" PLoS One. Nov. 18, 2015;10(11):e0143082.

Allen et al. "Identification of TRAIL-inducing compounds highlights small molecule ONC201/TIC10 as a unique anti-cancer agent that activates the TRAIL pathway" Mol Cancer. May 1, 2015;14:99.

Allen et al. "Genetic and Pharmacological Screens Converge in Identifying FLIP, BCL2, and IAP Proteins as Key Regulators of Sensitivity to the TRAIL-Inducing Anticancer Agent ONC201/TIC10" Cancer Res. Apr. 15, 2015;75(8):1668-74.

Allen et al. "The small molecule TIC10 has potent anticancer efficacy mediated by induction of TRAIL production in normal and tumor cells" Cancer Research, Apr. 15, 2011;71(8 Supplement):4502-.

Allen et al. "ONC201 Possesses a Benign Safety Profile at Highly Efficacious Doses in Normal Human Cells and Animal Toxicology Studies" Blood. Dec. 6, 2014;124(21):4812-; Abstract.

Allen et al. "ONC201 (TIC10) Induces TRAIL and Cell Death in Preclinical Models of Pediatric Lymphoma" Blood. Nov. 15, 2013;122(21):1671-; Abstract.

Allen et al. "Kinase library siRNA screen identifies KSR1 as a synergistic therapeutic target in combination with TIC10" Cancer Research. Apr. 15, 2013;73(8 Supplement):2059-; Abstract.

Allen et al. "Potent anti-tumor effects of TIC10 require Foxo3a and TRAIL gene upregulation" Cancer Research. Apr. 15, 2012;72(8 Supplement):1935-; Abstract.

Allen et al. "ONC201 Exhibits Mutation-Independent Efficacy with Superior Potency in Non-Hodgkin Lymphoma and Multiple Myeloma" Blood. Dec. 3, 2015;126(23):3873-.

Allen et al. "ONC201 is non-toxic at efficacious doses in vitro and in vivo" (2015): 4479-4479.

Baumeister et al. "Preclinical activity of new investigational drug ONC201 in triple-negative and non-triple negative and BRCA1-deficient breast cancer cells" (2016): e12564-e12564.

Baumeister et al. "ONC201 induces cell death in triple negative, BRCA1-deficient and non-triple negative breast cancer cells" (2016): 3012-3012.

Baumeister et al. "Novel small molecule ONC201 induces cell death and targets chemotherapy-resistant cancer stem-like cells in triple negative breast cancer" (2016): 3309-3309.

Duvic et al. "ONC201 Induces Apoptosis in Cutaneous T-Cell Lymphoma Cells through a Mechanism That Involves the Integrated Stress Response and Inactivation of Jak/Stat Signaling" Blood. Dec. 3, 2015;126(23):4011-.

Forfar et al. "Reaction between 5-(phenoxymethyl)-2-amino-2-oxazoline and N-benzyl-3-(ethoxycarbonyl)-4-piperidinone hydrochloride: A structural investigation" Tetrahedron, Oct. 29, 1999;55(44):12819-28.

Imperato GH, Allen JE, El-Deiry WS. Characterization of TIC10, a novel small molecule inducer of TRAIL, in combination with chemotherapy for lymphoma in vitro. Cancer Research. Apr. 15, 2013;73(8 Supplement):2949; Abstract.

International Search Report for PCT Application No. PCT/US16/15817 dated Jun. 20, 2016.

Ishizawa et al. "ATF4 induction through an atypical integrated stress response to ONC201 triggers p53-independent apoptosis in hematological malignancies" Sci Signal. Feb. 16, 2016;9(415):ra17.

Ishizawa et al. "ONC201 induces p53-independent apoptosis and cell cycle arrest in hematological malignancies and leukemic stem/progenitor cells by inducing ER stress and mTOR inhibition" Blood. Dec. 6, 2014;124(21):3122-; Abstract.

Ishizawa et al. "ONC201 Induces p53-Independent Apoptosis and Abrogates Stem Cell Function, in Hematological Malignancies by Induction of ATF4 through Integrated Stress Response" Blood. Dec. 3, 2015;126(23):2051-.

Jacob et al. "Pharmacophore reassignment for induction of the immunosurveillance cytokine TRAIL", Angew Chem Int Ed Engl. Jun. 23, 2014;53(26):6628-31.

Karpel-Massler et al. "TIC10/ONC201 synergizes with Bcl-2/Bcl-xL inhibition in glioblastoma by suppression of Mcl-1 and its binding partners in vitro and in vivo" Oncotarget. Nov. 3, 2015;6(34):36456-71.

Khan et al. "ABT199 and ONC201 in Diffuse Large B Cell Lymphoma Cell Lines" Blood. Dec. 3, 2015;126(23):5129-.

Kline et al. "ONC201 kills solid tumor cells by triggering an integrated stress response dependent on ATF4 activation by specific eIF2α kinases" Sci. Signal . . . Feb. 16, 2016:9(415):ra18-.

Kline et al. "ONC201 anti-cancer effects against solid tumors are mediated through eIF2α kinases HRI and PKR but are PERK-independent" (2016): 3014-3014.

Kline et al. "Early integrated stress response induction of ATF4 is required for the anticancer effects of the dual Akt/ERK inhibitor and TRAIL pathway inducer ONC201/TIC10." (2015): 674-674.

Kline et al. "TRAIL pathway inducer ONC201/TOC10 primes multiple myeloma cells (MM) for apoptosis by downreguiating X-linked inhibitor of apoptosis" (2015): 2942-2942.

Kojima et al. "ONC201 Exerts p53-Independent Cytotoxicity Through TRAIL and DR5 Induction in Mantle Cell Lymphomas" Blood. Nov. 15, 2013;122(21):3822-; Abstract.

Lee et al. "First-in-class small molecule ONC201 in b-cell malignancies" (2016): TPS7581-TPS7581.

Lev et al. "Preclinical efficacy of new investigational drug ONC201 and analogs ONC212 and ONC206 against patient-derived pancreatic cancer cell lines" (2016): e15752-e15752.

Lev et al. "ONC201 induces cell death in androgen receptor positive prostate cancer cells and shows synergistic effect with anti-prostate cancer drugs" (2016): 1825-1825.

Lev et al. "ONC212 exhibits increased cytotoxicity relative to ONC201 in a subset of human pancreatic cancer cell lines" (2016): 4826-4826.

Lulla et al. "Caspase-Dependent Anti-Tumor Effects of ONC201/TIC10 on Acute Myeloid Leukemia (AML) and Multiple Myeloma (MM)" Blood. Dec. 6, 2014;124(21):5224-; Abstract.

Madhukar et al. "Abstract LB-209: D2-like dopamine receptor antagonism by ONC201 identified by confluence of computational, receptor binding, and clinical studies" (2016): LB-209.

Prabhu et al. "Small-Molecule ONC201/TIC10 Targets Chemotherapy-Resistant Colorectal Cancer Stem-like Cells in an Akt/Foxo3a/TRAIL-Dependent Manner" Cancer Res. Apr. 1, 2015;75(7):1423-32; Abstract.

Prabhu et al. "ONC201 Depletes Cancer Stem Cells in Refractory Cancer Patient Samples" Blood. Dec. 6, 2014;124(21):5219-; Abstract.

Prabhu et al. "Small Molecule ONC201,TIC10 Induces Caspase-Dependent Apoptosis in Acute Lymphoblastic Leukemia Cells Via Modulation of Bcl-2 and IAP Family Proteins" Blood. Dec. 6, 2014;124(21):5237-; Abstract.

Prabhu et al, "Therapeutic targeting of colorectal cancer stem cells by TRAIL-inducing small molecule TIC10" Cancer Research. Apr. 15, 2013;73(8 Supplement):3732; Abstract.

(56) References Cited

OTHER PUBLICATIONS

Prabhu et al. "ONC201 targets cancer stem cells in colorectal, prostate and glioblastoma multiforme tumors via modulation of stem cell-related gene expression" (2016); 2497-2497.
Prabhu et al. "ONC201/TIC10 targets colorectal cancer stem cells and bulk tumor cells via an Akt-Foxo3a-TRAIL-dependent mechanism" (2015): 4241-4241.
Pubchem SureCN2018352, CID 5486859, pp. 1-3, Create Date: Aug. 9, 2005; p. 1; [retrieved on Sep. 19, 2014]. Retrieved from the Internet: <URL: https://pubchem.ncbi.nlm.nih.gov/summary/summary.cgi?cid=5486859&loc=ec_rcs>.
Pubchem CID 73777259, pp. 1-3, Create Date: May 26, 2014; p. 1; [retrieved on Sep. 19, 2014]. Retrieved from the Internet: <URL: https://pubchem.ncbi.nlm.nih.gov/summary/summary.cgi?cid=737772598(loc=ec_rcs>.
Stein et al. "first-in-human trial of onc201 in patients with refractory solid tumors" (2016): 2514-2514.
Stein et al. "Clinical activity of ONC201 in metastatic castrate resistant prostate cancer (mCRPC)" (2016): e16514-e16514.
Stein et al. "First-in-human dose escalation study of oral ONC201 in advanced solid tumors." (2015): TPS2623-TPS2623.
Talekar et al. "ONC201 induces cell death in pediatric non-Hodgkin's lymphoma cells" Cell Cycle. Aug. 3, 2015;14(15):2422-8.
Talekar et al. "ONC201/TIC10 Is Effective As a Monoagent and Synergizes with Chemotherapy to Induce Cell Death in Non-Hodgkin Lymphoma" Blood. Dec. 6, 2014;124(21):5491-; Abstract.
Talekar et al. "TRAIL-inducing agent-TIC10 and combinatorial therapeutics in pediatric lymphoma: a targeted approach" Abstract LB-307, Cancer Research. Apr. 15, 2013;73(8 Supplement):LB-307; Abstract.
Tarapore et al. "ONC201 sensitivity profiling indicates pronounced sensitivity in lymphoid, prostate, colon and brain tumors" (2016): 1236-1236.
Wagner et al., "The angular structure of ONC201, a TRAIL pathway-inducing compound, determines its potent anti-cancer activity", Oncotarget vol. 5, No. 24, Jan. 2015.
Wagner et al. "Screen of Small Molecule ONC201/TIC10 Identifies Single Agent Activity and Combinatorial Efficacy with Bortezomib, Rituximab or Dexamethasone in Killing of Acute Lymphoblastic Leukemia Cells" Blood. Dec. 6, 2014;124(21):5233-; Abstract.
Wagner et al. "Dose-intensified ONC201 to exert anti-metastatic efficacy and to promote intra-tumoral recruitment of NK-cells in mice" (2016): 11550-11550.
Wagner et al. "Combination of ONC201 and bevacizumab significantly impacts colorectal cancer growth and metastasis in vivo" (2016): 3087-3087.
Wagner et al. "Structure-activity relationships (SAR) and mechanistic analysis of clinical-stage anti-cancer small molecule ONC201 analogues" (2016): e23161-e23161.

Wagner et al. "Intra-tumoral accumulation of NK1. 1/CD3+ cells and anti-metastasis effects of dose-intensified ONC201 in tumor-bearing mice" (2016): 3000-3000.
Wagner et al. "Cytotoxicity, biochemical activity, and structural analysis of ONC201 and comparisons to a biologically inactive isomer." (2015): 4499-4499.
Zhang et al. "The preclinical evaluation of TIC10/ONC201 as an anti-pancreatic cancer agent" Biochem Biophys Res Commun. Aug. 5, 2016;476(4):260-6.
Zhao et al. "ONC201, a small molecule Foxo3a activator, activity against patient-derived glioblastoma tumor-initiating cells" In ASCO Annual Meeting Proceedings May 20, 2014 (vol. 32, No. 15_suppl, p. e13022).
Aihara, et al. "H3F3A K27M mutations in thalamic gliomas from young adult patients" Neuro-oncology. Nov. 26, 2013;16(1):140-6.
Fowler et al. "Receptor conformations involved in dopamine D2L receptor functional selectivity induced by selected transmembrane 5 serine mutations" Molecular pharmacology. Jan. 1, 2012:mol-111.
Jully et al. "Potential molecular targets for Ewing's sarcoma therapy" Indian journal of medical and paediatric oncology: official journal of Indian Society of Medical & Paediatric Oncology. Oct. 2012;33(4):195.
Laburthe et al. "The orexin receptor OX1R in colon cancer: a promising therapeutic target and a new paradigm in G protein-coupled receptor signalling through ITIMs" British journal of pharmacology. Mar. 1, 2012;165(6):1678-87.
Li et al. "Genome-wide shRNA, screen revealed integrated mitogenic signaiing between dopamine receptor D2 (DRD2) and epidermal growth factor receptor (EGFR) in glioblastoma" Oncotarget. Feb. 2014;5(4):882.
Lutz et al. "Opioid receptors: distinct roles in mood disorders" Trends in neurosciences. Mar. 1, 2013;36(3)195-206.
Pollard TD. "A guide to simple and informative binding assays" Molecular biology of the cell. Dec. 1, 2010;21(23):4061-7.
Soares et al. "Role of the platelet-activating factor (PAF) receptor during pulmonary infection with gram negative bacteria" British journal of pharmacology. Nov. 1, 2002;137(5):621-8.
Soejima et al. "Epigenetic silencing of the MGMT gene in cancer" Biochemistry and cell biology. Aug. 1, 2005;83(4):429-37.
Supplemental Partial European Search Report for European Application No. 16744237.5 dated May 28, 2018.
Supplemental European Search Report for European Application No. 16744237.5 dated Aug. 31, 2018.
Yung et al "Host chemokines bind to *Staphylococcus aureus* and stimulate protein a release" Journal of Biological Chemistry. Feb. 18, 2011;286(7):5069-77.
Zhao et al. "p53 loss promotes acute myeloid leukemia by enabling aberrant self-renewal" Genes & development. Jul. 1, 2010;24(13):1389-402.

\* cited by examiner

7-BENZYL-4-(2-METHYLBENZYL)-2,4,6,7,8,9-HEXAHYDROIMIDAZO[1,2-A]PYRIDO[3,4-E]PYRIMIDIN-5(1H)-ONE, ANALOGS THEREOF, AND SALTS THEREOF AND METHODS FOR THEIR USE IN THERAPY

CROSS REFERENCE TO RELATED APPLICATIONS

This application is a divisional application of U.S. application Ser. No. 15/049,613, filed Feb. 22, 2016, which is a continuation application of PCT Application Number PCT/US16/15817, filed Jan. 29, 2016, which claims the benefit of U.S. Provisional Application No. 62/109,737, filed Jan. 30, 2015, and which claims the benefit of U.S. Provisional Application No. 62/148,844, filed Apr. 17, 2015, and which claims the benefit of U.S. Provisional Application No. 62/233,757, filed Sep. 28, 2016, all of which are incorporated by reference therein in their entirety.

BACKGROUND OF THE INVENTION

TNF-related apoptosis-inducing ligand (TRAIL; Apo2L) is an endogenous protein that selectively induces apoptosis in cancer cells. TRAIL is a powerful inducer of apoptosis in a wide range of human cancer cell lines via pro-apoptotic death receptor 4 (DR4; TRAIL-R1) and death receptor 5 (DR5; TRAIL-R2) at the cell surface through engagement of the extrinsic or intrinsic apoptotic pathways. TRAIL plays a direct role in tumor suppression during immune surveillance but this anti-tumor mechanism is lost during the disease progression. The ability of TRAIL to initiate apoptosis selectively in cancer cells has led to ongoing clinical trials with administration of recombinant TRAIL and the longer-lived TRAIL-agonist antibodies targeting either of its two pro-apoptotic death receptors.

Despite its potency, recombinant TRAIL has efficacy-limiting properties such as short serum half-life, stability, cost, and delivery. Delivery of recombinant TRAIL or TRAIL-agonist antibodies to the brain is limited by inability of recombinant TRAIL and TRAIL-agonist antibodies to cross the blood-brain barrier. Accordingly, there is a continuing need for anti-cancer compositions and methods.

BRIEF SUMMARY OF THE INVENTION

In one aspect, provided herein are compounds of formula (10):

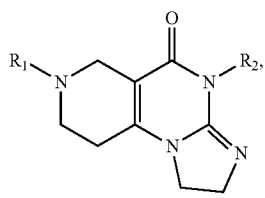

(10)

wherein $R_1$ and $R_2$ independently represent hydrogen, alkyl, cycloalkyl, cycloalkylalkyl, heterocycloalkyl, heterocycloalkylalkyl, aryl, heteroaryl, arylalkyl, heteroarylalkyl, alkoxyalkyl, alkoxycarbonyl, aralkoxy, aralkylthio, and acyl, radicals, wherein when $R_1$ represents $CH_2Ph$, $R_2$ does not represent $CH_2$-((2-$CH_3$)-Ph). In some embodiments, $R_1$ and $R_2$ are independently selected from the group consisting of H, $C_{1-4}$alkyl, $C_{1-4}$alkylphenyl, $C_{1-4}$alkylphenylketone, $C_{1-4}$benzyl-piperazine, $C_{1-4}$alkylthienyl, $C_{1-4}$alkylpyridinyl, $C_{1-4}$alkylisoxazolidinyl, $C_{1-4}$alkylmorpholinyl, $C_{1-4}$alkylthiazolyl, and $C_{1-4}$alkylpyrazinyl wherein $C_{1-4}$alkyl, $C_{1-4}$alkylphenyl, $C_{1-4}$alkylphenylketone, $C_{1-4}$benzyl-piperazine, $C_{1-4}$alkylthienyl, $C_{1-4}$alkylpyridinyl, $C_{1-4}$alkylisoxazolidinyl, $C_{1-4}$alkylmorpholinyl, $C_{1-4}$alkylthiazolyl, and $C_{1-4}$alkylpyrazinyl are optionally substituted with $C_{1-4}$alkyl, $C_{1-4}$alkoxyl, hydroxyl, perhalogenated $C_{1-4}$alkyl, or halo. In some embodiments, $R_1$ and/or $R_2$ is a substituted or unsubstituted, arylalkyl or heteroarylalkyl. In some embodiments, the heteroarylalkyl is selected from $C_{1-4}$alkylpyrrolyl, $C_{1-4}$alkylfuryl, $C_{1-4}$alkylpyridyl, $C_{1-4}$alkyl-1,2,4-thiadiazolyl, $C_{1-4}$alkylpyrimidyl, $C_{1-4}$alkylthienyl, $C_{1-4}$alkylisothiazolyl, $C_{1-4}$alkylimidazolyl, $C_{1-4}$alkyltetrazolyl, $C_{1-4}$alkylpyrazinyl, $C_{1-4}$alkylpyrimidyl, $C_{1-4}$alkylquinolyl, $C_{1-4}$alkylisoquinolyl, $C_{1-4}$alkylthiophenyl, $C_{1-4}$alkylbenzothienyl, $C_{1-4}$alkylisobenzofuryl, $C_{1-4}$alkylpyrazolyl, $C_{1-4}$alkylindolyl, $C_{1-4}$alkylpurinyl, $C_{1-4}$alkylcarbazolyl, $C_{1-4}$alkylbenzimidazolyl, and $C_{1-4}$alkylisoxazolyl. In some embodiments, $R_1$ and/or $R_2$ is a substituted or unsubstituted, benzyl or phenylethyl. In some embodiments, $R_1$ and/or $R_2$ is a benzyl optionally substituted with one or more of the following substituents on the benzyl ring: X, —$CH_3$, —$NO_2$, —$OCH_3$, —CN, —$CXH_2$, —$CX_2H$, $C_2$-$C_4$ alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR'''$, $SR'''$, $NR'''R''$, $NR'''C(O)R''$, $SOR'''$, $SO_2R'''$, $C(O)R'''$, and $C(O)OR'''$;

$R'''$ and $R''$ are independently selected from hydrogen or a $C_1$-$C_4$ alkyl;

where p is an integer from 2 to 20 and X represents a halogen.

In one embodiment, compound (10) has the structure of compound (90)

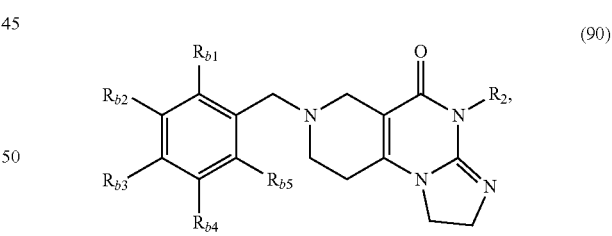

(90)

wherein $R_2$ is as defined above, and wherein $R_{b1}$, $R_{b2}$, $R_{b3}$, $R_{b4}$, and $R_{b5}$ are each independently selected from the group consisting of hydrogen, X, —$CH_3$, —$NO_2$, —$OCH_3$, —CN, —$CXH_2$, —$CX_2H$, $C_2$-$C_4$ alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR'''$, $SR'''$, $NR'''R''$, $NR'''C(O)R''$, $SOR'''$, $SO_2R'''$, $C(O)R'''$, and $C(O)OR'''$;

$R'''$ and $R''$ are independently selected from hydrogen or a $C_1$-$C_4$ alkyl;

where p is an integer from 2 to 20 and X represents a halogen.

In one embodiment, compound (10) has the structure of compound (40)

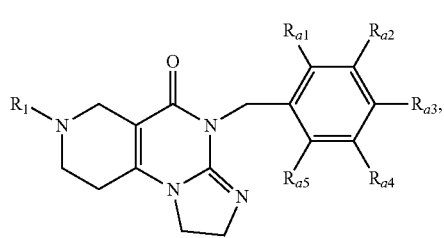

(40)

wherein $R_1$ is as defined above, and wherein $R_{a1}$, $R_{a2}$, $R_{a3}$, $R_{a4}$, and $R_{a5}$ are each independently selected from the group consisting of hydrogen, X, —$CH_3$, —$NO_2$, —$OCH_3$, —CN, —$CXH_2$, —$CX_2H$, $C_2$-$C_4$ alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR'''$, $SR'''$, $NR'''R''$, $NR'''C(O)R''$, $SOR'''$, $SO_2R'''$, $C(O)R'''$, and $C(O)OR'''$;

$R'''$ and $R''$ are independently selected from hydrogen or a $C_1$-$C_4$ alkyl;

where p is an integer from 2 to 20 and X represents a halogen.

In one embodiment, compound (10) has the structure of compound (50):

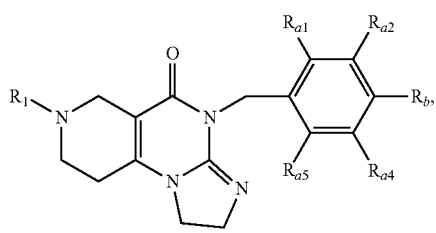

(50)

wherein $R_1$ is as defined above, and wherein $R_b$ is selected from the group consisting of X, —$CH_3$, —$NO_2$, —$OCH_3$, —CN, —$CXH_2$, —$CX_2H$, $C_2$-$C_4$ alkyl, —$CX_3$, —$CH_2$ $(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR'''$, $SR'''$, $NR'''R''$, $NR'''C(O)R''$, $SOR'''$, $SO_2R'''$, $C(O)R'''$, and $C(O)OR'''$; and where $R_{a1}$, $R_{a2}$, $R_{a4}$, and $R_{a5}$ are each independently selected from the group consisting of hydrogen, X, —$CH_3$, —$NO_2$, —$OCH_3$, —CN, —$CXH_2$, —$CX_2H$, $C_2$-$C_4$ alkyl, —$CX_3$, —$CH_2$ $(CX_3)$, —$CH(CX_3)_2$, —$C(CX_3)_3$, —$CX_pX_{2p+1}$, —$OCX_3$, —$OC_pH_{2p+1}$, —$OC_pX_{2p+1}$, $OR'''$, $SR'''$, $NR'''R''$, $NR'''C(O)R''$, $SOR'''$, $SO^2R'''$, $C(O)R'''$, and $C(O)OR'''$;

$R'''$ and $R''$ are independently selected from hydrogen or a $C_1$-$C_4$ alkyl;

where p is an integer from 2 to 20 and X represents a halogen.

In one embodiment, compound (10) has the structure of compound (80)

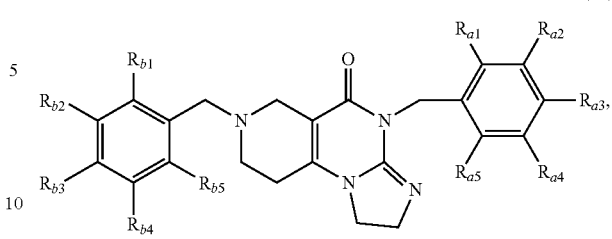

(80)

wherein $R_{a1}$, $R_{a2}$, $R_{a3}$, $R_{a4}$, $R_{a5}$, $R_{b1}$, $R_{b2}$, $R_{b3}$, $R_{b4}$, and $R_{b5}$ are each independently selected from the group consisting of hydrogen, X, —$CH_3$, —$NO_2$, —$OCH_3$, —CN, —$CXH_2$, —$CX_2H$, $C_2$-$C_4$ alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR'''$, $SR'''$, $NR'''R''$, $NR'''C(O)R''$, $SOR'''$, $SO_2R'''$, $C(O)R'''$, and $C(O)OR'''$;

$R'''$ and $R''$ are independently selected from hydrogen or a $C_1$-$C_4$ alkyl;

where p is an integer from 2 to 20 and X represents a halogen.

In another aspect, the present invention provides a pharmaceutical composition, comprising a compound of formula (10) or a pharmaceutically acceptable salt thereof. In one embodiment, the pharmaceutical composition comprises pharmaceutically acceptable salt of a compound of formula (10). In one embodiment, the salt is a pharmaceutically acceptable mono-salt of a compound of formula (10). In one embodiment, the salt is a pharmaceutically acceptable di-salt of a compound of formula (10). In one embodiment, the pharmaceutically acceptable salt is selected from the group consisting of hydrochloride, hydrobromide, hydrogensulphate, sulfates, phosphates, fumarates, succinates, oxalates and lactates, bisulfates, hydroxyl, tartrate, nitrate, citrate, bitartrate, carbonate, malate, maleate, fumarate sulfonate, methylsulfonate, formate, acetate, and carboxylate. In one embodiment, the pharmaceutically acceptable salt is selected from the group consisting of p-toluene-sulfonate, benzenesulfonate, methanesulfonate, oxalate, succinate, tartrate, citrate, fumarate, glucuronate, ascorbate and maleate. In one embodiment, the pharmaceutically acceptable salt is selected from ammonium, sodium, potassium, calcium, magnesium, zinc, lithium, and/or with other counter-ions such as methylamino, dimethylamino, diethylamino and triethylamino counter-ions. In one embodiment, the pharmaceutical composition comprises a hydrochloride di-salt or hydrobromide di-salt of a compound of formula (10). In some embodiments, a pharmaceutical composition of the present invention includes a pharmaceutically acceptable carrier.

In some embodiments, a pharmaceutical composition o the present invention includes a second therapeutic agent. In one embodiment, the second therapeutic agent is an anti-cancer agent. In one embodiment, the anti-cancer agent is a mitotic inhibitor. In one embodiment, the anti-cancer agent is selected from the group consisting of: paclitaxel, docetaxel and a combination thereof. In an alternative embodiment, the second therapeutic agent is an anti-angiogenic agent. In one embodiment, the anti-angiogenic agent is bevacizumab. In one embodiment, the second therapeutic agent is administered as part of combination therapy to treat a patient. In one embodiment, details for the combination therapy is included in a package insert for the compound of formula (10).

In some embodiments, the pharmaceutical composition is formulated for oral administration.

In another aspect, the present invention provides methods of treatment. In one embodiment, the method of treatment comprises administering to a subject a pharmaceutical composition, the pharmaceutical composition comprising a pharmaceutically effective amount of a compound of formula (10) or a pharmaceutically acceptable salt thereof.

In one embodiment, the method of treatment comprises administering to the subject a pharmaceutical composition comprising a pharmaceutically effective amount of a compound of formula (10) or a pharmaceutically acceptable salt thereof. In one embodiment, the method of treatment comprises administering to the subject a pharmaceutical composition comprising a pharmaceutically effective amount of a compound of formula (10) or a pharmaceutically acceptable salt thereof and a pharmaceutically acceptable carrier.

In some embodiments, the method of treatment further comprises administering an additional therapeutic agent. In one embodiment, the additional therapeutic agent includes an anti-cancer agent. In one embodiment, the additional anti-cancer agent comprises an anti-mitotic agent. In one embodiment, the additional anti-cancer agent comprises paclitaxel, docetaxel, bevacizumab or a combination thereof.

In one embodiment, the method of treatment further comprises assaying tumor necrosis factor (TNF)-related apoptosis-inducing ligand (TRAIL) in a sample obtained from the subject undergoing treatment. In one embodiment, the sample is a blood sample.

In one embodiment of the method of treatment, the subject undergoing treatment has, or is at risk of having, cancer. In one embodiment, the cancer is selected from the group consisting of colon cancer, breast cancer, glioblastoma multiforme, Mantle cell lymphoma, and colorectal cancer. In one embodiment, the cancer is selected from the group consisting of actinic keratosis, Barrett's esophagus, atrophic gastritis, dyskeratosis congenital, sideropenic dysphagia, lichen planus, oral submucous fibrosis, solar elastosis, cervical dysplasia, leukoplakia, and erythroplakia.

In one embodiment of the method of treatment, the pharmaceutical composition is administered via an oral administration route. In one embodiment, the pharmaceutical composition is administered via an administration route selected from the group consisting of: intravenous, rectal, nasal, pulmonary, epidural, ocular, otic, intra-arterial, topical, intracardiac, intracerebroventricular, intradermal, intramuscular, intraperitoneal, intraosseous, intrathecal, intravesical, subcutaneous, transdermal, transmucosal, sublingual, buccal, vaginal, and inhalational routes of administration.

In one embodiment, the present invention provides a method of treating a subject having, or is at risk of having, brain cancer, the method comprising: administering to the subject a pharmaceutical composition comprising a pharmaceutically effective amount a compound of formula (10) or a pharmaceutically acceptable salt thereof. In one embodiment, the pharmaceutical composition comprises a pharmaceutically acceptable carrier.

In one embodiment, the present invention provides a method of treatment comprising administering to a subject a pharmaceutical composition, the pharmaceutical composition comprising a pharmaceutically effective amount of a compound of formula (10) or a pharmaceutically acceptable salt thereof; and a pharmaceutically acceptable carrier.

In another aspect, the present invention provides a method of treating a subject in need of such treatment, the method comprising:

(i) administering to the subject q first therapeutic agent including a compound of formula (10) or a pharmaceutically acceptable salt thereof;

(ii) waiting until a predetermined waiting time has elapsed after the time of administration of the first therapeutic agent to the subject; and (iii) administering a second therapeutic agent to the subject, wherein the predetermined waiting time is chosen so as to obtain a delayed therapeutic effect of the first therapeutic agent without an increased risk or with a reduced risk of possible combined toxic effects of the first and second therapeutic agents.

In another aspect, the present invention provides a method of treating a subject in need of such treatment, the method comprising:

(i) administering to the subject a first therapeutic agent including a compound of formula (10) or a pharmaceutically acceptable salt thereof;

(ii) monitoring the level of the compound of formula (10) or a salt thereof or a metabolite thereof in the subject using pharmacokinetic profiling; and (iii) administering a second therapeutic agent conditional on the level of the first therapeutic agent in the subject.

In another aspect, the present invention provides a method of, the method comprising:

(i) administering to the subject a first therapeutic agent including a compound of formula (10) or a pharmaceutically acceptable salt thereof; and (ii) administering a second therapeutic agent conditional on the expected half life of the compound of formula (10) in the subject undergoing treatment.

In another aspect, provided herein are analogs of compounds of formula (10):

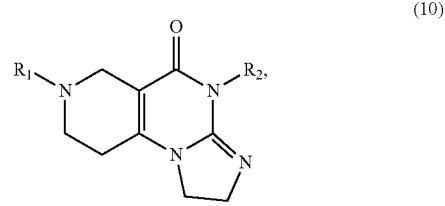

(10)

or of formula (1):

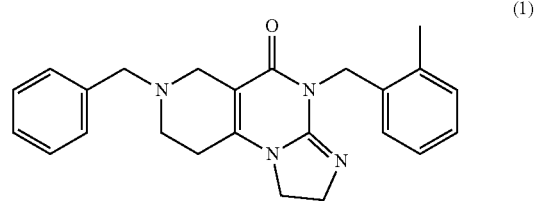 [SMILES: Cc1ccccc1CN1C(=O)C2=C(CCN(Cc3ccccc3)C2)N2CCN=C12]

(1)

and their pharmaceutically acceptable salts, as well as processes of making the same. In one aspect, provided herein are methods of treatment. In one embodiment, the treatment method comprises administering to a subject a pharmaceutical composition, the composition comprising a pharmaceutically effective amount of a compound of formula (10) or of formula (1) or an analog thereof, or a pharmaceutically acceptable salt thereof. In one embodiment, the pharmaceutical composition includes a a pharmaceutically acceptable carrier. In one embodiment, the subject undergoing treatment has, or is at risk of having, cancer. In one embodiment, the subject is a human.

In another aspect, the present invention provides a method of treating a subject in need of such treatment, the method comprising:

(i) administering to the subject a first therapeutic agent including an analog of compound (1) (e.g., a compound of formula (10)) or a pharmaceutically acceptable salt thereof; and (ii) administering a second therapeutic agent conditional on adverse events from the first therapeutic agent having resolved or are resolving. In some embodiments, adverse events from the first therapeutic agent are related to the blood levels of that agent or metabolites thereof in the subject undergoing treatment.

In another aspect, the present invention provides a kit for monitoring of an analog of compound (1) (e.g., a compound of formula (10)) or a pharmaceutically acceptable salt thereof or a metabolite thereof in an individual treated with the analog of compound (1) or pharmaceutically acceptable salt thereof or metabolite thereof using pharmacokinetic profiling, the kit comprising a plurality of point-of-care devices or point of use devices capable of quantitating the drug in at least two samples or matrices suitable for storage of those samples prior to quantitation by a laboratory. In some embodiments, a kit further comprising instructions for collecting and/or storing the at least two samples.

In some embodiments, the treatment method comprises administering to a subject a pharmaceutical composition, the pharmaceutical composition comprising a pharmaceutically effective amount of a compound of formula (1) or of formula (10), an analog thereof, or a pharmaceutically acceptable salt thereof; and (ii) monitoring levels of the compound or a pharmaceutically acceptable salt thereof, or a metabolite thereof in the subject using pharmacokinetic profiling, wherein dosing of the compound or salt thereof is selected to maintain a concentration of the compound or a metabolite thereof in whole blood, plasma, serum, or cerebrospinal fluid of the subject of at least about 400 ng/mL for a therapeutic time period within 4 hours post-treatment. In some embodiments, the subject undergoing treatment has, or is at risk of having, cancer. In some embodiments, the treatment method further comprises the step of waiting for a predetermined waiting time (e.g., the waiting time is the same length as the first time interval) between one or more repetitions of step (i). In some embodiments, the subject is a human.

In some embodiments, the treatment method comprises administering to a subject a pharmaceutical composition, the pharmaceutical composition comprising a pharmaceutically effective amount of a compound of formula (1) or of formula (10), an analog thereof, or a pharmaceutically acceptable salt thereof; and (ii) monitoring levels of the compound or a metabolite thereof in the subject using pharmacokinetic profiling, wherein dosing of the compound or salt thereof is selected to obtain an AUC of the compound or a metabolite thereof in whole blood, plasma, serum, or cerebrospinal fluid of the subject of at least about 3,500 hr-ng/mL with a time period of 2, 6, 12, 24, 48, 72 or greater than 72 hours post-treatment or extrapolated to infinity.

In some embodiments, the treatment method comprises administering to a subject a pharmaceutical composition, the pharmaceutical composition comprising a pharmaceutically effective amount of a compound of formula (1) or of formula (10), an analog thereof, or a pharmaceutically acceptable salt thereof; and (ii) monitoring levels of compound (1), the pharmaceutically acceptable salt thereof, or a metabolite thereof in the subject using pharmacokinetic profiling, wherein dosing of the compound or salt thereof is selected to result in undetectable concentrations of the compound or a metabolite thereof in whole blood, plasma, serum, or cerebrospinal fluid of the subject at 3 days, 4 days, 5 days, 6 days, or 7 days post-treatment.

In some embodiments, the treatment method comprises (i) administering, over a first time interval (e.g., 7 days), a plurality of doses of a therapeutic agent including a compound of formula (1) or of formula (10), an analog thereof, or a pharmaceutically acceptable salt thereof, wherein the plurality of doses is administered over a second time interval (e.g., two to five consecutive days for a first time interval of a week) within the first time interval; and (ii) repeating step (i) one or more additional times. In some embodiments, the subject undergoing treatment has, or is at risk of having, cancer. In some embodiments, the treatment method further comprises the step of waiting for a predetermined waiting time (e.g., the waiting time is the same length as the first time interval) between one or more repetitions of step (i). In some embodiments, the subject is a human.

In some embodiments, the pharmaceutical composition is administered to a subject once daily. In some embodiments, the pharmaceutical composition is administered to a subject according to an infrequent dosing regimen (e.g., administered once per week or less frequently). In some embodiments, the pharmaceutical composition is administered to a subject according to a frequent dosing regimen (e.g., administered more than once per week). In some embodiments, the pharmaceutical composition is administered to a subject once weekly. In some embodiments, the pharmaceutical composition is administered to a subject once every four weeks. In some embodiments, the pharmaceutical composition is administered to a subject twice a week. In some embodiments, the pharmaceutical composition is administered to a subject three times a week. In some embodiments, the pharmaceutical composition is administered to a subject four times a week. In some embodiments, the pharmaceutical composition is administered to a subject once every two weeks. In some embodiments, the pharmaceutical composition is administered to a subject once every three weeks. In some embodiments, the pharmaceutical composition is administered to a subject in a repeated cycle of once weekly, once every two weeks, once every three weeks, once every four weeks or combinations thereof.

In one aspect, provided herein are methods of identifying whether a subject having a condition is likely to be responsive to a treatment regimen. In some embodiments, the methods comprises (i) obtaining a biological sample from the subject; (ii) measuring RNA modifications levels and/or expression or activity levels of one or more of the proteins from Tables 1 and 3 and/or the presence or absence of one or more mutations in at least one gene encoding one or more proteins from Tables 1 and 3 in the sample; (iii) comparing the levels measured and/or the mutations found in the sample to those for a pre-determined standard; and (iv) determining whether the subject is likely to be responsive to the treatment regimen, based on the levels measured and/or mutations found in the sample to those for the pre-determined standard. In one aspect, provided herein are methods of providing a prognosis for a subject with a condition. In some embodiments, the methods comprises (i) obtaining a biological sample from the subject; (ii) measuring RNA modifications levels and/or expression or activity levels of one or more of the proteins from Tables 1 and 3 and/or the presence or absence of one or more mutations in at least one gene encoding one or more proteins from Tables 1 and 3 in the sample; (iii) comparing the levels measured and/or the mutations found in the sample to those for a pre-determined standard; and (iv) determining a prognosis for the subject, based on the levels measured and/or mutations found in the sample to those for the pre-determined standard.

In some embodiments, the subject has, or is at risk of having, cancer. In some embodiments, the treatment regimen comprises administering an effective amount of compound (1) or an analog thereof. In one embodiment, the RNA is mRNA. In one embodiment, the RNA is miRNA. In one embodiment, the RNA modification is methylation. In one embodiment, the RNA modification is $N^6$-Methyladenosine ($m^6A$). In one embodiment, the RNA modification is $m^6A$ mRNA methylation. In one embodiment, the subject is a human. In one embodiment, the subject is a domesticated pet, such as a cat or dog. In one embodiment, the protein is an RNA Reader, e.g., YTHDF3. In one embodiment, the protein is an RNA Writer. In one embodiment, the protein is an RNA Eraser.

In one aspect, provided herein are methods of identifying and treating a subject having a condition and who is likely to be responsive to a treatment regimen described herein. In some embodiments, the method comprises (i) identifying whether a subject having a condition is likely to be responsive to a treatment regimen described herein; and (ii) treating with the treatment regimen a subject determined likely to be responsive to that treatment regimen. In some embodiments, the subject has, or is at risk of having, cancer. In some embodiments, the treatment regimen comprises administering an effective amount of compound (1) or an analog thereof.

In one aspect, provided herein are methods of assessing the effectiveness of or monitoring a subject having a condition and undergoing treatment according to a treatment regimen described herein. In some embodiments, the method comprises (i) obtaining a biological sample from the subject; (ii) measuring RNA modifications levels and/or expression or activity levels of one or more of the proteins from Tables 1 and 3 and/or the presence or absence of one or more mutations in at least one gene encoding one or more proteins from Tables 1 and 3 in the sample; (iii) comparing the levels measured and/or the mutations found in the sample to those for a pre-determined standard; and (iv) determining whether the subject is responsive to the treatment regimen, based on the levels measured and/or mutations found in the sample to those for the pre-determined standard.

In some embodiments, the subject has, or is at risk of having, cancer. In some embodiments, the treatment regimen comprises administering an effective amount of compound (1) or an analog thereof. In one embodiment, the RNA is mRNA. In one embodiment, the RNA is miRNA. In one embodiment, the RNA modification is methylation. In one embodiment, the RNA modification is $N^6$-Methyladenosine ($m^6A$). In one embodiment, the RNA modification is $m^6A$ mRNA methylation. In one embodiment, the subject is a human. In one embodiment, the subject is a domesticated pet, such as a cat or dog. In one embodiment, the protein is an RNA Reader, e.g., YTHDF3. In one embodiment, the protein is an RNA Writer. In one embodiment, the protein is an RNA Eraser.

In one aspect, provided herein are methods for screening a potential therapeutic for a condition. In some embodiments, the method comprises (i) contacting a protein from Tables 1 and 3 with a test compound suspected of being a therapeutic for the condition; (ii) measuring the binding affinity or interaction of the test compound to the protein; and (iii) comparing the binding affinity or interaction of test compound to a pre-determined threshold, wherein an affinity or interaction of the test compound comparable to or greater than the threshold is indicative of a therapeutic for the condition. In some embodiments, the condition is cancer. In some embodiments, the pre-determined threshold is the affinity or interaction of compound (1) or an analog thereof to the protein. In some embodiments, the pre-determined threshold is the affinity or interaction of compound (1) to the protein. In some embodiments, the protein is an RNA Reader, e.g., YTHDF3. In some embodiments, the protein is an RNA Writer. In some embodiments, the protein is an RNA Eraser.

In one aspect, provided herein are methods for screening a potential therapeutic for a condition. In some embodiments, the method comprises (i) contacting a protein from Tables 1 and 3 with a reference compound under conditions where the reference compound binds to or interacts with the protein; (ii) contacting the protein from Tables 1 and 3 with a test compound suspected of being a therapeutic for the condition; (iii) measuring the binding affinities or interactions of the reference and test compounds to the protein; and (iv) comparing the binding affinities or interactions of the reference and test compounds, wherein a comparable or stronger affinity or interaction of the test compound relative to the reference compound is indicative of a therapeutic for the condition. In one embodiment, the reference compound is compound (1) or an analog thereof. In one embodiment, the reference compound is compound (1). In one embodiment, the condition is cancer. In one embodiment, the protein is an RNA Reader, e.g., YTHDF3. In one embodiment, the protein is an RNA Writer. In one embodiment, the protein is an RNA Eraser.

In one aspect, provided herein are methods for screening a potential therapeutic for a condition. In some embodiments, the method comprises (i) using a processor, modeling binding or interaction, if any, of a 3-dimensional structure of a test compound suspected of being a therapeutic for the condition to a 3-dimensional structure of a protein from Tables 1 and 3; (ii) using the processor, determining the binding affinity or interaction of the test compound structure to the protein structure; and (iii) using the processor, comparing the binding affinity or interaction of test compound to a pre-determined threshold, wherein an affinity or interaction of the test compound comparable to or greater than the threshold is indicative of a therapeutic for the condition. In one embodiment, the pre-determined threshold is the affinity or interaction of compound (1) or an analog thereof to the protein. In one embodiment, the pre-determined threshold is the affinity or interaction of compound (1) to the protein. In some embodiments, the condition is cancer. In one embodiment, the protein is an RNA Reader, e.g., YTHDF3. In one embodiment, the protein is an RNA Writer. In one embodiment, the protein is an RNA Eraser.

In one aspect, provided herein are methods for screening a potential therapeutic for a condition. In some embodiments, using a processor, the method comprises (i) using a computational docking method to model binding or interaction, of one or more 3-dimensional structures (conformations) of a test molecule suspected of being a therapeutic for the condition to a 3-dimensional structure or model of a protein from Tables 1 and 3; (ii) using the computational method to estimate the binding or interaction, if any, of a 3-dimensional structure of of the test molecule structure to the structure or model of the protein; and (iii) using the computational method to compare the binding affinities or interactions of the reference and test compounds to the protein; and (iv) using the processor, comparing the binding affinities or interactions of the reference and test compound structures, wherein a comparable or stronger affinity or interaction of the test compound relative to the reference compound is indicative of a therapeutic for the condition. In one embodiment, the reference compound structure is the structure compound (1) or an analog thereof. In some embodiments, the reference compound structure is the structure is compound (1). In some embodiments, the condition is cancer. In some embodiments, the protein is an RNA Reader, e.g., YTHDF3. In some embodiments, the protein is an RNA Writer. In some embodiments, the protein is an RNA Eraser.

In one aspect, provided herein are methods of treating a subject having a condition, such as cancer, by administering agents that modulate the transcription, translation, or biological activity of YTHDF3 or other proteins in Tables 1 and 3 or nucleic acids encoding these proteins. The agents include, but are not limited to siRNA, antisense nucleic acids, ribozymes, triple-helix-forming agents, antibodies, and polypeptides, as well as small molecule compounds. Preferably, the siRNA, antisense nucleic acids, ribozymes, triple-helix-forming agents inhibit the translation or transcription of one or more genes in Tables 1 and 3. To accomplish this, oligonucleotides used are designed on the basis of relevant sequences unique to the target gene. A variety of gene therapy approaches may be used in accordance with the invention to modulate expression of the genes in Tables 1 and 3. For example, antisense DNA molecules may be engineered and used to block translation of YTHDF3 mRNA in vivo. Alternatively, ribozyme molecules may be designed to cleave and destroy the YTHDF3 mRNAs in vivo. Alternatively, oligonucleotides designed to hybridize to the 5' region of the YTHDF3 gene (including the region upstream of the coding sequence) and form triple helix structures block or reduce transcription of the YTHDF3 gene. In yet another alternative, nucleic acid encoding the full length wild-type YTHDF3 message may be introduced in vivo into cells which otherwise would be unable to produce the wild-type YTHDF3 gene product in sufficient quantities or at all.

In one embodiment, the pharmaceutical composition includes a pharmaceutically acceptable carrier. In some embodiments, the subject has, or is at risk of having, cancer. In some embodiments, the subject is, or is at risk of being, infected with a virus. In some embodiments, the subject is a human. In some embodiments, the dose of compound (1) or a pharmaceutically acceptable salt thereof ranges from about 125 mg to about 625 mg. In some embodiments, a sample obtained from the subject is assayed for cleaved and/or total cytokeratin-18. determining whether the treatment regimen should continue based on the results of the cleaved and/or total cytokeratin-18 assays. In some embodiments, a treatment regiment described herein further comprises the step of administering a second therapeutic agent, wherein compound (1), the pharmaceutically acceptable salt thereof, or the analog thereof is administered before, simultaneously, or after the second therapeutic agent.

In one aspect, provided herein are methods of identifying whether a subject having a condition is likely to be responsive to a treatment regimen described herein. In some embodiments, the methods comprises (i) obtaining a biological sample from the subject; (ii) measuring expression, post-translational modifications, or activity levels of or mutations in eIF2-alpha, ATF4, CHOP, or DR5 in the sample; (iii) comparing the levels measured and/or the mutations found in the sample to those for a pre-determined standard; and (iv) determining whether the subject is likely to be responsive to the treatment regimen, based on the levels measured and/or mutations found in the sample to those for the pre-determined standard. In another aspect, provided herein are methods of assessing the effectiveness of a treatment regimen described herein, monitoring, or providing a prognosis for a subject with a condition. In some embodiments, the methods comprises (i) obtaining a biological sample from the subject; (ii) measuring expression, post-translational modifications, or activity levels of or mutations in eIF2-alpha, ATF4, CHOP, or DR5 in the sample in the sample; (iii) comparing the levels measured and/or the mutations found in the sample to those for a pre-determined standard; and (iv) determining a prognosis or determining whether the subject is responsive to the treatment regimen, based on the levels measured and/or mutations found in the sample to those for the pre-determined standard. In some embodiments, the subject has, or is at risk of having, cancer. In some embodiments, the subject has, or is at risk of having, cancer. In some embodiments, the subject is, or is at risk of being, infected with a virus. In some embodiments, the treatment regimen comprises administering an effective amount of compound (1), a pharmaceutically acceptable salt thereof, or an analog thereof.

In one aspect, provided herein are methods of identifying whether a subject having a condition is likely to be responsive to a treatment regimen described herein. In some embodiments, the methods comprises (i) obtaining a biological sample from the subject; (ii) measuring expression, post-translational modifications, or activity levels of or mutations in at least one dopamine receptor in the sample; (iii) comparing the levels measured and/or the mutations found in the sample to those for a pre-determined standard; and (iv) determining whether the subject is likely to be responsive to the treatment regimen, based on the levels measured and/or mutations found in the sample to those for the pre-determined standard. In another aspect, provided herein are methods of assessing the effectiveness of a treatment regimen described herein, monitoring, or providing a prognosis for a subject with a condition. In some embodiments, the methods comprises (i) obtaining a biological sample from the subject; (ii) measuring expression, post-translational modifications, or activity levels of or mutations in at least one dopamine receptor in the sample; (iii) comparing the levels measured and/or the mutations found in the sample to those for a pre-determined standard; and (iv) determining a prognosis or determining whether the subject is responsive to the treatment regimen, based on the levels measured and/or mutations found in the sample to those for the pre-determined standard. In some embodiments, the subject has, or is at risk of having, cancer. In some embodiments, the subject has, or is at risk of having, cancer. In some embodiments, the treatment regimen comprises administering an effective amount of compound (1), a pharmaceutically acceptable salt thereof, or an analog thereof. In some embodiments, the dopamine receptor is selected from DRD2, DRD2S, DRD2L, and DRD3. In some embodiments, the dopamine receptor is from the D2-like family of dopamine receptors.

In one aspect, provided herein are methods for screening a potential therapeutic for a condition. In some embodiments, the method comprises (i) contacting at least one G protein-coupled receptor (GPCR) with a test molecule suspected of being a therapeutic for a condition; (ii) measuring the binding affinity, interaction or GPCR signalling of the test compound to the GPCR; and (iii) comparing the binding affinity or interaction of test molecule to a pre-determined threshold, wherein GPCR antagonism or GPCR signaling antagonism of the test molecule comparable to or greater than the threshold is indicative of a therapeutic for the condition. In one embodiment, the condition is cancer. In one embodiment, the pre-determined threshold is the GPCR antagonism or GPCR signaling antagonism of compound (1) or a pharmaceutically acceptable salt thereof, or an analog thereof.

In one aspect, provided herein are methods for screening a potential therapeutic for a condition. In some embodiments, the method comprises (i) contacting at least one dopamine receptor with a test molecule suspected of being a therapeutic for a condition; (ii) measuring the binding affinity or interaction of the test molecule to the at least one dopamine receptor; and (iii) comparing the binding affinity or interaction of the test molecule to a pre-determined determined threshold, wherein inhibition of the at least one dopamine receptor by the test molecule comparable to or greater than the threshold is indicative of a therapeutic for the condition. In some embodiments, the condition is cancer. In some embodiments, the dopamine receptor is selected from DRD2, DRD2S, DRD2L, and DRD3. In some embodiments, inhibition of the D2-like family of dopamine receptors is indicative of a therapeutic for the condition. In some embodiments, inhibition of both DRD2 and DRD3 dopamine receptors is indicative of a therapeutic for the condition. In some embodiments, the pre-determined threshold is the inhibition of the at least one dopamine receptor by compound (1) or a pharmaceutically acceptable salt thereof, or an analog thereof to the dopamine receptor.

In one aspect, provided herein are methods for screening a potential therapeutic for a condition. In some embodiments, using a processor, the method comprises (i) using a computational docking method to model binding or interaction, if any, of one or more 3-dimensional structures (conformations) of a test molecule suspected of being a therapeutic for the condition to a 3-dimensional structure or model of at least one dopamine receptor; (ii) using the computational method to estimate the binding affinity or interaction of the test molecule structure to the structure or model of the at least one dopamine receptor; and (iii) using the computational method to compare the binding affinity or interaction of the test molecule to a pre-determined threshold, wherein inhibition of the at least one dopamine receptor by the test molecule comparable to or greater than the threshold is indicative of a therapeutic for the condition. one embodiment, the condition is cancer. In some embodiments, the dopamine receptor is selected from DRD2, DRD2S, DRD2L, and DRD3. one embodiment, inhibition of the D2-like family of dopamine receptors is indicative of a therapeutic for the condition. In one embodiment, inhibition of both DRD2 and DRD3 dopamine receptors is indicative of a therapeutic for the condition. In one embodiment, the pre-determined threshold is the inhibition of the at least one dopamine receptor by compound (1) or a pharmaceutically acceptable salt thereof, or an analog thereof to the dopamine receptor. In one embodiment, a pharmacophore modeling approach may be used to compare different dopamine antagonist compounds in three dimensions as described in Hogberg & Norinder, Chapter 3. Theoretical and Experimental Methods in Drug Design applied on Antipsychotic Dopamine Antagonists in "A Textbook of Drug Design and Development," 1991, pp 54-91, Krogsgaard-Larsen & Bundgaard, Eds., Harwood Academic Publishers GmbH, Chur, Switzerland.

In one aspect, provided herein are methods of treating and assessing the effectiveness of a treatment in a subject having a condition. In some embodiments, the method comprises (i) treating the subject according to a treatment method described herein (ii) assessing as described herein the treatment's effectiveness. In some embodiments, the subject has, or is at risk of having, cancer. In one embodiment, the treatment regimen comprises administering an effective amount of compound (1) or a pharmaceutically acceptable salt thereof or an analog thereof.

The foregoing summary, as well as the following detailed description of embodiments of the compositions and methods of treatment, will be better understood when read in conjunction with the appended claims. It should be understood, however, that the invention is not limited to the precise arrangements and instrumentalities described herein.

BRIEF DESCRIPTION OF THE DRAWINGS

The foregoing summary, as well as the following detailed description of embodiments of the present invention, will be better understood when read in conjunction with the appended drawings of an exemplary embodiment. It should be understood, however, that the invention is not limited to the precise arrangements and instrumentalities shown.

In the drawings.

DETAILED DESCRIPTION OF THE INVENTION

Figure 1:
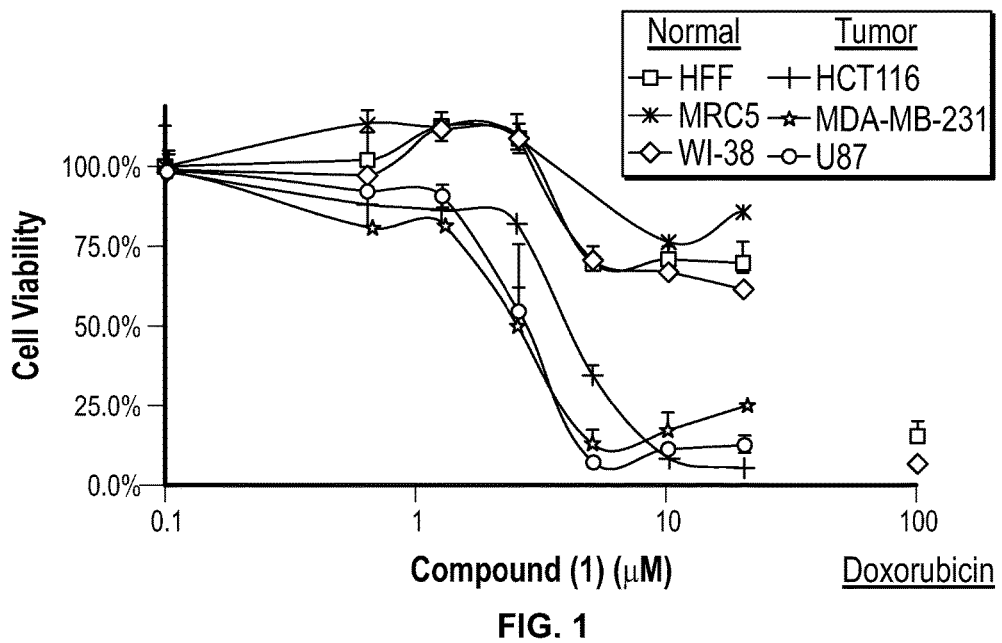
FIG. 1 illustrates a dose response relation showing effects of various concentrations of compound (1) on viability of tumor and normal cells.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, Pa., 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808, as well as U.S. Pat. No. 8,673,923. The content of each of the foregoing references is hereby incorporated by reference in its entirety.

The singular terms "a," "an," and "the" are not intended to be limiting and include plural referents unless explicitly stated or the context clearly indicates otherwise.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^4$) occurs more than one time in any constituent or formula for a compound, its definition at each occurrence is independent of its definition at every other occurrence. Thus, for example, if a group is shown to be substituted with 0-3 $R^4$ moieties, then the group may optionally be substituted with up to three $R^4$ moieties and $R^4$ at each occurrence is selected independently from the definition of $R^4$. Also, combinations of substituents and/or variables are permissible, but only if such combinations result in stable compounds.

When an atom or chemical moiety is followed by a subscripted numeric range (e.g., $C_{1-6}$), it will be appreciated that this is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched and straight-chain saturated aliphatic hydrocarbon groups having the specified number of carbon atoms. For example, $C_{1-6}$ alkyl is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, isobutyl s-butyl, t-butyl, n-pentyl, s-pentyl, neopentyl and n-hexyl. In certain embodiments, a straight chain or branched chain alkyl has six or fewer carbon atoms in its backbone (e.g., $C_1$-$C_6$ for straight chain, $C_3$-$C_6$ for branched chain), and in another embodiment, a straight chain or branched chain alkyl has four or fewer carbon atoms. Likewise, cycloalkyls have from three to eight carbon atoms in their ring structure, and in other embodiments, cycloalkyls have five or six carbons in the ring structure. Most preferred is ($C_1$-$C_6$)alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, —NH$_2$, —N(CH$_3$)$_2$, —C(=O)OH, trifluoromethyl, —C(=O)O($C_1$-$C_4$)alkyl, —C(=O)NH$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

Unless the number of carbons is otherwise specified, "lower alkyl" includes an alkyl group, as defined above, but having from one to six carbon atoms, preferably one to four, in its backbone structure. "Lower alkenyl" and "lower alkynyl" have chain lengths of 2-6 carbon atoms and preferably 2-4 carbon atoms.

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has six or fewer carbon atoms in its backbone (e.g., $C_2$-$C_6$ for straight chain, $C_3$-$C_6$ for branched chain). Likewise, cycloalkenyl groups may have from three to eight carbon atoms in their ring structure, and in some embodiments, cycloalkenyl groups have five or six carbons in the ring structure. The term "$C_2$-$C_6$" includes alkenyl groups containing two to six carbon atoms. The term "$C_3$-$C_6$" includes alkenyl groups containing three to six carbon atoms.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. In certain embodiments, a straight chain or branched chain alkynyl group has six or fewer carbon atoms in its backbone (e.g., $C_2$-$C_6$ for straight chain, $C_3$-$C_6$ for branched chain) The term "$C_2$-$C_6$" includes alkynyl groups containing two to six carbon atoms. The term "$C_3$-$C_6$" includes alkynyl groups containing three to six carbon atoms.

As used herein, "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

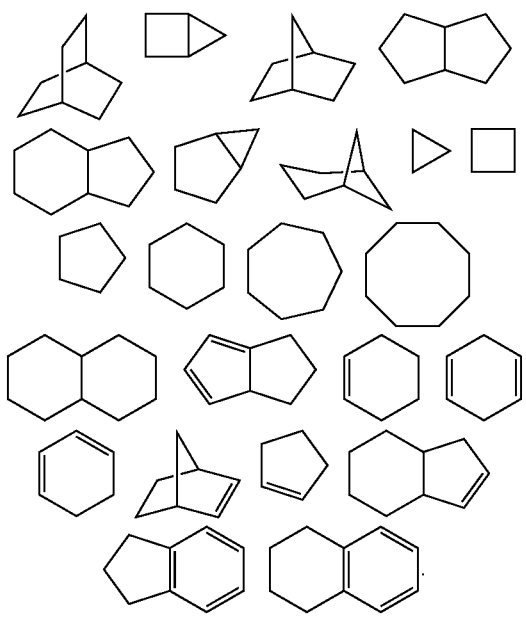

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, "cycloalkylalkyl" refers to an alkyl group substituted by a cycloalkyl group. Example cycloalkylalkyl groups include cyclopropylalkyl, cyclohexylalkyl, and the like.

As used herein, "heterocycloalkyl" refers to a non-aromatic heterocycle where one or more of the ring-forming atoms can be a heteroatom such as an O, N, or S atom. Heterocycloalkyl groups can include mono- or polycyclic (e.g., having 2, 3 or 4 fused rings) ring systems as well as spirocycles. Example heterocycloalkyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl can be moieties that have one or more aromatic rings fused (i.e., having a bond in common with) to the nonaromatic heterocyclic ring, for example quinolyl, isoquinolyl, and benzo derivatives of heterocycles. A heterocycloalkyl group having one or more fused aromatic rings are attached though either the aromatic or non-aromatic portion. Also included in the definition of heterocycloalkyl can be moieties where one or more ring-forming atoms can be substituted by 1 or 2 oxo or sulfido groups. In some embodiments, the heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "heterocycloalkylalkyl" refers to an alkyl group substituted by a heterocycloalkyl group. Example heterocycloalkylalkyl groups include morpholinoalkyl and piperazinylalkyl, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, and the like. In some embodiments, an aryl group has from 6 to about 20 carbon atoms.

As used herein, "arylalkyl" refers to an alkyl group substituted by an aryl group. Example arylalkyl groups include benzyl and phenylethyl.

As used herein, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, a "heteroarylalkyl" group refers to an alkyl group substituted by a heteroaryl group. An example of a heteroarylalkyl group is pyridylmethyl.

As used herein, "halo" or "halogen" refers to a fluorine, chlorine, bromine, or iodine atom, preferably, fluorine, chlorine, or bromine, more preferably, fluorine or chlorine. The term "perhalogenated" refers to a moiety wherein all hydrogens are replaced by halogen atoms.

The term "haloalkyl" refers to alkyl moieties having a halogen atom replacing a hydrogen atom on one or more carbons of the hydrocarbon backbone. $C_1$-$C_6$ haloalkyl is intended to include a straight chain or branched alkyl having six or fewer carbon atoms in its backbone and a halogen atom replacing a hydrogen atom on one or more carbons of the hydrocarbon backbone.

The term "alkoxy" or "alkoxyl" includes substituted and unsubstituted alkyl, alkenyl, and alkynyl groups covalently linked to an oxygen atom. $C_1$-$C_6$ alkoxy refers to moieties having six of few carbon atoms in the hydrocarbon backbone. Examples of alkoxy groups (or alkoxyl radicals) include methoxy, ethoxy, isopropyloxy, propoxy, butoxy, and pentoxy groups. Preferred are ($C_1$-$C_3$) alkoxy, particularly ethoxy and methoxy. Examples of substituted alkoxy groups include halogenated alkoxy groups.

The term "hydroxy" or "hydroxyl" includes groups with an —OH or —O⁻.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention are synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts can be found in *Remington's Pharmaceutical Sciences*, 17th ed., Mack Publishing Company, Easton, Pa., 1985, p. 1418, *Journal of Pharmaceutical Science*, 66, 2 (1977), and P. H. Stahl and C. G. Wermuth, editors, *Handbook of Pharmaceutical Salts: Properties, Selection and Use*, 2nd Revised edition, Weinheim/Zürich: Wiley-VCH/VHCA (2011), each of which is incorporated herein by reference in its entirety.

Examples of suitable inorganic acids include hydrochloric acid, sulphuric acid, phosphoric acid, or hydrobromic acid, while examples of suitable organic acids can include carboxylic acid, sulpho acid, or sulphonic acid, such as acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxybenzoic acid, cinnamic acid, mandelic acid, citric acid, maleic acid, salicylic acid, trifluoroacetic acid, 3-aminosalicylic acid, ascorbic acid, embonic acid, nicotinic acid, isonicotinic acid, oxalic acid, gluconic acid, amino acids, methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid. Examples of suitable inorganic bases can include sodium hydroxide, potassium hydroxide and ammonia, while examples of suitable organic bases are amines, e.g., tertiary amines, such as trimethylamine, triethylamine, pyridine, N,N-dimethylaniline, quinoline, isoquinoline, α-picoline, β-picoline, γ-picoline, quinaldine, or pyrimidine.

I. COMPOUND (1), SALTS THEREOF AND SYNTHESES THEREOF

The inventors have found in in vitro models, in animal models, and in human clinical trials that ONC201 (compound (1)) has broad anti-cancer activity, low toxicity including few, if any, adverse effects, low genotoxicity, and high bioavailability including oral bioavailability. These features allows ONC 201 and various analogs to be particularly well suited for a variety of applications.

In one aspect, the present invention provides compound (1):

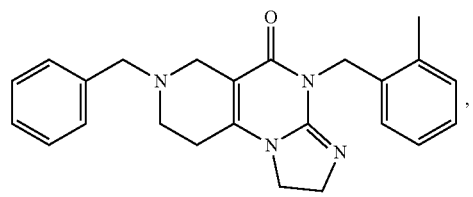 [SMILES: Cc1ccccc1CN1C(=O)C2=C(CCN(Cc3ccccc3)C2)N2CCN=C12]

analogs thereof, and pharmaceutically acceptable salts thereof, as well as processes of making the same. Compound (1) can be prepared by the synthetic process illustrated in Scheme 1 below.

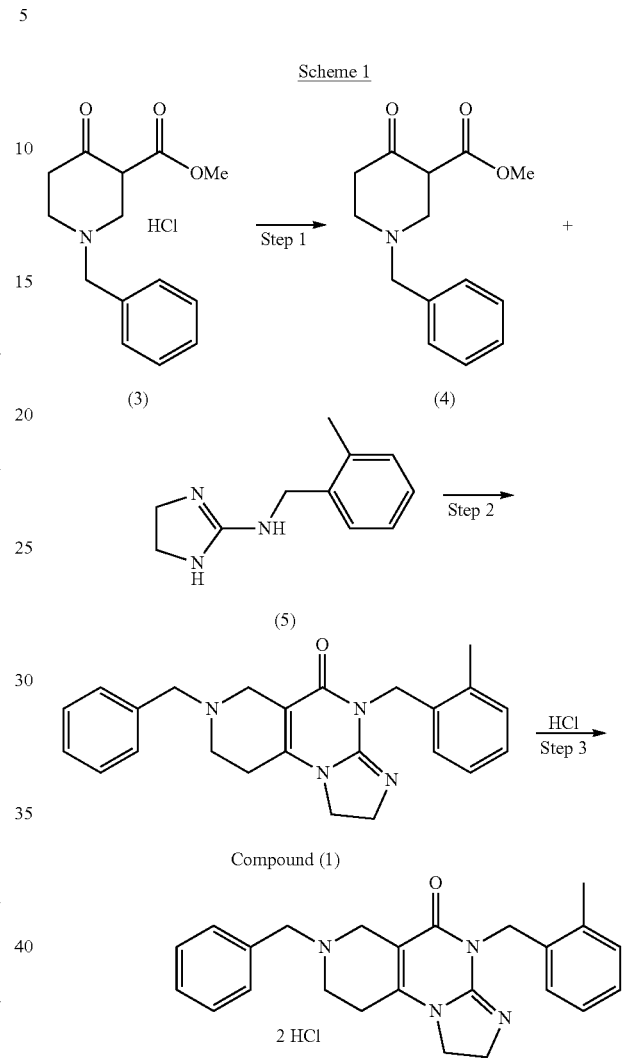

In one embodiment, synthesis of a dihydrochloride salt of compound (1) starts with commercially available intermediary N-Benzyl-3-carbomethoxy-4-piperidone hydrochloride, compound (3). In one embodiment, the synthetic process includes neutralizing intermediary compound (3) with a base (Step 1) to produce compound (4), a free base. In one embodiment, the synthetic process includes neutralizing intermediary compound (3) with an inorganic base to produce compound (4). In one embodiment, the synthetic process includes neutralizing intermediary compound (3) with an organic base to produce compound (4). In one embodiment, intermediary compound (3) is neutralized in the presence of an alcohol. For example, intermediary compound (3) is neutralized in the presence of n-butanol. In one embodiment, intermediary compound (3) is neutralized in the presence of at least one organic solvent. For example, intermediary compound (3) is neutralized in the presence of n-butanol and/or ethyl acetate. In one embodiment, intermediary compound (3) is neutralized in the presence of a base and at least one organic solvent. For example, intermediary compound (3) is neutralized in the presence of NaHCO₃ and n-butanol. In one embodiment, intermediary compound (3) is neutralized in the presence of n-butanol and triethyl amine (Et₃N).

In one embodiment, the synthetic process includes reacting compound (4) with compound (5) (Step 2) to produce intermediary compound of (1). In one embodiment, the reaction in Step 2 includes heating compound (4) with compound (5). In one embodiment, the reaction in Step 2 includes refluxing heating compound (4) and compound (5) in the presence of a solvent. In one embodiment, the reaction in Step 2 includes use of Dean-stark trap to remove water and/or methanol (MeOH) formed in the reaction.

In one embodiment, the synthetic process includes forming a dihydrochloride salt of compound (1) (Step 3). In one embodiment, the reaction in Step 3 includes treating compound (1) with HCl in dioxane. In one embodiment, the reaction in Step 3 includes treating compound (3) with 4N HCl in dioxane. In one embodiment, the synthetic process optionally includes recrystallization of the di-salt of compound (1).

In one preferred embodiment, the synthetic process for the preparation of the di-hydrochloride salt of compound (1) is as illustrated in the following Scheme 2.

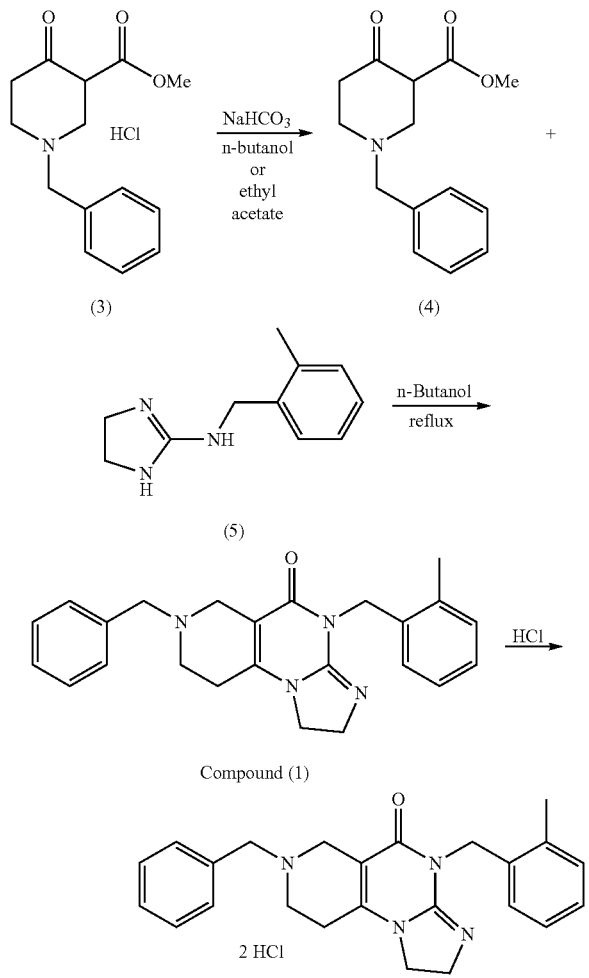

II. TNF-RELATED APOPTOSIS-INDUCING LIGAND ("TRAIL")

TRAIL protein can be assayed in a test sample obtained from a subject to detect TRAIL expression induced by the compounds and their salts described herein Immunoassays can be used to assay TRAIL in a sample, including, but not limited to, enzyme-linked immunosorbent assay (ELISA), enzyme-linked immunofiltration assay (ELIFA), flow cytometry, immunoblot, immunoprecipitation, immunohistochemistry, immunocytochemistry, luminescent immunoassay (LIA), fluorescent immunoassay (FIA), and radioimmunoassay. Assay methods may be used to obtain qualitative and/or quantitative results. Specific details of suitable assay methods for both qualitative and quantitative assays of a sample are described in standard references, illustratively including E. Harlow & D. Lane, Antibodies: A Laboratory Manual, Cold Spring Harbor Laboratory Press, 1988; F. Breitling & S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; Ormerod, M. G., Flow Cytometry: a practical approach, Oxford University Press, 2000; Givan, A. L., Flow Cytometry: first principles, Wiley, New York, 2001; Gorczyca, W., Flow Cytometry in Neoplastic Hematology: morphologic-immunophenotypic correlation, Taylor & Francis, 2006; Crowther, J. R., The ELISA Guidebook (Methods in Molecular Biology), Humana Press, 2000; Wild, D., The Immunoassay Handbook, 3$^{rd}$ Edition, Elsevier Science, 2005, and J. Sambrook and D. W. Russell, Molecular Cloning: A Laboratory Manual, Cold Spring Harbor Laboratory Press, 3$^{rd}$ ed., 2001.

Examples of protocols for assaying and analyzing a sample for TRAIL for the purpose of detection of an effect of a pharmaceutical composition are described in U.S. Pat. 8,673,923 to Wafik S. El-deiry et al., which is incorporated by reference herein in its entirety.

In one embodiment, TRAIL assays are used to monitor a subject. Thus, for example, a test sample is obtained from the subject before treatment with a pharmaceutical composition and at one or more times during and/or following treatment in order to assess effectiveness of the treatment. In a further example, a test sample is obtained from the subject at various times in order to assess the course or progress of disease or healing. In one embodiment, death receptors can also be analyzed from circulating tumor cells to see if the administration of a compound or its salt described herein increases the amount or type of death receptors.

Cancers treated using methods and compositions described herein are characterized by abnormal cell proliferation including, but not limited to, pre-neoplastic hyperproliferation, cancer in-situ, neoplasms and metastasis. Methods and compositions described herein can be used for prophylaxis, as well as amelioration of signs and/or symptoms of cancer. The terms "treating" and "treatment" used to refer to treatment of a cancer in a subject include: preventing, inhibiting or ameliorating the cancer in the subject, such as slowing progression of the cancer and/or reducing or ameliorating a sign or symptom of the cancer. Examples of cancers treated using methods and compositions described herein include, but are not limited to, breast cancer, CNS cancers, colon cancer, ovarian cancer, prostate cancer, leukemia, lung cancer, and lymphoma.

III. COMPOUND (10) AND SALTS THEREOF

In one aspect, provided herein are compounds and related salts of compound (10) and processes of making the same. Persons skilled in the art will understand that the general principles and concepts described herein in conjunction with compound (1) and salts thereof, including principles and concepts related to methods and pharmaceutical compositions, apply with equal force to compounds of formula (10) and salts thereof.

In some embodiments, provided herein are compounds represented by formula (10):

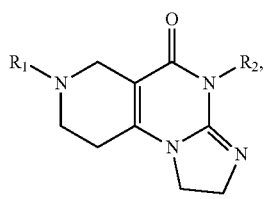

(10)

wherein $R_1$ and $R_2$ independently represent hydrogen, alkyl, cycloalkyl, cycloalkylalkyl, heterocycloalkyl, heterocycloalkylalkyl, aryl, heteroaryl, arylalkyl, heteroarylalkyl, alkoxyalkyl, alkoxycarbonyl, aralkoxy, aralkylthio, and acyl radicals, wherein when $R_1$ represents $CH_2Ph$, $R_2$ does not represent $CH_2$-((2-$CH_3$)-Ph).

In some embodiments, $R_1$ and $R_2$ are independently selected from the group consisting of H, $C_{1-4}$alkylphenyl, $C_{1-4}$alkylphenylketone, $C_{1-4}$benzyl-piperazine, $C_{1-4}$alkylthienyl, $C_{1-4}$alkylpyridinyl, $C_{1-4}$alkylisoxazolidinyl, $C_{1-4}$alkylmorpholinyl, $C_{1-4}$alkylthiazolyl, and $C_{1-4}$alkylpyrazinyl wherein $C_{1-4}$alkyl, $C_{1-4}$alkylphenyl, $C_{1-4}$alkylphenylketone, $C_{1-4}$benzyl-piperazine, $C_{1-4}$alkylthienyl, $C_{1-4}$alkylpyridinyl, $C_{1-4}$alkylisoxazolidinyl, $C_{1-4}$alkylmorpholinyl, $C_{1-4}$alkylthiazolyl, and $C_{1-4}$alkylpyrazinyl are optionally substituted with $C_{1-4}$alkyl, $C_{1-4}$alkoxyl, hydroxyl, perhalogenated $C_{1-4}$alkyl, or halo. In some embodiments, $R_1$ and/or $R_2$ is a substituted or unsubstituted, arylalkyl or heteroarylalkyl. In some embodiments, the heteroarylalkyl is selected from $C_{1-4}$alkylpyrrolyl, $C_{1-4}$alkylfuryl, $C_{1-4}$alkylpyridyl, $C_{1-4}$alkyl-1,2,4-thiadiazolyl, $C_{1-4}$alkylpyrimidyl, $C_{1-4}$alkylthienyl, $C_{1-4}$alkylisothiazolyl, $C_{1-4}$alkylimidazolyl, $C_{1-4}$alkyltetrazolyl, $C_{1-4}$alkylpyrazinyl, $C_{1-4}$alkylpyrimidyl, $C_{1-4}$alkylquinolyl, $C_{1-4}$alkylisoquinolyl, $C_{1-4}$alkylthiophenyl, $C_{1-4}$alkylbenzothienyl, $C_{1-4}$alkylisobenzofuryl, $C_{1-4}$alkylpyrazolyl, $C_{1-4}$alkylindolyl, $C_{1-4}$alkylpurinyl, $C_{1-4}$alkylcarbazolyl, $C_{1-4}$alkylbenzimidazolyl, and $C_{1-4}$alkylisoxazolyl.

In some embodiments, $R_1$ and/or $R_2$ is a benzyl optionally substituted with one or more of the following substituents on the benzyl ring: X, —$CH_3$, —$NO_2$, —$OCH_3$, —CN, —$CXH_2$, —$CX_2H$, $C_2$-$C_4$ alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR^m$, $SR^m$, $NR^mR^n$, $NR^mC(O)R^n$, $SOR^m$, $SO_2R^m$, $C(O)R^m$, and $C(O)OR^m$; $R^m$ and $R^n$ are independently selected from hydrogen or a $C_1$-$C_4$ alkyl; and where p is an integer from 2 to 20 and X represents a halogen, including a fluorine, chlorine, bromine, or iodine atom, preferably, fluorine, chlorine, or bromine, more preferably, fluorine or chlorine.

In some embodiments, $R_1$ is selected from the group consisting of H, $CH_3$, $CH_2Ph$, $CH_2$-(4-$CF_3$-Ph), $CH_2$-(4-F-Ph), $CH_2$-(4-Cl-Ph), $CH_2$—(OCH_3-Ph), $CH_2$-((2-Cl)-Ph), $CH_2$-(2-thienyl), $CH_2$-(3-thienyl), $CH_2$-2-pyridinyl, $CH_2$-4-methyl-2-thiazolyl, $CH_2$-2-pyrazinyl, $CH_2CH_2Ph$, $CH_2CH_2$(4-N-benzyl-piperazine), $CH_2$-(2,4-di F-Ph), $CH_2$-(3,4-di Cl-Ph), $CH_2$-(3,4-di F-Ph), $CH_2$-(3,5-di F-Ph), $CH_2$-((2-$CH_3$)-Ph), $CH_2CH(OH)Ph$, (4-F-Ph)-4-oxobutyl, $CH_2CH_2NHCOOC(CH_3)_3$, $CH_2CH_2CH_2NH_2$, and $CD_2C_6D_5$. In some embodiments, $R_2$ is selected from the group consisting of H, $CH_3$, $CH_2Ph$, $CH_2$-(4-$CF_3$-Ph), $CH_2$-((2-Cl)-Ph), $CH_2$-((2-F)-Ph), $CH_2$-(2-thienyl), $CH_2CH_2Ph$, $CH_2CH_2$(4-N-benzyl-piperazine), $CH_2$-(2,4-di F-Ph), $CH_2$-(2,4-di F-Ph), $CH_2$-(2,4-di Cl-Ph), $CH_2$-(3,4-di Cl-Ph), $CH_2$-(3,4-di F-Ph), $CH_2$-(3,5-di F-Ph), $CH_2$-((2-$CH_3$)-Ph), $CH_2$(2-$CH_3$, 4-F-Ph), $CH_2$-((4-$OCH_3$)-Ph), $CH_2$-(3-pyridinyl), $CH_2$-(3-isoxazolidinyl), $CH_2CH_2$-(4-morpholinyl), $CH_2$-(2-F, 4-$CF_3$-Ph), $CH_2CH(OH)Ph$, $(CH_2)_3CO$-4F-Ph, (4-F-Ph)-4-oxobutyl, $CH_2CH_2NHCOOC(CH_3)_3$, $CH_2CH_2CH_2NH_2$, and $CD_2C_6D_5$.

In some embodiments, $R_1$ is a hydrogen. In some embodiments, $R_1$ is a substituted or an unsubstituted arylalkyl, such as a benzyl or phenylethyl group. In some embodiments, the arylalkyl is substituted with $C_{1-4}$alkyl, $C_{1-4}$alkoxyl, hydroxyl, perhalogenated $C_{1-4}$alkyl, or halo.

In one embodiment, $R_2$ is a substituted or an unsubstituted arylalkyl, such as a benzyl or phenylethyl group. In one embodiment, the arylalkyl is substituted with $C_{1-4}$alkyl, $C_{1-4}$alkoxyl, hydroxyl, perhalogenated $C_{1-4}$alkyl, or halo. In one embodiment, the arylalkyl is substituted with one or more substituents selected from the group consisting of halo, —$CH_3$, —$CF_3$, and —$OCH_3$. In one embodiment, $R_2$ is a substituted or an unsubstituted heterocycloalkylalkyl, such as a morpholinoalkyl or piperazinylalkyl group. In one embodiment, $R_2$ is a substituted or an unsubstituted heteroarylalkyl, such as an isoxazolidinylmethyl or pyridylmethyl group. In one embodiment, the heterocycloalkylalkyl or heteroarylalkyl is substituted with $C_{1-4}$alkyl, $C_{1-4}$alkoxyl, hydroxyl, perhalogenated $C_{1-4}$alkyl, or halo. In one embodiment, the heterocycloalkylalkyl or heteroarylalkyl is substituted with one or more substituents selected from the group consisting of halo, —$CH_3$, —$CF_3$, and —$OCH_3$.

In one embodiment, compound (10) has the structure of compound (80):

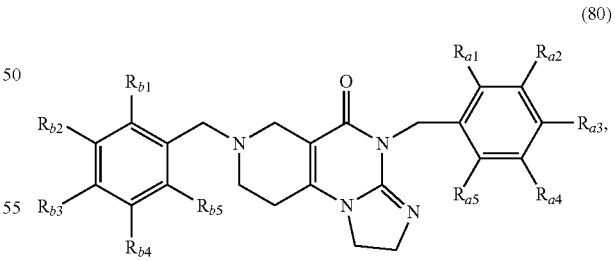

(80)

wherein $R_{a1}$, $R_{a2}$, $R_{a3}$, $R_{a4}$, $R_{a5}$, $R_{b1}$, $R_{b2}$, $R_{b3}$, $R_{b4}$, and $R_{b5}$ are each independently selected from the group consisting of X, —$CH_3$, —$NO_2$, —$OCH_3$, —CN, —$CXH_2$, —$CX_2H$, $C_2$-$C_4$ alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+l}$, —$OC_pX_{2p+1}$, $OR^m$, $SR^m$, $NR^mR^n$, $NR^mC(O)R^n$, $SOR^m$, $SO_2R^m$, $C(O)R^m$, and $C(O)OR^m$; $R^m$ and $R^n$ are independently selected from hydrogen or a $C_1$-$C_4$ alkyl; and where p is an integer from 2 to 20 and X represents a halogen.

In one embodiment, compound (10) has the structure of compound (90)

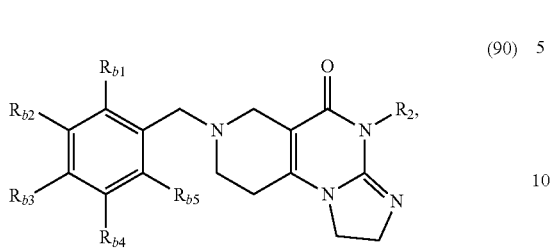

(90)

wherein $R_2$ is as defined above, and wherein $R_{b1}$, $R_{b2}$, $R_{b3}$, $R_{b4}$, and $R_{b5}$ are each independently selected from the group consisting of X, —$CH_3$, —$NO_2$, —$OCH_3$, —CN, —$CXH_2$, —$CX_2H$, $C_2$-$C_4$ alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR^m$, $SR^m$, $NR^mR^n$, $NR^mC(O)R^n$, $SOR^m$, $SO_2R^m$, $C(O)R^m$, and $C(O)OR^m$; $R^m$ and $R^n$ are independently selected from hydrogen or a $C_1$-$C_4$ alkyl; and where p is an integer from 2 to 20 and X represents a halogen.

In one embodiment, compound (10) has the structure of compound (40)

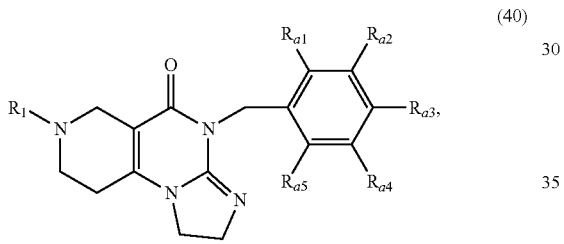

(40)

wherein $R_1$ is as defined above, and wherein $R_{a1}$, $R_{a2}$, $R_{a3}$, $R_{a4}$, and $R_{a5}$ are each independently selected from the group consisting of hydrogen, X, —$CH_3$, —$NO_2$, —$OCH_3$, —CN, —$CXH_2$, —$CX_2H$, $C_2$-$C_4$ alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR^m$, $SR^m$, $NR^mR^n$, $NR^mC(O)R^n$, $SOR^m$, $SO_2R^m$, $C(O)R^m$, and $C(O)OR^m$; $R^m$ and $R^n$ are independently selected from hydrogen or a $C_1$-$C_4$ alkyl; and where p is an integer from 2 to 20 and X represents a halogen. In one embodiment, $R_1$ is a hydrogen. In one embodiment, $R_1$ is a substituted or an unsubstituted arylalkyl, such as a benzyl or phenylethyl group. In one embodiment, the arylalkyl is substituted with $C_{1-4}$alkyl, $C_{1-4}$alkoxyl, hydroxyl, perhalogenated $C_{1-4}$alkyl, or halo. In one embodiment, the benzyl is substituted with one or more halogens. In one embodiment, the benzyl is substituted with one or more substituents selected from the group consisting of halo, —$CH_3$, —$CF_3$, and —$OCH_3$. In one embodiment, the benzyl is substituted with one halogen substituent, e.g., a fluorine substituent at an ortho or para position. In one embodiment, the benzyl is substituted with two halogen substituents, e.g., fluorine substituents at both meta positions.

In one embodiment, compound (40) has the structure of compound (45):

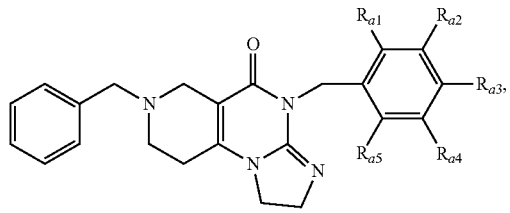

(45)

wherein $R_{a1}$, $R_{a2}$, $R_{a3}$, $R_{a4}$, and $R_{a5}$ are as defined above. In one embodiment, the benzyl is substituted with one or more halogens. In some embodiments, the benzyl is substituted with one or more substituents selected from the group consisting of halo, —$CH_3$, —$CF_3$, and —$OCH_3$. In one embodiment, $R_{a1}$ or $R_{a5}$ is a halogen, e.g., fluorine. In one embodiment, both $R_{a2}$ or $R_{a3}$ are halogen, e.g., fluorine, substituents.

In one embodiment, compound (10) has the structure of compound (50)

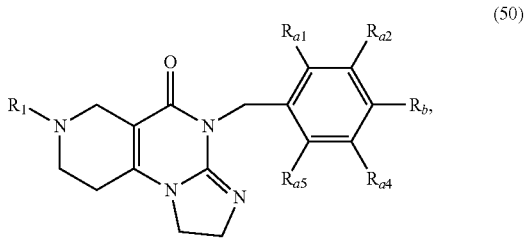

(50)

wherein $R_1$ is as defined above, and wherein $R_b$ is selected from the group consisting of X, —$CH_3$, —$NO_2$, —$OCH_3$, —CN, —$CXH_2$, —$CX_2H$, $C_2$-$C_4$ alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR^m$, $SR^m$, $NR^mR^n$, $NR^mC(O)R^n$, $SOR^m$, $SO_2R^m$, $C(O)R_m$, and $C(O)OR^m$; $R^m$ and $R^n$ are independently selected from hydrogen or a $C_1$-$C_4$ alkyl; and where p is an integer from 2 to 20 and X represents a halogen and wherein $R_{a1}$, $R_{a2}$, $R_{a4}$, and $R_{a5}$ are each independently selected from the group consisting of hydrogen, X, —$CH_3$, —$NO_2$, —$OCH_3$, —CN, —$CXH_2$, —$CX_2H$, $C_2$-$C_4$ alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR^m$, $SR^m$, $NR^mR^n$, $NR^mC(O)R^n$, $SOR^m$, $SO_2R^m$, $C(O)R^m$, and $C(O)OR^m$; $R^m$ and $R^n$ are independently selected from hydrogen or a $C_1$-$C_4$ alkyl; and where p is an integer from 2 to 20 and X represents a halogen. In one embodiment, $R_1$ is a hydrogen. In one embodiment, $R_1$ is a substituted or an unsubstituted arylalkyl, such as a benzyl or phenylethyl group. In one embodiment, the arylalkyl is substituted with $C_{1-4}$alkyl, $C_{1-4}$alkoxyl, hydroxyl, perhalogenated $C_{1-4}$alkyl, or halo. In one embodiment, $R_b$ is selected from the group consisting of halo, —$CH_3$, —$CF_3$, and —$OCH_3$. In one embodiment, one or more of $R_{a1}$, $R_{a2}$, $R_{a4}$, and $R_{a5}$ is selected from the group consisting of halo, —$CH_3$, —$CF_3$, and —$OCH_3$. In one embodiment, $R_{a1}$, $R_{a2}$, $R_{a4}$, and $R_{a5}$ are hydrogen, and $R_b$ is selected from the group consisting of halo, —$CH_3$, —$CF_3$, and —$OCH_3$. In one embodiment, $R_b$ is a halogen, e.g., fluorine, and $R_{a1}$ is a methyl. In one embodiment, $R_b$ is a fluorine or chlorine, and $R_{a2}$ is a fluorine or chlorine. In one embodiment, $R_b$ is $CF_3$. In one embodiment, $R_b$ is —$OCH_3$. In one embodiment, $R_b$ is a chlorine and $R_{a1}$ is a chlorine.

In one embodiment, compound (50) has the structure of compound (55):

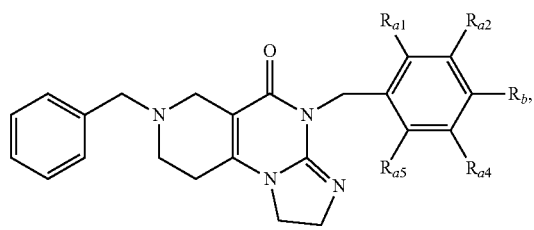

(55)

wherein $R_{a1}$, $R_{a2}$, $R_{a4}$, $R_{a5}$, and $R_b$ are as defined above. In one embodiment, $R_b$ is selected from the group consisting of halo, —CH$_3$, —CF$_3$, and —OCH$_3$. In one embodiment, one or more of $R_{a1}$, $R_{a2}$, $R_{a4}$, and $R_{a5}$ is selected from the group consisting of halo, —CH$_3$, —CF$_3$, and —OCH$_3$. In one embodiment, $R_{a1}$, $R_{a2}$, $R_{a4}$, and $R_{a5}$ are hydrogen, and $R_b$ is selected from the group consisting of halo, —CH$_3$, —CF$_3$, and —OCH$_3$. In one embodiment, $R_b$ is a halogen, e.g., fluorine, and $R_{a1}$ is a methyl. In one embodiment, $R_b$ is fluorine or chlorine, and $R_{a2}$ is a fluorine or chlorine. In one embodiment, $R_b$ is CF$_3$. In one embodiment, $R_b$ is OCH$_3$. In one embodiment, $R_b$ is a chlorine and $R_{a1}$ is a chlorine.

In one embodiment, compound (10) has the structure of compound (60)

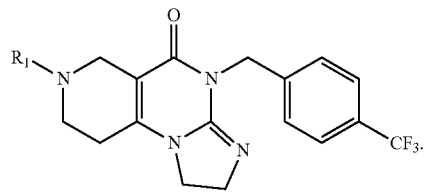

(60)

In some embodiments, $R_1$ is a hydrogen. In some embodiments, $R_1$ is a substituted or an unsubstituted arylalkyl, such as a benzyl or phenylethyl group. In some embodiments, $R_1$ is a substituted or an unsubstituted heterocycloalkylalkyl. or a substituted or an unsubstituted heteroarylalkyl, such as an CH$_2$-(2-thienyl), CH$_2$-(3-thienyl), CH$_2$-2-pyridinyl, CH$_2$-3-pyridinyl, CH$_2$-4-methyl-2-thiazolyl, CH$_2$-2-pyrazinyl, CH$_2$CH$_2$(4-N-benzyl-piperazine), CH$_2$-(3-isoxazolidinyl), and CH$_2$CH$_2$-(4-morpholinyl). In one embodiment, the arylalkyl is substituted with C$_{1-4}$alkyl, C$_{1-4}$alkoxyl, hydroxyl, perhalogenated C$_{1-4}$alkyl, or halo. In one embodiment, the benzyl is substituted with one or more halogens. In some embodiments, the benzyl is substituted with one or more substituents selected from the group consisting of halo (e.g., fluorine) —CH$_3$, —CF$_3$, and —OCH$_3$. In one embodiment, the benzyl is substituted at the para position with a substituent selected from the group consisting of halo, —CH$_3$, —CF$_3$, and —OCH$_3$. In one embodiment, $R_1$ is fluorophenyloxobutyl or hydroxyphenylethyl Scheme 3 illustrates the synthesis of compounds of formula (10):

Scheme 3

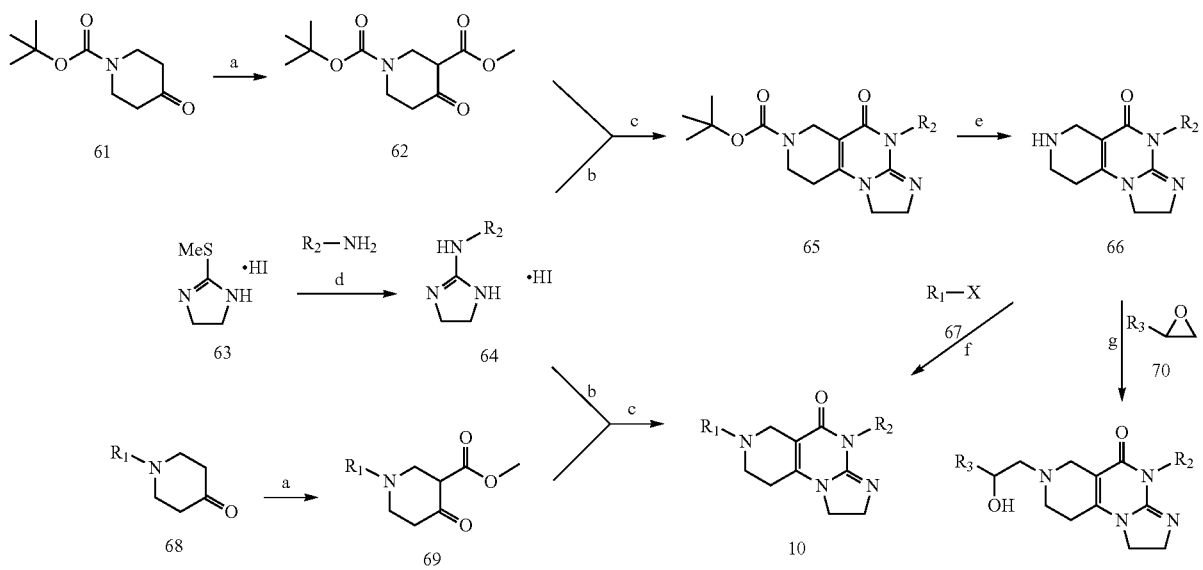

Methods: a. NaH, dimethyl carbonate, toluene, 80° C. 4 h; b. 1N NaOH/CH$_2$Cl$_2$ to convert to free base, then heat in dioxane 70° C.; c. 1-butanol/reflux 3-6 h (Dean-Stark trap) PPTS; d. dioxane 70° C.; e. HCl in dioxane -25° C.-RT to give HCl salt; f. Na$_2$CO$_3$, DIEA 80° C.; g. NaOH/CH$_2$Cl$_2$ to make free base, then MeOH reflux, 3.5 h Compounds of formula (10) are synthesized starting from a substituted piperidone, which is converted by reaction with a substituted aminoimidazoline to give the core compound (10). There are two routes, one in which the $R_1$ substituent is present in the piperidone (e.g., 68). In that route, (68) is acylated with dimethyl carbonate using sodium hydride in toluene at 80° C. to form piperidone ester (69). Commercially available methylthioimidazoline HI salt (63) is reacted with an amine in dioxane at 70° C. to afford the $R_2$-substituted aminoimidazoline (64) as its HI salt. Direct reaction of (64) with piperidone ester (69) in 1-butanol at reflux with removal of water via a Dean-Stark trap over 3-6 h gives the tricylic compound (10). In a variant of this scheme, N—BOC protected piperidone (61) is converted by the same methods to BOC protected compound (65), which is treated with HCl in dioxane to remove the BOC group and then converted to the free base of (66) with 1N NaOH with extraction with methylene chloride. Subsequent treatment of (66) with a halide (67) or epoxide (70) affords desired compound (10).

The crude products may be purified by column chromatography eluting with methylene chloride:methanol or by HPLC using acetonitrile:TFA:$H_2O$ to produce the final products as either free bases or as TFA salts. Treatment of the free bases with HCl in dioxane or lyophilization of the TFA salts generates the products (10) as HCl or TFA salts. Alternatively, the free base may be treated with another inorganic or organic acid to form other salts, generally selected from those known to be pharmaceutically acceptable salts. The salts of compound (10) are usually solids and examples have been crystallized from ethanol or other solvents to give high quality crystals. The tricyclic structure has been definitively confirmed in the case of compound (1) by an X-ray crystal structure and NMR.

Compound described herein can be used, with or without an aminoalkyl linker (e.g., compound (33)), to identify molecules (e.g., proteins) that interact with them in a cellular context. The expression of these binding targets may be used to predict response to compound (1) (ONC201) or its analogs (i.e. serve as biomarkers). In addition, these compounds can be used to screen for structurally unrelated anti-cancer compounds using competition assays known in the art to identify drugs able to outcompete the target interaction with a higher affinity. In addition, these molecules may have drug properties that create therapeutic improvements or allow additional therapeutic applications by altering drug properties including but not limited to pharmacokinetics, potency, safety, biodistribution, or metabolism.

EXAMPLE OF COMPOUND (10)

| No. | ONC Number | $R_1$ | $R_2$ |
|---|---|---|---|
| 1 | ONC201 | $CH_2Ph$ | $CH_2$-((2-$CH_3$)—Ph) |
| 13 |  | $CH_2Ph$ | $CH_3$ |
| 14 | ONC902 | $CH_2Ph$ | $CH_2$-((2-Cl)—Ph) |
| 15 | ONC903 | $CH_2Ph$ | $CH_2$-(2-thienyl) |
| 16 | ONC904 | $CH_2Ph$ | $CH_2CH_2Ph$ |
| 17 | ONC905 | $CH_2Ph$ | $CH_2CH_2$(4-N-benzyl-piperazine) |
| 18 | ONC906 | $CH_2Ph$ | $CH_2$-(2,4-di F—Ph) |
| 19 | ONC907 | H | $CH_2$-((2-$CH_3$)—Ph) |
| 20 | ONC908 | $CH_3$ | $CH_2$-((2-$CH_3$)—Ph) |
| 21 | ONC909 | $CH_2CH_2Ph$ | $CH_2$-((2-$CH_3$)—Ph) |
| 22 |  | $CH_2CH_2$-(4-N-benzyl-piperizine) | $CH_2$-((2-$CH_3$)—Ph) |
| 23 |  | $CH_2CHOHPh$ | $CH_2$-((2-$CH_3$)—Ph) |
| 24 |  | $(CH_2)_3CO$-4F—Ph | $CH_2$-((2-$CH_3$)—Ph) |
| 32 | ONC910 | $CH_2CH_2NHCOOC(CH_3)_3$ | $CH_2$-((2-$CH_3$)—Ph) |
| 33 | ONC911 | $CH_2CH_2CH_2NH_2$ | $CH_2$-((2-$CH_3$)—Ph) |
| 41 | ONC210 | $CH_2Ph$ | $CH_2$-(3,5-di F—Ph) |
| 51 | ONC211 | $CH_2Ph$ | $CH_2$-(3,4-di Cl—Ph) |
| 52 | ONC212 | $CH_2Ph$ | $CH_2$-(4-$CF_3$—Ph) |
| 53 | ONC213 | $CH_2Ph$ | $CH_2$-(3,4-di F—Ph) |
| 54 | ONC214 | $CD_2C_6D_5$ | $CH_2$-((2-$CH_3$)—Ph) |
| 43 | ONC217 | $CH_2Ph$ | $CH_2$-(2-F—Ph) |
| 55 | ONC218 | $CH_2Ph$ | $CH_2$(2-$CH_3$, 4-F—Ph) |
| 56 | ONC219 | $CH_2Ph$ | $CH_2$-(2,4-di Cl—Ph) |
| 57 | ONC220 | $CH_2Ph$ | $CH_2$-((4-$OCH_3$)—Ph) |
| 34 | ONC226 | $CH_2Ph$ | $CH_2$-(3-pyridinyl) |
| 35 | ONC222 | $CH_2Ph$ | $CH_2$-(3-isoxazolidinyl) |
| 36 | ONC224 | $CH_2Ph$ | $CH_2CH_2$-(4-morpholinyl) |
| 37 | ONC223 | $CH_2Ph$ | $CH_2$-(4-$CH_3$—Ph) |
| 38 | ONC221 | H | $CH_2$-(4-$CF_3$—Ph) |
| 73 | ONC227 | $CH_2$-(4-$CF_3$—Ph) | $CH_2$-(4-$CF_3$—Ph) |
| 72 | ONC225 | $CH_2Ph$ | $CH_2$-(2-F, 4-$CF_3$—Ph) |
| 74 | ONC228 | $CH_2$-(4-F—Ph) | $CH_2$-(4-$CF_3$—Ph) |
| 75 | ONC229 | $CH_2$—($OCH_3$—Ph) | $CH_2$-(4-$CF_3$—Ph) |
| 76 | ONC230 | (4-F—Ph)-4-oxobutyl | $CH_2$-(4-$CF_3$—Ph) |
| 77 | ONC231 | $CH_2$-3-pyridyl | $CH_2$-(4-$CF_3$—Ph) |
| 78 | ONC232 | $CH_2$-4-methyl-2-thiazolyl | $CH_2$-(4-$CF_3$—Ph) |
| 79 | ONC233 | $CH_2$-2-pyrazinyl | $CH_2$-(4-$CF_3$—Ph) |
| 81 | ONC234 | $CH_2$-(3,4-di Cl—Ph) | $CH_2$-(4-$CF_3$—Ph) |
| 82 | ONC235 | $CH_2$-(4-Cl—Ph) | $CH_2$-(4-$CF_3$—Ph) |
| 83 | ONC236 | $CH_2$-3-thienyl | $CH_2$-(4-$CF_3$—Ph) |
| 84 | ONC237 | $CH_2CH(OH)Ph$ | $CH_2$-(4-$CF_3$—Ph) |

As described in Example 12 below, compound (1) with an aminoalkyl linker (i.e., compound (33)) was used to identify proteins that interact with compound (1). It has been found that compound (1) interacts with proteins involved with N6-methyl-adenosine (m⁶A) mRNA methylation. Proteins that are involved with m⁶A mRNA epigenetic modification include those in Table 1. These proteins include those that methylate mRNA (RNA Writers), such as METTL3, METTL14, WTAP, and KIAA1429; those that demethylate m⁶A mRNA (RNA Erasers), such as FTO and ALKBH5; as well as those that specifically recognize m⁶A RNA (RNA Readers), such as YTHDF3, YTHDF2, YTHDF1, YTHDC1, and YTHDC2.

TABLE 1 m⁶A mRNA methylation proteins

| RNA Readers |
| --- |
| YTHDF3 |
| YTHDF2 |
| YTHDF1 |
| YTHDC1 |
| YTHDC2 |
| RNA Writers |
| METTL3 |
| METTL14 |
| WTAP |
| KIAA1429 |
| RNA Erasers |
| FTO |
| ALKBH5 |

IV. ASSESSING SENSITIVITY AND EFFICACY OF TREATMENT REGIMENS

Measuring expression, post-translational modifications, or activity levels of or mutations in eIF2-alpha, ATF4, CHOP, DR5, or cleaved or total cytokeratin 18 may be used to predict response or sensitivity to a method of treatment described herein and to identify subjects likely to be responsive to a method of treatment described herein, such as treatment with compound (1), a pharmaceutically acceptable salt thereof, or an analog thereof. In addition, measuring expression, post-translational modifications, or activity levels of or mutations in eIF2-alpha, ATF4, CHOP, DR5, or cleaved or total cytokeratin 18 can be used to assess the effectiveness of or monitor a method of treatment described herein. Furthermore, measuring expression, post-translational modifications, or activity levels of or mutations in eIF2-alpha, ATF4, CHOP, DR5, or cleaved or total cytokeratin 18 can be used to screen in vivo, in vitro, or in silico for structurally unrelated anti-cancer compounds. For example, competition and other assays known in the art may be used to identify drugs able to outcompete the target interaction with a higher affinity to compare changes in those levels to the respective changes produced by compound (1) or an analog thereof. Assays can also be performed on living mammalian cells, which more closely approximate the effects of a particular serum level of drug in the body, or on microsomal extracts prepared from cultured cell lines.

In some embodiments, the subject has, or is at risk of having, cancer. In some embodiments, the treatment regimen comprises administering an effective amount of compound (1) or compound (10) or an analog thereof. In some embodiments, the treatment regimen comprises administering an effective amount of compound (1). In some embodiments, the treatment regimen comprises administering an effective amount of a compound of formula (10). In some embodiments, the compound of formula (10) is a compound of formula (40), e.g., a compound of formula (45). In some embodiments, a compound of formula (10) is a compound of formula (50), e.g., a compound formula (55). In some embodiments, the compound of formula (10) is a compound of formula (80). In some embodiments, the compound of formula (10) is a compound of formula (90). In some embodiments, the compound of formula (10) is a compound of formula (60). In some embodiments, analogs of compound (1) have a structure selected from the structures of compound (25), compound (26), compound (27), compound (28), compound (29), compound (30), or compound (31).

Levels for a pre-determined standard can be, e.g., the average or median levels measured in samples from subjects. The levels for a pre-determined standard can be measured under the same or substantially similar experimental conditions as in measuring the sample from the subject. The levels for the pre-determined standard may be obtained from subjects who are responsive to treatment with compound (1) or compound (10) or an analog thereof. In one embodiment, the pre-determined standard is obtained from subjects who are responsive to treatment with the compound, and if the levels in the sample from the subject are similar to those in the standard, then the subject can be classified as likely to be responsive to treatment. The levels for the pre-determined standard may be obtained from subjects who are not responsive to treatment with the compound. In one embodiment, the pre-determined standard is obtained from subjects who are not responsive to treatment with the compound, and if the levels in the sample from the subject are different (e.g., up- or down-regulated) than those in the pre-determined standard, then the subject can be classified as likely to be responsive to treatment. The levels for the pre-determined standard may be obtained from normal healthy subjects.

Immunoassays can be used to assay protein or methylation levels in a sample, including, but not limited to, enzyme-linked immunosorbent assay (ELISA), enzyme-linked immunofiltration assay (ELIFA), flow cytometry, immunoblot, immunoprecipitation, immunohistochemistry, immunocytochemistry, luminescent immunoassay (LIA), fluorescent immunoassay (FIA), and radioimmunoassay. m⁶A mRNA methylation levels in a sample can be obtained by methylated RNA immunoprecipitation (Me-RIP)) or other quantitative biochemical assays known in the art.

Nucleic acid mutations can be determined by any of a number of known procedures. For example, a biologic sample from an individual can first be obtained. Such biological samples include, but are not limited to, a bodily fluid (such as urine, saliva, plasma, or serum) or a tissue sample (such as a buccal tissue sample or buccal cell). The biologic sample can then be sequenced or scanned using known methods. For example, DNA arrays can be used to analyze at least a portion of the subject's genomic sequence. Furthermore, whole or partial genome sequence information can be used. Such sequences can be determined using standard sequencing methods including chain-termination (Sanger dideoxynucleotide), dye-terminator sequencing, and SOLID™ sequencing (Applied Biosystems). Whole genome sequences can be cut by restriction enzymes or sheared (mechanically) into shorter fragments for sequencing. DNA sequences can also be amplified using known methods such as PCR and vector-based cloning methods (e.g., *Escherichia coli*). In one embodiment, at least a portion of a subject's genetic material (e.g., DNA, RNA, mRNA, cDNA, other nucleotide bases or derivatives of these) is scanned or sequenced using, e.g., conventional DNA sequencers or chip-based technologies, to identify the presence or absence of mutations or copy number variations.

In one aspect, provided herein are methods of identifying and treating a subject having a condition and who is likely to be responsive to a treatment regimen described herein. In one embodiment, the method comprises (i) identifying whether a subject having a condition is likely to be responsive to a treatment regimen described herein; and (ii) treating with the treatment regimen a subject determined likely to be responsive to that treatment regimen. In one embodiment, the subject has, or is at risk of having, cancer. In one embodiment, the treatment regimen comprises administering an effective amount of compound (1) or compound (10) or an analog thereof. In some embodiments, the treatment regimen comprises administering an effective amount of compound (1). In some embodiments, the treatment regimen comprises administering an effective amount of a compound of formula (10). In some embodiments, the compound of formula (10) is a compound of formula (40), e.g., a compound of formula (45). In some embodiments, a compound of formula (10) is a compound of formula (50), e.g., a compound formula (55). In some embodiments, the compound of formula (10) is a compound of formula (80). In some embodiments, the compound of formula (10) is a compound of formula (90). In some embodiments, the compound of formula (10) is a compound of formula (60). In some embodiments, analogs of compound (1) have a structure selected from the structures of compound (25), compound (26), compound (27), compound (28), compound (29), compound (30), or compound (31).

Levels for a pre-determined standard can be, e.g., the average or median levels measured in samples from subjects. The levels for a pre-determined standard can be measured under the same or substantially similar experimental conditions as in measuring the sample from the subject. The levels for the pre-determined standard may be obtained from subjects who are responsive to treatment with compound (1) or compound (10) or an analog thereof. In one embodiment, the pre-determined standard is obtained from subjects who are responsive to treatment with the compound, and if the levels in the sample from the subject are similar to those in the standard, then the subject can be classified as likely to be responsive to treatment. The levels for the pre-determined standard may be obtained from subjects who are not responsive to treatment with the compound. In one embodiment, the pre-determined is obtained from subjects who are not responsive to treatment with the compound, and if the levels in the sample from the subject are different (e.g., up- or down-regulated) than those in the pre-determined standard, then the subject can be classified as likely to be responsive to treatment. The levels for the pre-determined standard may be obtained from normal healthy subjects Immunoassays can be used to assay protein levels in a sample.

In one aspect, provided herein are methods of treating and assessing the effectiveness of a treatment in a subject having a condition. In some embodiments, the method comprises (i) treating the subject according to a method of treatment described herein (ii) assessing as described herein the effectiveness of the treatment. In some embodiments, the subject has, or is at risk of having, cancer. In some embodiments, the treatment regimen comprises administering an effective amount of compound (1) or compound (10) or an analog thereof. In some embodiments, the treatment regimen comprises administering an effective amount of compound (1). In some embodiments, the treatment regimen comprises administering an effective amount of a compound of formula (10). In some embodiments, the compound of formula (10) is a compound of formula (40), e.g., a compound of formula (45). In some embodiments, a compound of formula (10) is a compound of formula (50), e.g., a compound formula (55). In some embodiments, the compound of formula (10) is a compound of formula (80). In some embodiments, the compound of formula (10) is a compound of formula (90). In some embodiments, the compound of formula (10) is a compound of formula (60). In some embodiments, analogs of compound (1) have a structure selected from the structures of compound (25), compound (26), compound (27), compound (28), compound (29), compound (30), or compound (31).

Other conditions that may be suitable for the methods described herein include, but are not limited to, Attention Deficit Disorder; Addiction; Epilepsy; Viral infection; Inflammation; Neurodegenerative diseases such as Alzheimer's disease, Parkinson's disease, Huntington's disease, Amyotrophic lateral sclerosis; Cardiovascular diseases such as coronary artery disease, cardiomyopathy, hypertensive heart disease, heart failure, pulmonary heart disease, cardiac dysrhythmias, inflammatory heart disease, endocarditis, inflammatory cardiomegaly, myocarditis, valvular heart disease, cerebrovascular disease, peripheral arterial disease, congenital heart disease, rheumatic heart disease; Diabetes; and light chain amyloidosis.

V. COMPOSITIONS

In one aspect, pharmaceutical compositions are provided, comprising compounds of

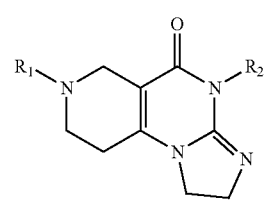

(10)

formula (10) or of formula (1):

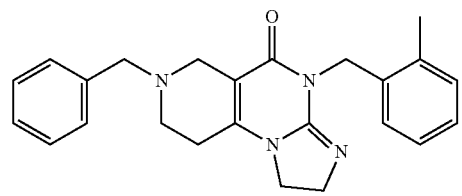

(1)

and their pharmaceutically acceptable salts. In one embodiment, the pharmaceutical composition comprises a pharmaceutically acceptable salt of the compound. In one embodiment, the salt is a pharmaceutically acceptable mono-salt of the compound. In one embodiment, the salt is a pharmaceutically acceptable di-salt of the compound. In one embodiment, the salt is a pharmaceutically acceptable mono- or multi-salt (e.g., a di-salt or tri-salt) thereof selected from the group consisting of hydrochloride, hydrobromide, hydrogensulphate, sulfates, phosphates, fumarates, succinates, oxalates and lactates, bisulfates, hydroxyl, tartrate, nitrate, citrate, bitartrate, carbonate, malate, maleate, fumarate sulfonate, methylsulfonate, formate, acetate, and carboxylate. In one embodiment In one embodiment, the salt is a pharmaceutically acceptable salt selected from the group consisting of p-toluene-sulfonate, benzenesulfonate, citrate, methanesulfonate, oxalate, succinate, tartrate, fumarate and maleate. In one embodiment, the salt is a pharmaceutically acceptable salt selected from the group consisting of ammonium, sodium, potassium, calcium, magnesium, zinc, lithium, and/or with counter-ions such as methylamino, dimethylamino, diethylamino and triethylamino counterions. In one embodiment, the salt is a. di-hydrochloride salt or a di-hydrobromide salt of the compound.

Compound (1) has the same chemical structure that would be revealed by structural analysis (e.g., NMR, X-ray diffraction) of compound NSC 350625, available from the National Cancer Institute's Developmental Therapeutics Program Repository.

In one embodiment, the pharmaceutical composition includes a di-salt (e.g., a di-hydrochloride salt) of compound (1) or an analog thereof (e.g., a compound of formula (10)). Salts (e.g., di-salts or tri-salts) of an analog of compound (1) can be prepared from an analog of compound (1), which can be synthesized as described herein, or using standard chemical synthetic methodology known to one of ordinary skill in the art.

In one embodiment, the pharmaceutical composition includes at least one pharmaceutically acceptable carrier. Suitable pharmaceutically acceptable carriers, include, but are not limited to, those found in Handbook of Pharmaceutical Excipients, 7$^{th}$ edition, edited by Raymond C. Rowe et al., American Pharmaceutical Association, Washington, USA and Pharmaceutical Press, London; and earlier editions. Exemplary pharmaceutically acceptable carriers, methods for making pharmaceutical compositions and various dosage forms, as well as modes of administration are well-known in the art, for example as detailed in Pharmaceutical Dosage Forms: Tablets, edited by Larry L. Augsburger & Stephen W. Hoag., London: Informa Healthcare, 2008; and in L. V. Allen, Jr. et al., Ansel's Pharmaceutical Dosage Forms and Drug Delivery Systems, 8th Ed., Philadelphia, Pa.: Lippincott, Williams & Wilkins, 2004; A. R. Gennaro, Remington: The Science and Practice of Pharmacy, Lippincott Williams & Wilkins, 21st ed., 2005, particularly chapter 89; and J. G. Hardman et al., Goodman & Gilman's The Pharmacological Basis of Therapeutics, McGraw-Hill Professional, 10th ed., 2001.

In one embodiment, the pharmaceutical composition is formulated for ocular administration. In one embodiment, pharmaceutical compositions are formulated for topical administration. In one embodiment, the pharmaceutical compositions are formulated as drops, ointments, or liquids. In one embodiment, pharmaceutical compositions include conventional pharmaceutical carriers such as aqueous, powdery or oily bases, thickeners or the like.

In some embodiments, the pharmaceutical composition is a formulation for intravenous administration. In one embodiment, the intravenous formulation comprises a compound of formula (10), or a pharmaceutically acceptable salt thereof dissolved in a solvent. In one embodiment, the solvent comprises water. In one embodiment, the intravenous formulation includes the compound or its salt in a concentration of about 0.05, about 0.25, about 0.5, about 2.5, about 5, about 25, or about 50 mg/mL. In one embodiment, the intravenous formulation includes the compound or its salt in a concentration of from about 0.05, 0.5, or 5 mg/mL to about 1, 10, or 100 mg/mL. In one embodiment, the intravenous formulation includes from about 0.005% 0.05%, or 0.5% to about 0.1%, 1%, or 10% of the compound or its salt. In one embodiment, the intravenous formulation includes about 0.05%, 0.5%, or 5% of the compound or its salt. In some embodiments, the intravenous formulation includes a higher or a lower concentration of the compound or its salt.

In some embodiments, the intravenous formulation has pH of about 3. In one embodiment, the intravenous formulation is adjusted to pH 3 with a phosphate buffer. In one embodiment, the intravenous formulation includes dextrose or sodium chloride. In one embodiment, the intravenous formulation including the compound or its salt in a concentration of about 5 mg/mL and pH 3 and forms a stable solution. In one embodiment, the intravenous formulation includes the compound or its salt in a concentration of about 5 mg/mL and pH<5 and forms a stable solution. In one embodiment, the intravenous formulation includes the compound or its salt and one or more antioxidants. In one embodiment, the intravenous formulation includes a mixture of mono- and di-hydrochloride salt of the compound. In one embodiment, the intravenous formulation includes the compound or its salt as a 1% solution in a concentration of about 10 mg/mL. For example, the intravenous formulation is a solution having a pH of about 3.3. In one embodiment, the pH is less than 4.0.

In one embodiment, the pharmaceutical composition further includes a pharmaceutically acceptable carrier. In one embodiment, a suitable pharmaceutically acceptable carrier includes an oil. In one embodiment, a suitable pharmaceutically acceptable carrier includes sterile water. In one embodiment, a suitable pharmaceutically acceptable carrier includes an aqueous carrier. In some embodiments, the intravenous formulation includes dextrose and/or sodium.

In one embodiment, the intravenous formulation comprises compound (1) or an analog thereof or a di-hydrochloride salt thereof dissolved in water at 25 mg/mL. In one embodiment, the intravenous formulation is adjusted to pH 3 with phosphate buffer. In one embodiment, the intravenous formulation includes dextrose or sodium chloride. In one embodiment, the intravenous formulation includes a higher or a lower concentration of the di-hydrochloride salt of compound (1) or an analog thereof. In one embodiment, the intravenous formulation includes compound (1) or an analog thereof or a di-hydrochloride salt thereof in a concentration of about 5 mg/mL. In one embodiment, the intravenous formulation includes compound (1) or an analog thereof or a di-hydrochloride salt thereof in a concentration of about 5 mg/mL and pH 3 forms a stable solution. In one embodiment, the intravenous formulation includes compound (1) or an analog thereof or a di-hydrochloride salt thereof in a concentration of about 5 mg/mL and pH<5 and forms a stable solution. In one embodiment, the intravenous formulation includes compound (1) or an analog thereof or a di-hydrochloride salt thereof and one or more antioxidants. In one embodiment, the intravenous formulation includes a mixture of mono- and di-hydrochloride salt of compound (1) or an analog thereof. In one embodiment, the intravenous formulation includes compound (1) or an analog thereof or a di-hydrochloride salt thereof as a 1% solution in a concentration of about 10 mg/mL. For example, the intravenous formulation is a solution having a pH of about 3.3. In one embodiment, the pH is less than 4.0.

In one embodiment, the intravenous formulation includes from about 0.5% to about 10% (or from about 5 mg/mL to about 100 mg/mL) of compound (1) or an analog thereof or a di-salt thereof. In one embodiment, the intravenous formulation includes from about 5% (or about 50 mg/mL) of compound (1) or an analog thereof or a di-salt thereof. In one embodiment, the intravenous infusion rate may be slowed to decrease side effects of compound (1) or an analog thereof or a di-salt thereof.

In one embodiment, the pharmaceutical composition comprises about 0.1-99% of a salt of compound (1) or an analog thereof; and a pharmaceutically acceptable carrier, e.g., an oil or a sterile water or other aqueous carriers. In one embodiment, the pharmaceutical composition comprises a mono or di-salt of compound (1) or an analog thereof in a range of from about 5% to about 50% for oral dosage forms.

In some embodiments, the pharmaceutical composition includes an antioxidant. Suitable antioxidants include: ascorbic acid derivatives such as ascorbic acid, erythorbic acid, sodium ascorbate, thiol derivatives such as thioglycerol, cysteine, acetylcysteine, cystine, dithioerythreitol, dithiothreitol, glutathione, tocopherols, butylated hydroxyanisole (BHA), butylated hydroxytoluene (BHT), sulfurous acid salts such as sodium sulfate, sodium bisulfite, acetone sodium bisulfite, sodium metabisulfite, sodium sulfite, sodium formaldehyde sulfoxylate, and sodium thiosulfate, nordihydroguaiaretic acid. It should be noted that antioxidants used for aqueous formulations typically include: sodium sulphite, sodium metabisulphite, sodium formaldehyde sulphoxylate and ascorbic acid and combinations thereof, whereas antioxidants used in oil-based solutions, organic solvents, include butylated hydroxytoluene (BHT), butylated hydroxyanisole (BHA) and propyl gallate and combinations thereof. In yet other embodiments, an antioxidant can be one or more of a flavanoid, an isoflavone, monothioglycerol, L-cysteine, thioglycolic acid, α-tocopherol, ascorbic acid 6-palmitate, dihydrolipoic acid, butylated hydroxytoluene (BHT), butylated hydroxyanisole (BHA), vitamin E, propyl gallate, β-carotene, ascorbic acid. Antioxidants can typically be used in about 0.1% to 1.0% by weight, more typically about 0.2%.

In one embodiment, the pharmaceutical composition includes compound (1) or compound (10) or an analog thereof or a pharmaceutically acceptable salt thereof and at least one other therapeutic agent. For example, the other therapeutic agent is selected from the group consisting of hormone analogs and antihormones, aromatase inhibitors, LHRH agonists and antagonists, inhibitors of growth factors, growth factor antibodies, growth factor receptor antibodies, tyrosine kinase inhibitors; antimetabolites; antitumour antibiotics; platinum derivatives; alkylation agents; antimitotic agents; tubuline inhibitors; PARP inhibitors, topoisomerase inhibitors, serine/threonine kinase inhibitors, tyrosine kinase inhibitors, protein protein interaction inhibitors, RAF inhibitors, MEK inhibitors, ERK inhibitors, IGF-1R inhibitors, ErbB receptor inhibitors, rapamycin analogs, BTK inhibitors, CRM1 inhibitors (e.g., KPT185), P53 modulators (e.g., Nutlins), antiangiogenics (e.g., axitinib, aflibercept, sorafenib, and regorafenib), amifostin, anagrelid, clodronat, filgrastin, interferon, interferon alpha, leucovorin, rituximab, procarbazine, levamisole, mesna, mitotane, pamidronate and porfimer, 2-chlorodesoxyadenosine, 2-fluorodesoxy-cytidine, 2-methoxyoestradiol, 2C4,3-alethine, 131-1-TM-601, 3CPA, 7-ethyl-10-hydroxycamptothecin, 16-aza-epothilone B, A 105972, A 204197, abiraterone, aldesleukin, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, AMG-479 (ganitumab), ARRY 162, ARRY 438162, ARRY-300, ARRY-142886/AZD-6244 (selumetinib), ARRY-704/AZD-8330, AR-12, AR-42, AS-703988, AXL-1717, AZD-8055, AZD-5363, AZD-6244, ARQ-736, ARQ 680, AS-703026 (primasertib), avastin, AZD-2014, azacytidine, azaepothilone B, azonafide, BAY-43-9006, BAY 80-6946, BBR-3464, BBR-3576, bevacizumab, BEZ-235, biricodar dicitrate, BCX-1777, BKM-120, bleocin, BLP-25, BMS-184476, BMS-247550, BMS-188797, BMS-275291, BMS-663513, BMS-754807, BNP-1350, BNP-7787, BIBW 2992 (afatinib, tomtovok), BIBF 1120 (vargatef), BI 836845, BI 2536, BI 6727, BI 836845, BI 847325, BI 853520, BUB-022, bleomycinic acid, bleomycin A, bleomycin B, brivanib, bryostatin-1, bortezomib, brostallicin, busulphan, BYL-719, CA-4 prodrug, CA-4, CapCell, calcitriol, canertinib, canfosfamide, capecitabine, carboxyphthalatoplatin, CCI-779, CC-115, CC-223, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, CKI-27, clofarabin, colchicin, combretastatin A4, COT inhibitors, CHS-828, CH-5132799, CLL-Thera, CMT-3 cryptophycin 52, CTP-37, CTLA-4 monoclonal antibodies, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, E7010, E-6201, edatrexat, edotreotide, efaproxiral, eflornithine, EGFR inhibitors, EKB-569, EKB-509, enzastaurin, enzalutamide, elsamitrucin, epothilone B, epratuzumab, ER-86526, erlotinib, ET-18-0CH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fotemustine, galarubicin, gallium maltolate, gefinitib, gemtuzumab, gimatecan, glufosfamide, GCS-100, GDC-0623, GDC-0941 (pictrelisib), GDC-0980, GDC-0032, GDC-0068, GDC-0349, GDC-0879, G17DT immunogen, GMK, GPX-100, gp100-peptide vaccines, GSK-5126766, GSK-690693, GSK-1120212 (trametinib), GSK-2118436 (dabrafenib), GSK-2126458, GSK-2132231A, GSK-2334470, GSK-2110183, GSK-2141795, GW2016, granisetron, herceptine, hexamethylmelamine, histamine, homoharringtonine, hyaluronic acid, hydroxyurea, hydroxyprogesterone caproate, ibandronate, ibrutinib, ibritumomab, idatrexate, idenestrol, IDN-5109, IGF-1R inhibitors, IMC-1C11, IMC-A42 (cixutumumab), immunol, indisulam, interferon alpha-2a, interferon alpha-2b, pegylated interferon alpha-2b, interleukin-2, INK-1117, INK-128, INSM-18, ionafarnib, ipilimumab, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, KW-2450, lobaplatin, leflunomide, lenograstim, leuprolide, leuporelin, lexidronam, LGD-1550, linezolid, lutetium texaphyrin, lometrexol, losoxantrone, LU 223651, lurtotecan, LY-S6AKT1, LY-2780301, mafosfamide, marimastat, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, motexaf in gadolinium, MS-209, MS-275, MX6, neridronate, neratinib, Nexavar, neovastat, nilotinib, nimesulide, nitroglycerin, nolatrexed, norelin, N-acetylcysteine, 06-benzylguanine, oblimersen, omeprazole, oncophage, oncoVEXGM-CSF, ormiplatin, ortataxel, OX44 antibodies, OSI-027, OSI-906 (linsitinib), 4-1BB antibodies, oxantrazole, oestrogen, panitumumab, patupilone, pegfilgrastim, PCK-3145, pegfilgrastim, PBI-1402, PBI-05204, PD0325901, PD-1 antibodies, PEG-paclitaxel, albumin-stabilized paclitaxel, PEP-005, PF-05197281, PF-05212384, PF-04691502, PHT-427, P-04, PKC412, P54, PI-88, pelitinib, pemetrexed, pentrix, perifosine, perillylalcohol, pertuzumab, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, R115777, RAF-265, ramosetron, ranpirnase, RDEA-119/BAY 869766, RDEA-436, rebeccamycin analogs, receptor tyrosine kinase (RTK) inhibitors, regorafenib, revimid, RG-7167, RG-7304, RG-7421, RG-7321, RG 7440, rhizoxin, rhu-MAb, rinfabate, risedronate, rituximab, robatumumab, rofecoxib, RO-31-7453, RO-5126766, RO-5068760, RPR 109881A, rubidazone, rubitecan, R-flurbiprofen, RX-0201, S-9788, sabarubicin, SAHA, sargramostim, satraplatin, SB 408075, Se-015/Ve-015, SU5416, SU6668, SDX-101, semustin, seocalcitol, SM-11355, SN-38, SN-4071, SR-27897, SR-31747, SR-13668, SRL-172, sorafenib, spiroplatin, squalamine, suberanilohydroxamic acid, sutent, T 900607, T 138067, TAK-733, TAS-103, tacedinaline, talaporf in, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valrubicin, vatalanib, vincristine, vinflunine, virulizin, WX-UK1, WX-554, vectibix, xeloda, XELOX, XL-147, XL-228, XL-281, XL-518R-7420/GDC-0973, XL-765, YM-511, YM-598, ZD-4190, ZD-6474, ZD-4054, ZD-0473, ZD-6126, ZD-9331, ZD1839, ZSTK-474, zoledronat, zosuquidar, and combinations thereof.

In one embodiment, the other therapeutic agent comprises a hormone analog, an antihormone or both selected from the group consisting of tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxy-progesterone, octreotide, and combinations thereof. In one embodiment, the other therapeutic agent comprises one or more LHRH agonists and/or antagonists selected from the group consisting of goserelin acetate, luprolide acetate, triptorelin pamoate and combinations thereof and wherein the LHRH antagonists are selected from the group consisting of Degarelix, Cetrorelix, Abarelix, Ozarelix, Degarelix combinations thereof. In one embodiment, the other therapeutic agent comprises one or more growth factor inhibitors selected from the group consisting of inhibitors of: platelet derived growth factor (PDGF), fibroblast growth factor (FGF), vascular endothelial growth factor (VEGF), epidermal growth factor (EGF), insuline-like growth factors (IGF), human epidermal growth factor (HER) and hepatocyte growth factor (HGF). In one embodiment, the other therapeutic agent comprises one or more inhibitors of the human epidermal growth factor selected from the group consisting of HER2, HER3, and HER4. In one embodiment, the other therapeutic agent comprises one or more tyrosine kinase inhibitors selected from the group consisting of cetuximab, gefitinib, imatinib, lapatinib and trastuzumab, and combinations thereof. In one embodiment, the other therapeutic agent comprises one or more aromatase inhibitors selected from the group consisting of anastrozole, letrozole, liarozole, vorozole, exemestane, atamestane, and combinations thereof. In one embodiment, the other therapeutic agent comprises one or more antimetabolites which are antifolates selected from the group consisting of methotrexate, raltitrexed, and pyrimidine analogs. In one embodiment, the other therapeutic agent comprises one or more antimetabolites which are pyrimidine analogs selected from the group consisting of 5-fluorouracil, capecitabin and gemcitabin. In one embodiment, the other therapeutic agent comprises one or more antimetabolites which are purine and/or adenosine analogs selected from the group consisting of mercaptopurine, thioguanine, cladribine and pentostatin, cytarabine, fludarabine, and combinations thereof. In one embodiment, the other therapeutic agent comprises one or more antitumour antibiotics selected from the group consisting of anthracyclins, doxorubicin, daunorubicin, epirubicin and idarubicin, mitomycin-C, bleomycin, dactinomycin, plicamycin, streptozocin and combinations thereof. In one embodiment, the other therapeutic agent comprises one or more platinum derivatives selected from the group consisting of cisplatin, oxaliplatin, carboplatin and combinations thereof. In one embodiment, the other therapeutic agent comprises one or more alkylation agents selected from the group consisting of estramustin, meclorethamine, melphalan, chlorambucil, busulphan, dacarbazin, cyclophosphamide, ifosfamide, temozolomide, nitrosoureas, and combinations thereof. In one embodiment, the other therapeutic agent comprises nitrosoureas selected from the group consisting of carmustin, lomustin, thiotepa, and combinations thereof. In one embodiment, the other therapeutic agent comprises antimitotic agents selected from the group consisting of Vinca alkaloids and taxanes. In one embodiment, the other therapeutic agent comprises one or more taxanes selected from the group consisting of paclitaxel, docetaxel, and combinations thereof. In one embodiment, the other therapeutic agent comprises one or more Vinca alkaloids selected from the group consisting of vinblastine, vindesin, vinorelbin, vincristine, and combinations thereof. In one embodiment, the other therapeutic agent comprises one or more topoisomerase inhibitors which are epipodophyllotoxins. In one embodiment, the other therapeutic agent comprises one or more epipodophyllotoxins selected from the group consisting of etoposide and etopophos, teniposide, amsacrin, topotecan, irinotecan, mitoxantron, and combinations thereof. In one embodiment, the other therapeutic agent comprises one or more serine/threonine kinase inhibitors selected from the group consisting of PDK 1 inhibitors, B-Raf inhibitors, mTOR inhibitors, mTORC1 inhibitors, PI3K inhibitors, dual mTOR/PI3K inhibitors, STK 33 inhibitors, AKT inhibitors, PLK 1 inhibitors, inhibitors of CDKs, Aurora kinase inhibitors, and combinations thereof. In one embodiment, the other therapeutic agent comprises one or more tyrosine kinase inhibitors which are PTK2/FAK inhibitors. In one embodiment, the other therapeutic agent comprises one or more protein protein interaction inhibitors selected from the group consisting of IAP, Mcl-1, MDM2/MDMX and combinations thereof. In one embodiment, the other therapeutic agent comprises one or more rapamycin analogs selected from the group consisting of everolimus, temsirolimus, ridaforolimus, sirolimus, and combinations thereof. In one embodiment, the other therapeutic agent comprises one or more therapeutic agents selected from the group consisting of amifostin, anagrelid, clodronat, filgrastin, interferon, interferon alpha, leucovorin, rituximab, procarbazine, levamisole, mesna, mitotane, pamidronate and porfimer, and combinations thereof. In one embodiment, the other therapeutic agent comprises one or more therapeutic agents selected from the group consisting of 2-chlorodesoxyadenosine, 2-fluorodesoxy-cytidine, 2-methoxyoestradiol, 2C4,3-alethine, 131-1-TM-601, 3CPA, 7-ethyl-10-hydroxycamptothecin, 16-aza-epothilone B, A 105972, A 204197, abiraterone, aldesleukin, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, AMG-479 (ganitumab), ARRY 162, ARRY 438162, ARRY-300, ARRY-142886/AZD-6244 (selumetinib), ARRY-704/AZD-8330, AR-12, AR-42, AS-703988, AXL-1717, AZD-8055, AZD-5363, AZD-6244, ARQ-736, ARQ 680, AS-703026 (primasertib), avastin, AZD-2014, azacytidine, azaepothilone B, azonafide, BAY-43-9006, BAY 80-6946, BBR-3464, BBR-3576, bevacizumab, BEZ-235, biricodar dicitrate, BCX-1777, BKM-120, bleocin, BLP-25, BMS-184476, BMS-247550, BMS-188797, BMS-275291, BMS-663513, BMS-754807, BNP-1350, BNP-7787, BIBW 2992 (afatinib, tomtovok), BIBF 1120 (vargatef), BI 836845, BI 2536, BI 6727, BI 836845, BI 847325, BI 853520, BUB-022, bleomycinic acid, bleomycin A, bleomycin B, brivanib, bryostatin-1, bortezomib, brostallicin, busulphan, BYL-719, CA-4 prodrug, CA-4, CapCell, calcitriol, canertinib, canfosfamide, capecitabine, carboxyphthalatoplatin, CCI-779, CC-115, CC-223, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, CKI-27, clofarabin, colchicin, combretastatin A4, COT inhibitors, CHS-828, CH-5132799, CLL-Thera, CMT-3 cryptophycin 52, CTP-37, CTLA-4 monoclonal antibodies, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, E7010, E-6201, edatrexat, edotreotide, efaproxiral, eflornithine, EGFR inhibitors, EKB-569, EKB-509, enzastaurin, enzalutamide, elsamitrucin, epothilone B, epratuzumab, ER-86526, erlotinib, ET-18-0CH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fotemustine, galarubicin, gallium maltolate, gefinitib, gemtuzumab, gimatecan, glufosfamide, GCS-100, GDC-0623, GDC-0941 (pictrelisib), GDC-0980, GDC-0032, GDC-0068, GDC-0349, GDC-0879, G17DT immunogen, GMK, GPX-100, gp100-peptide vaccines, GSK-5126766, GSK-690693, GSK-1120212 (trametinib), GSK-2118436 (dabrafenib), GSK-2126458, GSK-2132231A, GSK-2334470, GSK-2110183, GSK-2141795, GW2016, granisetron, herceptine, hexamethylmelamine, histamine, homoharringtonine, hyaluronic acid, hydroxyurea, hydroxyprogesterone caproate, ibandronate, ibrutinib, ibritumomab, idatrexate, idenestrol, IDN-5109, IGF-1R inhibitors, IMC-1C11, IMC-A12 (cixutumumab), immunol, indisulam, interferon alpha-2a, interferon alpha-2b, pegylated interferon alpha-2b, interleukin-2, INK-1117, INK-128, INSM-18, ionafarnib, ipilimumab, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, KW-2450, lobaplatin, leflunomide, lenograstim, leuprolide, leuporelin, lexidronam, LGD-1550, linezolid, lutetium texaphyrin, lometrexol, losoxantrone, LU 223651, lurtotecan, LY-S6AKT1, LY-2780301, mafosfamide, marimastat, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, motexafin gadolinium, MS-209, MS-275, MX6, neridronate, neratinib, Nexavar, neovastat, nilotinib, nimesulide, nitroglycerin, nolatrexed, norelin, N-acetylcysteine, 06-benzylguanine, oblimersen, omeprazole, oncophage, oncoVEXGM-CSF, ormiplatin, ortataxel, OX44 antibodies, OSI-027, OSI-906 (linsitinib), 4-1BB antibodies, oxantrazole, oestrogen, panitumumab, patupilone, pegfilgrastim, PCK-3145, pegfilgrastim, PBI-1402, PBI-05204, PD0325901, PD-1 antibodies, PEG-paclitaxel, albumin-stabilized paclitaxel, PEP-005, PF-05197281, PF-05212384, PF-04691502, PHT-427, P-04, PKC412, P54, PI-88, pelitinib, pemetrexed, pentrix, perifosine, perillylalcohol, pertuzumab, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, R115777, RAF-265, ramosetron, ranpirnase, RDEA-119/BAY 869766, RDEA-436, rebeccamycin analogs, receptor tyrosine kinase (RTK) inhibitors, revimid, RG-7167, RG-7304, RG-7421, RG-7321, RG 7440, rhizoxin, rhu-MAb, rinfabate, risedronate, rituximab, robatumumab, rofecoxib, RO-31-7453, RO-5126766, RO-5068760, RPR 109881A, rubidazone, rubitecan, R-flurbiprofen, RX-0201, S-9788, sabarubicin, SAHA, sargramostim, satraplatin, SB 408075, Se-015/Ve-015, SU5416, SU6668, SDX-101, semustin, seocalcitol, SM-11355, SN-38, SN-4071, SR-27897, SR-31747, SR-13668, SRL-172, sorafenib, spiroplatin, squalamine, suberanilohydroxamic acid, sutent, T 900607, T 138067, TAK-733, TAS-103, tacedinaline, talaporf in, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valrubicin, vatalanib, vincristine, vinflunine, virulizin, WX-UK1, WX-554, vectibix, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZD1839, ZSTK-474, zoledronat, zosuquidar, and combinations thereof.

In one embodiment, the other therapeutic agent comprises a steroid. Steroids include, but are not limited to, dexamethasone, prednisolone, methyl prednisolone, prednisone, hydrocortisone, triamcinolone, betamethasone, and cortivazol. In one embodiment, the other therapeutic agent comprises an anti-emetic. Anti-emetics include, but are not limited to, 5-HT3 receptor agonists (e.g., dolasetron, granisetron, ondansetron, tropisetron, palonosetron, and mirtazapine), dopamine agonists (e.g., domperidone, olanzapine, droperidol, haloperidol, chlorpromazine, prochlorperazine, alizapride, prochlorperazine, and metoclopramide), NK1 receptor antagonists (e.g., aprepitant and casopitant), antihistamines (such as cyclizine, diphenhydramine, dimenhydrinate, doxylamine, meclizine, promethazine, hydroxyzine), cannabinoids (e.g., cannabis, dronabinol, nabilone, and sativex), benzodiazepines (e.g., midazolam and lorazepam), anticholinergics (e.g., hyoscine), trimethobenzamide, ginger, emetrol, propofol, peppermint, muscimol, and ajwain.

In some embodiments, the other therapeutic agent comprises an anti-cancer agent, which includes a mitotic inhibitor. In one embodiment, the mitotic inhibitor includes a taxane. In one embodiment, the mitotic inhibitor includes a taxane selected from the group consisting of paclitaxel and docetaxel.

In one embodiment, the pharmaceutical composition includes compound (1) or compound (10) or an analog thereof, or a pharmaceutically acceptable salt thereof; and at least one anti-cancer agent, which includes, without limitation, one or more of acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bevacizumab, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflomithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, zorubicin and combinations thereof.

Examples of suitable anti-cancer agents include, but are not limited to, those described Goodman and Gilman's The Pharmacological Basis of Therapeutics, 12$^{th}$ Ed., edited by Laurence Brunton, Bruce Chabner, Bjorn Knollman, McGraw Hill Professional, 2010.

In some exemplary embodiments, the pharmaceutical composition includes a salt (e.g., a mono- or di-salt) of compound (1) or compound (10) or an analog thereof and at least one other therapeutic agent, wherein the other therapeutic agent comprises an anti-angiogenic agent. For example, the anti-angiogenic agent is bevacizumab. In one embodiment, the anti-angiogenic agent is selected from the group consisting of aflibercept, axitinib, angiostatin, endostatin, 16 kDa prolactin fragment, laminin peptides, fibronectin peptides, tissue metalloproteinase inhibitors (TIMP 1, 2, 3, 4), plasminogen activator inhibitors (PAI-1, -2), tumor necrosis factor α, (high dose, invitro), TGF-β1, interferons (IFN-α, -β, γ), ELR-CXC chemokines, IL-12; SDF-1; MIG; platelet factor 4 (PF-4); IP-10, thrombospondin (TSP), SPARC, 2-methoxyoestradiol, proliferin-related protein, suramin, sorafenib, regorafenib, thalidomide, cortisone, linomide, fumagillin (AGM-1470; TNP-470), tamoxifen, retinoids, CM101, dexamethasone, leukemia inhibitoryfactor (LIF), hedgehog inhibitor and combinations thereof.

A pharmaceutical combination can include first and second therapeutic agents in any desired proportions provided that the synergistic or cooperative effect still occurs. The synergistic pharmaceutical combination preferably contains the first and second therapeutic agents in a ratio of from about 1:9 to about 9:1. In one embodiment, the synergistic pharmaceutical combination contains the first and second therapeutic agents in a ratio of from about 1:8 to about 8:1, from about 1:7 to about 7:1, from about 1:6 to about 6:1, from about 1:5 to about 5:1, from about 1:4 to about 4:1, from about 1:3 to about 3:1, or from about 1:2 to about 2:1. In one embodiment, the synergistic pharmaceutical combination contains the first and second therapeutic agents in a ratio of approximately 1:1.

In one embodiment, the second therapeutic agent is selected from the group consisting of Allopurinol, Arsenic Trioxide, Azacitidine, Bortezomib, Bevacizumab, Capecitabine, Carboplatin, Celecoxib, Chlorambucil, Clofarabine, Cytarabine, Dacarbazine, Daunorubicin HCl, Docetaxel, Doxorubicin HCl, Floxuridine, Gemcitabine HCl, Hydroxyurea, Ifosfamide, Imatinib Mesylate, Ixabepilone, Lenalidomide, Megestrol acetate, Methotrexate, Mitotane, Mitoxantrone HCl, Oxaliplatin, Paclitaxel, Pralatrexate, Romidepsin, Sorafenib, Streptozocin, Tamoxifen Citrate, Topotecan HCl, Tretinoin, Vandetanib, Vismodegib, Vorinostat, and combinations thereof.

In one embodiment, the second therapeutic agent comprises a small molecule multi-kinase inhibitor, e.g., sorafenib or regorafenib. In one embodiment, the second therapeutic agent comprises a Hedgehog Pathway Inhibitor, e.g., vismodegib. In one embodiment, the second therapeutic agent includes drugs selected from Table 2 below.

TABLE 2

Classes Of Drugs

| Classes of drugs | Examples |
| --- | --- |
| Purine analogs | allopurinol, oxypurinol, clofarabine, and tisopurine |
| Pyrimidine analogs | 5-fluorouracil, Floxuridine (FUDR), capecitabine, cytarabine, 6-azauracil (6-AU), and gemcitabine (Gemzar) |

TABLE 2-continued

Classes Of Drugs

| Classes of drugs | Examples |
| --- | --- |
| Proteasome inhibitors | bortezomib, carfilzomib, cediranib, disulfiram, epigallocatechin-3-gallate, salinosporamide A, ONCX 0912, CEP-18770, MLN9708, epoxomicin, and MG132. |
| Anti-angiogenic | bevacizumab, aflibercept, sunitinib, sorafenib, pazopanib, vandetanib, cabozantinib, axitinib, ponatinib, regorafenib, ranibizumab, lapatinib, and vandetanib. |
| Platinum-based antineoplastic drugs | cisplatin, carboplatin, oxaliplatin, satraplatin, picoplatin, nedaplatin, and triplatin. |
| COX-2 inhibitors | celecoxib, valdecoxib (Bextra), parecoxib (Dynastat), lumiracoxib, etoricoxib, and rofecoxib. |
| Nitrogen mustards | cyclophosphamide, chlorambucil, uramustine, ifosfamide, melphalan, bendamustine, and mustine. |
| Alkylating agents | cyclophosphamide, mechlorethamine or mustine (HN2) (trade name Mustardgen), uramustine or uracil mustard, melphalan, chlorambucil, ifosfamide, bendamustine, carmustine, lomustine, streptozocin, and busulfan. |
| Anthracyclines | Daunorubicin (Daunomycin), Daunorubicin (liposomal), Doxorubicin (Adriamycin), Doxorubicin (liposomal), Epirubicin, Idarubicin, Valrubicin, and Mitoxantrone. |
| Taxanes | Paclitaxel (Taxol), Docetaxel (Taxotere), and albumin-bound paclitaxel (Abraxane). |
| Nucleotide synthesis inhibitor | methotrexate, pralatrexate, hydroxyurea, and 5-fluorodeoxyuridine, 3,4-dihydroxybenzylamine. |
| Bcr-abl inhibitors | imatinib, nilotinib, dasatinib, bosutinib and ponatinib. |
| Other | arsenic trioxide, thalidomide, revlimid, and mitotane. |
| Topoisomerase inhibitor | amsacrine, etoposide, etoposide phosphate, teniposide, doxorubicin, Topotecan (Hycamtin), Irinotecan (CPT-11, Camptosar), Exatecan, Lurtotecan, ST 1481, CKD 602, ICRF-193, and genistein. |
| HDAC inhibitors | Vorinostat (SAHA), Romidepsin (Istodax), Panobinostat (LBH589), Valproic acid (as Mg valproate), Belinostat (PXD101), Mocetinostat (MGCD0103), Abexinostat (PCI-24781), Entinostat (MS-275), SB939, Resminostat (4SC-201), Givinostat, Quisinostat (JNJ-26481585), CUDC-101, AR-42, CHR-2845, CHR-3996, 4SC-202, CG200745, ACY-1215, ME-344, sulforaphane, Kevetrin, and ATRA. |
| Multi-kinase inhibitors | sorafenib, regorafenib, and vandetanib. |
| Hormone therapies | tamoxifen, toremifene, Arimidex (anastrozole), Aromasin (exemestane), Femara (letrozole), and Fulvestrant (Faslodex). |
| Hedgehog signaling Inhibitors | vismodegib, BMS-833923, IPI-926, LDE-225, PF-04449913, LEQ 506, and TAK-441. |
| Checkpoint Inhibitors | Opdivo (nivolumab), Durvalumab (Medi4736), Keytruda (pembrolizumab, MK3475), BGB-A317, AMP-224, PDR001, REGN 281, Atezolizumab (MPDL3280A), Pidilizumab (BMS-936559, CT-011, ONO-4538), Avelumab (MSB0010718 C), Yervoy (ipilimumab), tremelimumab |
| BCL2 Inhibitors | AT-101, Bcl-2/xL inhibitor, Navitoclax (ABT-263), Venetoclax (ABT-199), Apogossypol, PTN1258, obatoclax, G3139 |

In some embodiments, the second therapeutic agent includes drugs that target tumor necrosis factor-related apoptosis-inducing ligand (TRAIL) receptors. In one embodiment, the second therapeutic agent includes a recombinant TRAIL or an agonistic antibody that activates one or more TRAIL receptors. In one embodiment, the second therapeutic agent includes one or more antibodies or recombinant TRAIL that activate signaling by DR4, DR5 or both. In one embodiment, the second therapeutic agent includes one or more of AMG-655, LBY-135, mapatumumab, lexatumumab, Apomab, and rhApo2L/TRAIL. In one embodiment, the second therapeutic agent includes an active agent selected from the group consisting of Camptothecin, 5-FU, capecitabine, cisplatin, doxorubicin, irinotecan, paclitaxel, cisplatin, bortezomib, BH3I-2, rituximab, radiation, triterpenoids, sorafenib, gemcitabine, HDAC inhibitors, carboplatin, T-101 (a gossypol derivate), ABT-263, ABT-737, and GX-15-070 (obatoclax), vorinostat, cetuximab, panitumumab, bevacizumab, ganitumab, interferon gamma, sorafenib, XIAP antagonists, Bcl-2 antagonists, and Smac mimetics.

VI. DOSE

In one embodiment, a pharmaceutical composition comprises compound (1) or compound (10) or an analog thereof, or a pharmaceutically acceptable salt thereof in a dose ranging from about 40, 50, 60, or 100 mg to about 2000 mg; from about 4, 5, 6, or 10 mg to about 200 mg; or from about 0.4, 0.5, 0.6, or 1 mg to about 20 mg where the weight can be based on the compound in its free base form. In one embodiment, a pharmaceutical composition comprises compound (1) or compound (10) or an analog thereof, or a pharmaceutically acceptable salt thereof in a dose level ranging from about 50 mg to about 200, 300, 400, 500, 600, 700, 800, 900, 1000, 1100, 1200, 1300, 1400, 1500, 1600, 1700, 1800, 1900, or 2000 mg; from about 5 mg to about 20, 30, 40, 50, 60, 70, 80, 90, 100, 110, 120, 130, 140, 150, 160, 170, 180, 190, and 200 mg; or from about 0.5 mg to about 2, 3, 4, 5, 6, 7, 8, 9, 10, 11, 12, 13, 14, 15, 16, 17, 18, 19, and 20 mg. In one embodiment, a pharmaceutical composition comprises compound (1) or compound (10) or an analog thereof, or a pharmaceutically acceptable salt thereof in a dose level ranging from about 40 mg to about 200, 300, 400, 500, 600, 700, 800, 900, 1000, 1100, 1200, 1300, 1400, 1500, 1600, 1700, 1800, 1900, or 2000 mg; from about 4 mg to about 20, 30, 40, 50, 60, 70, 80, 90, 100, 110, 120, 130, 140, 150, 160, 170, 180, 190, or 200 mg; or from about 0.4 mg to about 2, 3, 4, 5, 6, 7, 8, 9, 10, 11, 12, 13, 14, 15, 16, 17, 18, 19, and 20 mg. In one embodiment, a pharmaceutical composition comprises compound (1) or compound (10) or an analog thereof, or a pharmaceutically acceptable salt thereof in a dose level ranging from about 60 mg to about 200, 300, 400, 500, 600, 700, 800, 900, 1000, 1100, 1200, 1300, 1400, 1500, 1600, 1700, 1800, 1900, or 2000 mg; from about 6 mg to about 20, 30, 40, 50, 60, 70, 80, 90, 100, 110, 120, 130, 140, 150, 160, 170, 180, 190, or 200 mg; or from about 0.6 mg to about 2, 3, 4, 5, 6, 7, 8, 9, 10, 11, 12, 13, 14, 15, 16, 17, 18, 19, or 20 mg. In one embodiment, a pharmaceutical composition comprises compound (1) or compound (10) or an analog thereof, or a pharmaceutically acceptable salt thereof in a dose level ranging from about 100 mg to about 200, 300, 400, 500, 600, 700, 800, 900, 1000, 1100, 1200, 1300, 1400, 1500, 1600, 1700, 1800, 1900 mg, or 2000 mg; from about 10 mg to about 20, 30, 40, 50, 60, 70, 80, 90, 100, 110, 120, 130, 140, 150, 160, 170, 180, 190, or 200 mg; or from about 1 mg to about 2, 3, 4, 5, 6, 7, 8, 9, 10, 11, 12, 13, 14, 15, 16, 17, 18, 19, or 20 mg. In one embodiment, a pharmaceutical composition comprises compound (1) or compound (10) or an analog thereof, or a pharmaceutically acceptable salt thereof in a dose level ranging from about 200 mg to about 300, 400, 500, 600, 700, 800, 900, 1000, 1100, 1200, 1300, 1400, 1500, 1600, 1700, 1800, 1900, or 2000 mg; from about 20 mg to about 30, 40, 50, 60, 70, 80, 90, 100, 110, 120, 130, 140, 150, 160, 170, 180, 190, or 200 mg; or from about 2 mg to about 3, 4, 5, 6, 7, 8, 9, 10, 11, 12, 13, 14, 15, 16, 17, 18, 19, or 20 mg, based on the compound in its free base form. In one embodiment, a pharmaceutical composition comprises compound (1) or compound (10) or an analog thereof, or a pharmaceutically acceptable salt thereof in a dose level ranging from about 400 mg to about 500, 600, 700, 800, 900, 1000, 1100, 1200, 1300, 1400, 1500, 1600, 1700, 1800, 1900, or 2000 mg; from about 40 mg to about 50, 60, 70, 80, 90, 100, 110, 120, 130, 140, 150, 160, 170, 180, 190, or 200 mg; or from about 4 mg to about 5, 6, 7, 8, 9, 10, 11, 12, 13, 14, 15, 16, 17, 18, 19, or 20 mg based on the compound in its free base form. In one embodiment, a pharmaceutical composition comprises compound (1) or compound (10) or an analog thereof, or a pharmaceutically acceptable salt thereof thereof in a dose level ranging from about 50 mg to about 60, 70, 80, 90, or 100 mg; from about 60 mg to about 70, 80, 90, or 100 mg; from about 70 mg to about 80, 90 or 100 mg, from about 80 mg to about 90 or 100 mg; from about 90 mg to about 100 mg; from about 5 mg to about 6, 7, 8, 9, or 10 mg; from about 6 mg to about 7, 8, 9, or 10 mg; from about 7 mg to about 8, 9 or 10 mg, from about 8 mg to about 9 or 10 mg; from about 9 mg to about 10 mg; from about 0.5 mg to about 0.6, 0.7, 0.8, 0.9, or 1 mg; from about 0.6 mg to about 0.7, 0.8, 0.9, or 1 mg; from about 0.7 mg to about 0.8, 0.9 or 1 mg, from about 0.8 mg to about 0.9 or 1 mg; or from about 0.9 mg to about 1 mg.

In one embodiment, a pharmaceutical composition comprises compound (1) or compound (10) or an analog thereof, or a pharmaceutically acceptable salt thereof in a dose ranging from about 1 mg/kg to about 40 mg/kg; 0.1 mg/kg to about 4 mg/kg; or 0.01 mg/kg to about 0.40 mg/kg. In one embodiment, a pharmaceutical composition comprises compound (1) or compound (10) or an analog thereof, or a pharmaceutically acceptable salt thereof in a dose level ranging from about 1, 2, 3, 4, 5, 6, 7, 8, or 9 mg/kg to about 10, 20, 30, or 40 mg/kg; from about 10, 11, 12, 13, 14, 15, 16, 17, 18, or 19 mg/kg to about 20, 30, or 40 mg/kg; from about 20, 21, 22, 23, 24, 25, 26, 27, 28, or 29 mg/kg to about 30 or 40 mg/kg; from about 30, 31, 32, 33, 34, 35, 36, 37, 38, or 39 mg/kg to about 40 mg/kg; from about 0.1, 0.2, 0.3, 0.4, 0.5, 0.6, 0.7, 0.8, or 0.9 mg/kg to about 1, 2, 3, or 4 mg/kg; from about 1.0, 1.1, 1.2, 1.3, 1.4, 1.5, 1.6, 1.7, 1.8, or 1.9 mg/kg to about 2, 3, or 4 mg/kg; from about 2.0, 2.1, 2.2, 2.3, 2.4, 2.5, 2.6, 2.7, 2.8, or 2.9 mg/kg to about 3 or 4 mg/kg; or from about 3.0, 3.1, 3.2, 3.3, 3.4, 3.5, 3.6, 3.7, 3.8, or 3.9 mg/kg to about 4 mg/kg; from about 0.01, 0.02, 0.03, 0.04, 0.05, 0.06, 0.07, 0.08, 0.09 mg/kg to about 0.10, 0.20, 0.30, or 0.40 mg/kg; from about 0.10, 0.11, 0.12, 0.13, 0.14, 0.15, 0.16, 0.17, 0.18, or 0.19 mg/kg to about 0.20, 0.30, or 0.40 mg/kg; from about 0.20, 0.21, 0.22, 0.23, 0.24, 0.25, 0.26, 0.27, 0.28, or 0.29 mg/kg to about 0.30 or 0.400 mg/kg; or from about 0.30, 0.31, 0.32, 0.33, 0.34, 0.35, 0.36, 0.37, 0.38, or 0.39 mg/kg to about 0.40 mg/kg.

In one embodiment, a pharmaceutical composition comprises compound (1) or compound (10) or an analog thereof, or a pharmaceutically acceptable salt thereof in a dose level ranging from about 37.5 mg/m$^2$ to about 1500 mg/m$^2$; from about 3.75 mg/m$^2$ to about 150 mg/m$^2$; or from about 0.4 mg/m$^2$ to about 15 mg/m$^2$ In one embodiment, a pharmaceutical composition comprises comprises compound (1) or compound (10) or an analog thereof, or a pharmaceutically acceptable salt thereof in a dose level ranging from about 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000, 1005, 1010, 1015, 1020, 1025, 1030, 1035, 1040, 1045, 1050, 1055, 1060, 1065, 1070, 1075, 1080, 1085, 1090, 1095, 1100, 1105, 1110, 1115, 1120, 1125, 1130, 1135, 1140, 1145, 1150, 1155, 1160, 1165, 1170, 1175, 1180, 1185, 1190, 1195, 1200, 1205, 1210, 1215, 1220, 1225, 1230, 1235, 1240, 1245, 1250, 1255, 1260, 1265, 1270, 1275, 1280, 1285, 1290, 1295, 1300, 1305, 1310, 1315, 1320, 1325, 1330, 1335, 1340, 1345, 1350, 1355, 1360, 1365, 1370, 1375, 1380, 1385, 1390, 1395, 1400, 1405, 1410, 1415, 1420, 1425, 1430, 1435, 1440, 1445, 1450, 1455, 1460, 1465, 1470, 1475, 1480, 1485, 1490, 1495 mg/m$^2$ to about 1500 mg/m$^2$; from about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 mg/m$^2$ to about 150 mg/m$^2$; or from about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 111, 11.5, 12, 12.5, 13, 13.5, 14, or 14.5 mg/m$^2$ to about 15 mg/m$^2$.

VII. DOSAGE FORMS

Suitable pharmaceutical compositions for use with the methods described herein can be formulated into a dosage form that can be administered to a patient. In one embodiment, the pharmaceutical composition is in the form of an oral dosage unit or parenteral dosage unit. In one embodiment, the pharmaceutical composition is in the form of an oral dosage unit. In some embodiments, an oral dosage unit is fractionated into several, smaller doses, which are administered to a subject over a predetermined period of time in order to reduce toxicity of the therapeutic agent being administered. In some embodiments, an oral dosage unit is administered by a tablet or capsule comprising a controlled release formulation that can include a plurality of particles, granules, pellets, minitablets or tablets. In one embodiment, the pharmaceutical composition is in the form of a parenteral dosage unit. In one embodiment, the pharmaceutical composition is in the form of a parenteral dosage unit selected from the group consisting of intravenous (IV), subcutaneous (SC), and intramuscular (M), rectal (PR) and transdermal dosage units. In one embodiment, the pharmaceutical composition is in a dosage form selected from the group consisting of sterile solutions, suspensions, suppositories, tablets and capsules. In one embodiment, the composition is an oral dosage form selected from the group consisting of a tablet, caplet, capsule, lozenge, syrup, liquid, suspension and elixir. In one embodiment, the composition is in an oral dosage form selected from the group consisting of tablets, hard shell capsules, soft gelatin capsules, beads, granules, aggregates, powders, gels, solids and semi-solids.

In some embodiments, suitable forms of pharmaceutical compositions for use in the methods described herein include dermatological compositions adapted for cutaneous topical administration. For example, dermatological compositions include a cosmetically or pharmaceutically acceptable medium. The dermatological compositions for topical administration can include ointments, lotions, creams, gels, drops, suppositories, sprays, liquids and powders. In some embodiments, conventional pharmaceutical carriers, aqueous, powder or oily bases, thickeners, skin enhancers and the like can be necessary or desirable and therefore can be used. Examples of suitable enhancers include, but are not limited to, ethers such as diethylene glycol monoethyl ether (available commercially as TRANSCUTOL®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80), and lecithin (U.S. Pat. No. 4,783, 450); alcohols such as ethanol, propanol, octanol, benzyl alcohol, and the like; polyethylene glycol and esters thereof such as polyethylene glycol monolaurate; amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly citric acid and succinic acid. AZONE® and sulfoxides such as DMSO and Ct0MSO may also be used, but are less preferred.

In some embodiments, the pharmaceutical composition is in a dosage form selected from the group consisting of sustained release forms, controlled release forms, delayed release forms and response release forms.

VIII. METHODS OF USE

The compositions and methods described herein have utility in treating many disease conditions, including cancer (e.g., colorectal, brain, and glioblastoma). In one embodiment, the compositions and methods described herein are used to treat diseases such as ocular melanoma, desmoplastic round cell tumor, chondrosarcoma, leptomengial disease, diffuse large B-cell lymphoma, Acute Lymphoblastic Leukemia, Acute Myeloid Leukemia, Adrenocortical Carcinoma, AIDS-Related Cancers, AIDS-Related Lymphoma, Anal or Rectal Cancer, Appendix Cancer, Astrocytomas, and Atypical Teratoid/Rhabdoid Tumor. In one embodiment, the compositions and methods described herein are used to treat diseases such as Basal Cell Carcinoma, Basal Cell Nevus Syndrome, Gorlin-Nevus Syndrome, Bile Duct Cancer, Bladder Cancer, Bone Cancer, Osteosarcoma and Malignant Fibrous Histiocytoma, Brain Tumor, Breast Cance, Bronchial Tumors, Burkitt Lymphoma, and Spinal Cord Tumors. In one embodiment, the compositions and methods described herein are used to treat diseases such as Carcinoid Tumor, Carcinoma of Unknown Primary, Central Nervous System Atypical Teratoid/Rhabdoid Tumor, Leptomeningeal Disease, Central Nervous System Embryonal Tumors, Central Nervous System Lymphoma, Cervical Cancer, Chordoma, Chronic Lymphocytic Leukemia, Chronic Myelogenous Leukemia, Chronic Myeloproliferative Disorders, Colon Cancer, Colorectal Cancer, Craniopharyngioma, and Cutaneous T-Cell Lymphoma (including, but not limited to, Sezary syndrome and mycosis fungoides (MF)). In one embodiment, the compositions and methods described herein are used to treat cdiseases such as Embryonal Tumors of Central Nervous System, Endometrial Cancer, Ependymoblastoma, Ependymoma, Esophageal Cancer, Ewing Sarcoma Family of Tumors, Extracranial Germ Cell Tumor, Extragonadal Germ Cell Tumor, Extrahepatic Bile Duct Cancer, and Eye Cancer. In one embodiment, the compositions and methods described herein are used to treat diseases such as Gallbladder Cancer, Gastric (Stomach) Cancer, Gastrointestinal Carcinoid Tumor, Gastrointestinal Stromal Tumor (GIST), Germ Cell Tumor, Gestational Trophoblastic Tumor, and Glioma. In one embodiment, the compositions and methods described herein are used to treat a cancer selected from the group consisting of Hairy Cell Leukemia, Head and Neck Cancer, Hepatocellular (Liver) Cancer, Histiocytosis, Hodgkin Lymphoma, and Hypopharyngeal Cancer. In one embodiment, the compositions and methods described herein are used to treat cdiseases such as Kaposi Sarcoma, and Kidney (Renal Cell) Cancer. In one embodiment, the compositions and methods described herein are used to treat diseases such as Langerhans Cell Histiocytosis, Laryngeal Cancer, Lip and Oral Cavity Cancer, Liver Cancer, Lung Cancer, Non-Hodgkin Lymphoma, and Primary Central Nervous System Lymphoma. In one embodiment, the compositions and methods described herein are used to treat diseases such as Waldenström's macroglobulinemia (lymphoplasmacytic lymphoma), Malignant Fibrous Histiocytoma of Bone and Osteosarcoma, Medulloblastoma, Medulloepithelioma, Melanoma, Merkel Cell Carcinoma, Mesothelioma, Metastatic Squamous Neck Cancer with Occult Primary, Multiple Endocrine Neoplasia Syndrome, Mouth Cancer, Multiple Myeloma/Plasma Cell Neoplasm, Mycosis Fungoides, Myelodysplastic Syndromes, Myelodysplastic/Myeloproliferative Neoplasms, Multiple Myeloma, and Myeloproliferative Disorders. In one embodiment, the compositions and methods described herein are used to treat cancer. In one embodiment, the compositions and methods described herein are used to treat diseases such as Nasal Cavity and Paranasal Sinus Cancer, Nasopharyngeal Cancer, and Neuroblastoma. In one embodiment, the compositions and methods described herein are used to treat diseases such as Oral Cancer, Lip and Oral Cavity Cancer, Oropharyngeal Cancer, Osteosarcoma and Malignant Fibrous Histiocytoma of Bone, Ovarian Cancer, Ovarian Germ Cell Tumor, Ovarian Epithelial Cancer, and Ovarian Low Malignant Potential Tumor. In one embodiment, the compositions and methods described herein are used to treat diseases such as Pancreatic Cancer, Papillomatosis, Paranasal Sinus and Nasal Cavity Cancer, Parathyroid Cancer, Penile Cancer, Pharyngeal Cancer, Pineal Parenchymal Tumors of Intermediate Differentiation, Pineoblastoma and Supratentorial Primitive Neuroectodermal Tumors, Pituitary Tumor, Pleuropulmonary Blastoma, Pregnancy and Breast Cancer, Primary Central Nervous System Lymphoma, and Prostate Cancer. In one embodiment, the compositions and methods described herein are used to treat a cancer selected from the group consisting of Rectal Cancer, Renal Cell (Kidney) Cancer, Renal Pelvis and Ureter, Respiratory Tract Carcinoma Involving the NUT Gene on Chromosome 15, Retinoblastoma, and Rhabdomyosarcoma. In one embodiment, the compositions and methods described herein are used to treat high grade prostate cancer. In one embodiment, the compositions and methods described herein are used to treat medium grade prostate cancer. In one embodiment, the compositions and methods described herein are used to treat low grade prostate cancer. In one embodiment, the compositions and methods described herein are used to treat castration-resistant prostate cancer.

The inventors have found in in vitro models, in animal models, and in human clinical trials that ONC201 (compound (1)) has broad anti-cancer activity, low toxicity including few, if any, adverse effects, low genotoxicity, and high bioavailability including oral bioavailability. These features allows ONC 201 and various analogs to be particularly well suited for pediatric patients. These features also make ONC 201 and various analogs particularly well suited for chronic therapy, for high risk patients, and to ensure long-lasting responses or stable disease or to prevent disease recurrence.

In one embodiment, the compositions and methods described herein are used to treat a pediatric cancer (e.g., pediatric solid tumors, pediatric sarcomas, pediatric Ewing's sarcomas, pediatric gliomas, pediatric central nervous system cancers, pediatric neuroblastoma pediatric leukemia and pediatric lymphoma).

In one embodiment, the compositions and methods described herein are used to treat a proliferative skin disorder such as psoriasis. In one embodiment, the compositions and methods described herein are used to treat a cancer selected from the group consisting of Salivary Gland Cancer, Sarcoma, Sézary Syndrome, Skin Cancer, Ocular Cancer, Skin Carcinoma, Small Intestine Cancer, Soft Tissue Sarcoma, Squamous Cell Carcinom, Squamous Neck Cancer with Occult Primary, and Supratentorial Primitive Neuroectodermal Tumors. In one embodiment, the compositions and methods described herein are used to treat a cancer selected from the group consisting of T-Cell Lymphoma, Testicular Cancer, Throat Cancer, Thymoma and Thymic Carcinoma, Thyroid Cancer, Transitional Cell Cancer of the Renal Pelvis and Ureter, and Gestational Trophoblastic Tumor. In one embodiment, the compositions and methods described herein are used to treat a cancer selected from the group consisting of Carcinoma of Unknown Primary Site, Cancer of Unknown Primary Site, Unusual Cancers of Childhood, Transitional Cell Cancer of the Renal Pelvis and Ureter, Urethral Cancer, and Uterine Sarcoma. In one embodiment, the compositions and methods described herein are used to treat cancer selected from the group consisting of Vaginal Cancer and Vulvar Cancer. In one embodiment, the compositions and methods described herein are used to treat a cancer selected from the group consisting of Wilms Tumor and Women's Cancers.

In some embodiments, the compositions and methods described herein are used as a first-line therapy (sometimes called primary therapy). In some embodiments, the compositions and methods described herein are used as a second-line therapy. In some embodiments, the compositions and methods described herein are used as a third-line therapy. In some embodiments, the compositions and methods described herein are used as a salvage therapy. The term "salvage therapy" as used herein means a therapeutic agent that can be taken with any regimen after a subject's initial treatment regimen has failed or after the subject's condition has not responded to an initial treatment. In some embodiments, the compositions and methods described herein are used as a rescue therapy. In one embodiment of the rescue therapy, the compositions are used as a rescue agent to counteract the action of an initial treatment. In one embodiment of the rescue therapy, the compositions are used as rescue agent which is administered to a subject who has developed resistance to a standard or an initial treatment. In some embodiments, the compositions and methods described herein are used as a neoadjuvant therapy. In one embodiment, the neoadjuvant therapy comprises administration of one or more of the therapeutic agents described herein to a subject before a main or first line treatment. In one embodiment, the neoadjuvant therapy reduces the size or extent of the cancer being treated before a main or first line treatment is administered to the subject undergoing treatment. In some embodiments, the compositions and methods described herein are used as an adjuvant therapy. In one embodiment, the adjuvant therapy comprises administration of one or more therapeutic agents described herein to a subject, wherein the one or more therapeutic agent that modify the effect of other therapeutic agents that are already administered to the subject or are concurrently administered to the subject or subsequently administered to the subject.

In some embodiments, the compositions and methods described herein exhibit reduced chance of drug-drug interactions. In some embodiments, compound (1) or compound (10) or an analog thereof are eliminated from the patient's body before it can interact with another pharmaceutically active agent.

In some embodiments, the compositions and methods of described herein exhibit toxicity levels that facilitates combinations with other pharmaceutical agents.

The methods and compositions described herein are not limited to a particular animal species. In one embodiment, a subject treated according to methods and using compositions described herein, can be mammalian or non-mammalian. In one embodiment, a mammalian subject mammal includes, but is not limited to, a human; a non-human primate; a rodent such as a mouse, rat, or guinea pig; a domesticated pet such as a cat or dog; a horse, cow, pig, sheep, goat, or rabbit. In one embodiment, a non-mammalian subject includes, but is not limited to, a bird such as a duck, goose, chicken, or turkey. In some embodiments, the subject is a human. In one embodiment, subjects can be either gender and any age. The composition and methods can also be used to prevent cancer. The composition and methods can also be used to stimulate the immune system.

The methods and compositions described herein are not limited to a particular age of the subject. In one embodiment, a subject treated according to methods and using compositions described herein can be over the age of 50 years, over the age of 55 years, over the age of 60 years, or over the age of 65 years. In one embodiment, a subject treated according to methods and using compositions described herein can be under the age of 50 years, under the age of 55 years, under the age of 60 years, or under the age of 65 years.

In one embodiment, a subject treated according to methods and using compositions described herein can be a pediatric patient. In one embodiment, the pediatric patient ct is younger than 18 years old, younger than 17 years old, younger than 16 years old, younger than 15 years old, younger than 14 years old, wherein is younger than 13 years old, younger than 12 years old, younger than 11 years old, younger than 10 years old, younger than 9 years old, younger than 8 years old, younger than 7 years old, younger than 6 years old, younger than 5 years old, younger than 4 years old, younger than 3 years old, younger than 2 years old, younger than 1 year old. In one embodiment, the pediatric patient is younger than 12 months old, younger than 11 months old, younger than 10 months old, younger than 9 months old, younger than 8 months old, younger than 7 months old, younger than 6 months old, is younger than 5 months old, younger than 4 months old, younger than 3 months old, younger than 2 months old, younger than 1 month old. In one embodiment, the pediatric patient younger than 4 weeks old, younger than 3 weeks old, younger than 2 weeks old, younger than 1 weeks old. In one embodiment, the pediatric patient is younger than 7 days old, younger than 6 days old, younger than 5 days old, younger than 4 days old, younger than 3 days old, younger than 2 days old, or younger than 1 day old. In one embodiment, the pediatric patient is a neonate. In one embodiment, the pediatric patient is prematurely born. In one embodiment, the pediatric patient is a neonate.

In one embodiment, the patient is less than 45 kg in weight, less than 40 kg in weight, less than 35 kg in weight, less than 30 kg in weight, less than 25 kg in weight, less than 20 kg in weight, less than 15 kg in weight, less than 14 kg in weight, less than 10 kg in weight, less than 5 kg in weight, less than 4 kg in weight, less than 3 kg in weight, less than 2 kg in weight, or less than 1 kg in weight.

In one embodiment, the subject has received at least one prior therapeutic agent. In one embodiment the subject has received at least two, at least three, or at least four prior therapeutic agents. In one embodiment the prior therapeutic agent is ibrutinib, bortezomib, carfilzomib, temozolomide, bevacizumab, cyclophosphamide, hydroxydaunorubicin, vincristine, prednisone, cytarabine, cisplatin, rituximab, 5-fluorouracil, oxaliplatin, leucovorin, or lenalidomide.

In one embodiment, the subject has been treated with radiation. In one embodiment, the subject has been treated with surgery. In one embodiment, the subject has been treated with adoptive T-cell therapy.

In some embodiments, the cancer no longer responds to treatment with ibrutinib, bortezomib, carfilzomib, temozolomide, bevacizumab, cyclophosphamide, hydroxydaunorubicin, vincristine, prednisone, cytarabine, cisplatin, rituximab, 5-fluorouracil, oxaliplatin, leucovorin, lenalidomide, radiation, surgery, or a combination thereof.

In some embodiments, the compositions and methods described herein have a dose response relation in cancer cells that is different from the dose response relation of the same compositions and methods in normal cells. FIG. 1, for example, illustrates the dose response relation of compound (1) on proliferation and cell death in normal and tumor cells. FIG. 1 shows cell viability following treatment with compound (1) at indicated concentrations for 72 hours. The tumors tested included a human colon cancer cell line (HCT116), breast tumor cell line (MDA-MB-231), and a human primary glioblastoma cell line (U87). And the normal cells tested included human foreskin fibroblasts (HFF), human fetal lung fibroblast (MRC-5) cells, and a human lung fibroblast cell line (WI-38). Doxorubicin was used as a positive control at 1 μg/mL in normal fibroblasts. As shown in FIG. 1, cell viability of normal cells tested is at least about 75% at about 1-5 mg/mL concentration of compound (1), whereas viability of tumor cells is significantly lower (e.g., at or below 50%) at the same concentration of compound (1). Moreover, as the concentration of compound (1) increases beyond about 5 mg/mL viability of tumor cells falls to below 25%, whereas viability of normal cells remains at about 75%.

Figure 2:
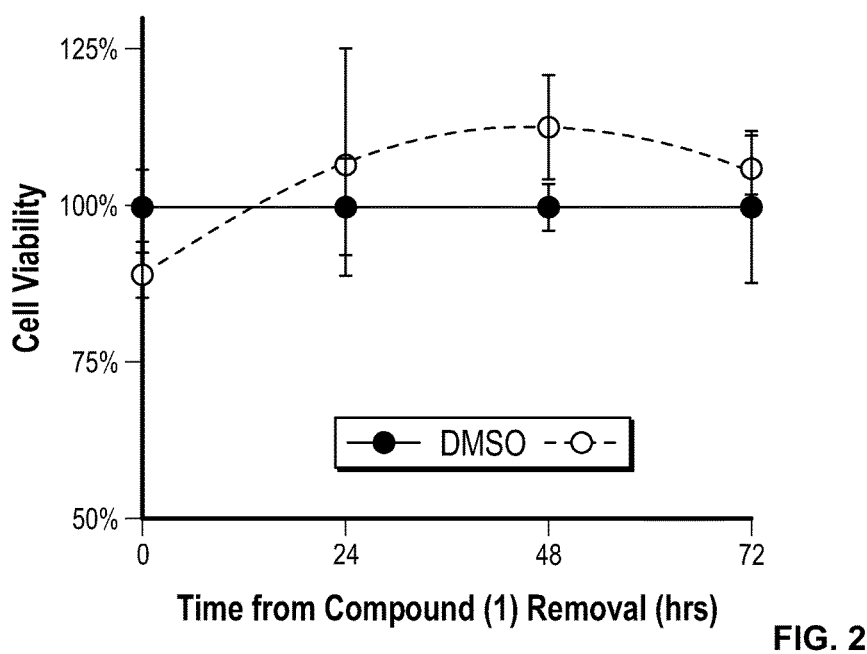
FIG. 2 illustrates cell viability assay in human fetal lung fibroblast (MRC-5) cells following 72 hour treatment with compound (1).
Figure 3:
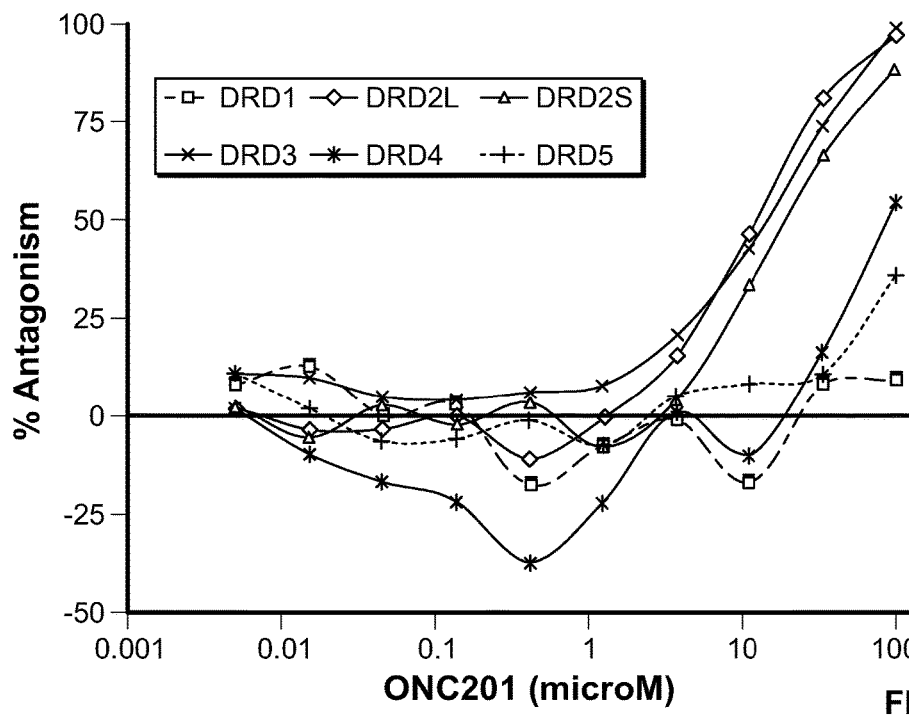
FIG. 3 illustrates antagonism by ONC201 of dopamine receptor (DRD1, DRD2S, DRD2L, DRD3, DRD4, and DRD5).
Figure 4:
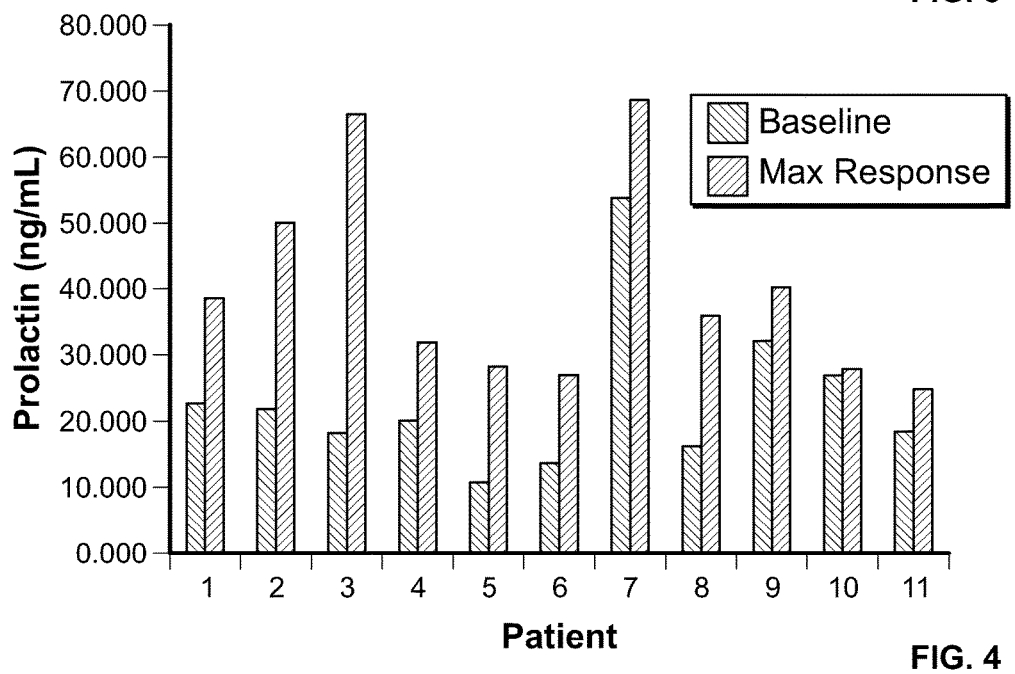
FIG. 4 illustrates soluble prolactin detected by an ELISA assay in the peripheral blood of advanced solid tumor patients at baseline and following a single ONC201 dose (PO 125-625 mg). Sampling time points post-treatment include 6 hours, 1, 2, 7, and 21 days post-treatment.

FIG. 2 illustrates cell viability assays in human fetal lung fibroblast (MRC-5) cells following 72 hour treatment with compound (1) (5 μM) or DMSO and the indicated recovery period in complete drug-free media after treatment. The time points are given as time following removal of compound (1) after 72 hour treatment. As shown in FIG. 2, cell recovery was seen with compound (1), but not with DMSO.

In some embodiments, the compositions and methods described herein have utility in treating cancer in a subject. In one embodiment, the compositions and methods described herein have utility in treating cancer in a human subject. In some embodiments, the treatment method comprises administering to a subject in need of such treatment, a pharmaceutically effective amount of compound (1) or compound (10) or an analog thereof, or a pharmaceutically acceptable salt thereof and a pharmaceutically acceptable carrier.

In one embodiment, the treatment method comprises administering to a subject in need of such treatment: (i) a first therapeutic agent including compound (1) or compound (10) or an analog thereof, or a pharmaceutically acceptable salt thereof in combination with (ii) a second therapeutic agent, wherein the first and the second therapeutic agents are administered either simultaneously or sequentially. The second therapeutic agent can be any suitable therapeutic agent, including any pharmaceutically active agent disclosed herein. A pharmaceutically acceptable salt of compound (1) includes the di-hydrochloride salt below:

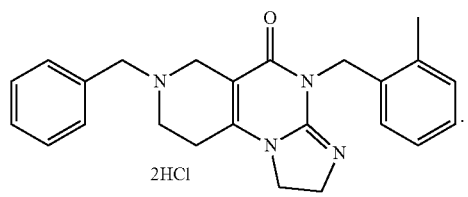 [SMILES: Cc1ccccc1CN1C(=O)C2=C(CCN(Cc3ccccc3)C2)N2CCN=C12]

It is understood that a di-hydrochloride salt of compound (1) or an analog thereof (including, but not limited to, a compound of formula (10)), or an alternative di-salt thereof apparent from the teaching of this disclosure, can be substituted for compound (1) or an analog thereof in a composition or dosing regimen described herein.

In some embodiments, the treatment method comprises administering a synergistic pharmaceutical combination, either simultaneously or sequentially, to a subject in need of such treatment, wherein the synergistic pharmaceutical combination comprising (i) a first therapeutic agent comprising compound (1) or compound (10) or an analog thereof, or a pharmaceutically acceptable salt thereof; and (ii) a second therapeutic agent. In one embodiment, the treatment method comprises administering to a subject in need of such treatment, either simultaneously or sequentially, therapeutically synergistic effective amounts of the first therapeutic agent in combination with the second therapeutic agent. In one embodiment, the treatment method comprises administering to a subject in need of such treatment, an effective amount of the first therapeutic agent in combination with an effective amount of the second therapeutic agent, wherein the combination provides a synergistic effect in the in vivo treatment of a cancer sensitive to the combination, and wherein the first and the second therapeutic agents are administered either simultaneously or sequentially. In one embodiment, the treatment method comprises administering to a subject in need of such treatment, an effective amount of the first therapeutic agent in combination with an effective amount of a second therapeutic agent, wherein the combination provides a synergistic effect in the in vivo treatment of a minimal residual disease sensitive to the combination, and wherein the first and second therapeutic agents are administered either simultaneously or sequentially.

In some embodiments, the second therapeutic agent can be given before or prior to the first therapeutic agent.

In one embodiment, the treatment method targets a cancer selected from the group consisting of solid tumors, liquid tumors, lymphomas, leukemias, or myelomas.

In one embodiment, the treatment method targets a solid tumor, wherein the solid tumor is selected from the group consisting of: Cervical Cancer, Endometrial Cancer, Extracranial Germ Cell Tumor; Extragonadal Germ Cell Tumor; Germ Cell Tumor; Gestational Trophoblastic Tumor; Ovarian Cancer, Ovarian Germ Cell Tumor, Ovarian Epithelial Cancer, and Ovarian Low Malignant Potential Tumor; Penile Cancer, Prostate Cancer; Pregnancy and Breast Cancer; high grade prostate cancer; medium grade prostate cancer; low grade prostate cancer; castration-resistant prostate cancer; Breast Cancer; Bile Duct Cancer; Extrahepatic Bile Duct Cancer; Gallbladder Cancer; Hepatocellular (Liver) Cancer; Kidney (Renal Cell) Cancer; Liver Cancer, Renal Cell (Kidney) Cancer, Renal Pelvis and Ureter; Basal Cell Carcinoma; Basal Cell Nevus Syndrome, Gorlin-Nevus Syndrome, Melanoma, Merkel Cell Carcinoma, Papillomatosis, Multiple Endocrine Neoplasia Syndrome; Pancreatic Cancer, Parathyroid Cancer, ocular melanoma; Eye Cancer; Retinoblastoma; Malignant Fibrous Histiocytoma; Ewing Sarcoma Family of Tumors; desmoplastic round cell tumor; chondrosarcoma, Kaposi Sarcoma, Rhabdomyosarcoma; Spinal Cord Tumors, Leptomeningeal Disease, Central Nervous System Embryonal Tumors, Chordoma, Embryonal Tumors of Central Nervous System, Ependymoblastoma, Ependymoma, Neuroblastoma; Pineal Parenchymal Tumors of Intermediate Differentiation, Pineoblastoma; Adrenocortical Carcinoma; Bone Cancer, Osteosarcoma; Malignant Fibrous Histiocytoma of Bone and Osteosarcoma; Osteosarcoma and Malignant Fibrous Histiocytoma of Bone; Carcinoid Tumor, Carcinoma of Unknown Primary, Bronchial Tumors, Lung Cancer, Pleuropulmonary Blastoma; Respiratory Tract Carcinoma Involving the NUT Gene on Chromosome 15, Astrocytomas, Atypical Teratoid/Rhabdoid Tumor; Central Nervous System Atypical Teratoid/Rhabdoid Tumor, Craniopharyngioma, Glioma, Brain cancer, Medulloblastoma, Medulloepithelioma, Supratentorial Primitive Neuroectodermal Tumors; Pituitary Tumor; Gastric (Stomach) Cancer, Gastrointestinal Carcinoid Tumor, Gastrointestinal Stromal Tumor (GIST), Bladder Cancer, Anal or Rectal Cancer, Appendix Cancer, Esophageal Cancer, Hypopharyngeal Cancer; Laryngeal Cancer, Lip and Oral Cavity Cancer, Metastatic Squamous Neck Cancer with Occult Primary, Mouth Cancer, Nasal Cavity and Paranasal Sinus Cancer, Nasopharyngeal Cancer, Oral Cancer, Lip and Oral Cavity Cancer, Oropharyngeal Cancer, Paranasal Sinus and Nasal Cavity Cancer, Pharyngeal Cancer; Head and Neck Cancer, and Mesothelioma.

In one embodiment, the treatment method targets a lymphoma selected from the group consisting of: diffuse large B-cell lymphoma, AIDS-Related Lymphoma, Cutaneous T-Cell Lymphoma, Sezary syndrome, mycosis fungoides (MF); Histiocytosis; Burkitt Lymphoma, and Central Nervous System Lymphoma; Non-Hodgkin Lymphoma, and Primary Central Nervous System Lymphoma, Hodgkin Lymphoma, Waldenström's macroglobulinemia; Mycosis Fungoides; Primary Central Nervous System Lymphoma; lymphoplasmacytic lymphoma, and Primary Central Nervous System Lymphoma.

In one embodiment, the treatment method targets a Non-Hodgkin's lymphoma (NHL) selected from the group consisting of: mantle cell lymphoma, diffuse large B-cell lymphoma, follicular lymphoma, marginal zone lymphoma, small lymphocytic lymphoma, lyphoplasmacytic NHL, Waldenstrom's macroglobulinaemia, and skin lymphomas.

In one embodiment, the treatment method targets a leukemia selected from the group consisting of: Acute Lymphoblastic Leukemia (ALL), Chronic Lymphocytic Leukemia (CLL), Chronic Myeloproliferative Disorders; Hairy Cell Leukemia; Acute Myeloid Leukemia (AML); Chronic Myelogenous Leukemia (CML); and Langerhans Cell Histiocytosis.

In one embodiment, the treatment method targets an acute leukemia selected from the group consisting of: acute lymphotye leukemia, acute myeloid leukemia, chronic lymphoblasitc leukemia, chronic myeloid leukemia, myelodysplastic syndrome, and myeloproliferative disease.

In one embodiment, the treatment method targets a myeloma selected from the group consisting of: IgA myeloma; IgG myeloma; IgM myeloma; IgD myeloma; IgE myeloma; light chain myeloma; non secretory myeloma; Multiple Myeloma/Plasma Cell Neoplasm, Multiple Myeloma, Myelodysplastic Syndromes, Myelodysplastic/Myeloproliferative Neoplasms, and Myeloproliferative Disorders.

In one embodiment, the treatment method targets a cancer selected from the group consisting of: Acute Lymphoblastic Leukemia, Acute Myeloid Leukemia, Adrenocortical Carcinoma, AIDS-Related Cancers, AIDS-Related Lymphoma, Anal or Rectal Cancer, Appendix Cancer, Astrocytomas, and Atypical Teratoid/Rhabdoid Tumor.

In one embodiment, the treatment method targets a cancer selected from the group consisting of: Basal Cell Carcinoma, Basal Cell Nevus Syndrome, Gorlin-Nevus Syndrome, Bile Duct Cancer, Bladder Cancer, Bone Cancer, Osteosarcoma and Malignant Fibrous Histiocytoma, Brain Tumor, Breast Cance, Bronchial Tumors, Burkitt Lymphoma, and Spinal Cord Tumors.

In one embodiment, the treatment method targets a cancer selected from the group consisting of: Carcinoid Tumor, Carcinoma of Unknown Primary, Central Nervous System Atypical Teratoid/Rhabdoid Tumor, Central Nervous System Embryonal Tumors, Central Nervous System Lymphoma, Cervical Cancer, Chordoma, Chronic Lymphocytic Leukemia, Chronic Myelogenous Leukemia, Chronic Myeloproliferative Disorders, Colon Cancer, Colorectal Cancer, Craniopharyngioma, and Cutaneous T-Cell Lymphoma (including, but not limited to, Sezary syndrome and mycosis fungoides).

In one embodiment, the treatment method targets a cancer selected from the group consisting of: Embryonal Tumors of Central Nervous System, Endometrial Cancer, Ependymoblastoma, Ependymoma, Esophageal Cancer, Ewing Sarcoma Family of Tumors, Desmoplastic Round Cell Tumor, Chondrosarcoma, Extracranial Germ Cell Tumor, Extragonadal Germ Cell Tumor, Extrahepatic Bile Duct Cancer, and Eye Cancer, including Intraocular Melanoma and Retinoblastoma.

In one embodiment, the treatment method targets a cancer selected from the group consisting of: Gallbladder Cancer, Gastric (Stomach) Cancer, Gastrointestinal Carcinoid Tumor, Gastrointestinal Stromal Tumor (GIST), Germ Cell Tumor, Gestational Trophoblastic Tumor, and Glioma.

In one embodiment, the treatment method targets a cancer selected from the group consisting of: Hairy Cell Leukemia, Head and Neck Cancer, Hepatocellular (Liver) Cancer, Histiocytosis, Hodgkin Lymphoma, and Hypopharyngeal Cancer.

In one embodiment, the treatment method targets a cancer selected from the group consisting of Kaposi Sarcoma and Kidney (Renal Cell) Cancer.

In one embodiment, the treatment method targets a cancer selected from the group consisting of: Langerhans Cell Histiocytosis, Laryngeal Cancer, Lip and Oral Cavity Cancer, Liver Cancer, Lung Cancer, including Non-Small Cell Lung Cancer, and Small Cell Lung Cance, Non-Hodgkin Lymphoma, and Primary Central Nervous System Lymphoma.

In one embodiment, the treatment method targets a cancer selected from the group consisting of: Waldenström's macroglobulinemia (lymphoplasmacytic lymphoma), Malignant Fibrous Histiocytoma of Bone and Osteosarcoma, Medulloblastoma, Medulloepithelioma, Melanoma, Merkel Cell Carcinoma, Mesothelioma, Metastatic Squamous Neck Cancer with Occult Primary, Multiple Endocrine Neoplasia Syndrome, Mouth Cancer, Multiple Myeloma/Plasma Cell Neoplasm, Mycosis Fungoides, Myelodysplastic Syndromes, Myelodysplastic/Myeloproliferative Neoplasms, Multiple Myeloma, and Myeloproliferative Disorders.

In one embodiment, the treatment method is useful for treating a cancer selected from the group consisting of: Nasal Cavity and Paranasal Sinus Cancer, Nasopharyngeal Cancer, and Neuroblastoma.

In one embodiment, the treatment method is useful for treating a cancer selected from the group consisting of: Oral Cancer, Lip and Oral Cavity Cancer, Oropharyngeal Cancer, Osteosarcoma and Malignant Fibrous Histiocytoma of Bone, Ovarian Cancer, Ovarian Germ Cell Tumor, Ovarian Epithelial Cancer, and Ovarian Low Malignant Potential Tumor.

In one embodiment, the treatment method is useful for treating a cancer selected from the group consisting of: Pancreatic Cancer, Papillomatosis, Paranasal Sinus and Nasal Cavity Cancer, Parathyroid Cancer, Penile Cancer, Pharyngeal Cancer, Pineal Parenchymal Tumors of Intermediate Differentiation, Pineoblastoma and Supratentorial Primitive Neuroectodermal Tumors, Pituitary Tumor, Pleuropulmonary Blastoma, Pregnancy and Breast Cancer, Primary Central Nervous System Lymphoma, and Prostate Cancer.

In one embodiment, the treatment method is useful for treating a cancer selected from the group consisting of Rectal Cancer, Renal Cell (Kidney) Cancer, Renal Pelvis and Ureter, Respiratory Tract Carcinoma Involving the NUT Gene on Chromosome 15, Retinoblastoma, and Rhabdomyosarcoma.

In one embodiment, the treatment method is useful for treating a cancer selected from the group consisting of: Salivary Gland Cancer, Sarcoma, Sézary Syndrome, Skin Cancer, Skin Carcinoma, Small Intestine Cancer, Soft Tissue Sarcoma, Squamous Cell Carcinom, Squamous Neck Cancer with Occult Primary, and Supratentorial Primitive Neuroectodermal Tumors.

In one embodiment, the treatment method is useful for treating a cancer selected from the group consisting of: T-Cell Lymphoma, Testicular Cancer, Throat Cancer, Thymoma and Thymic Carcinoma, Thyroid Cancer, Transitional Cell Cancer of the Renal Pelvis and Ureter, and Gestational Trophoblastic Tumor.

In one embodiment, the treatment method is useful for treating a cancer selected from the group consisting of: Carcinoma of Unknown Primary Site, Cancer of Unknown Primary Site, Unusual Cancers of Childhood, Transitional Cell Cancer Of the Renal Pelvis and Ureter, Urethral Cancer, and Uterine Sarcoma.

In one embodiment, the treatment method is useful for treating a cancer selected from the group consisting of: Vaginal Cancer and Vulvar Cancer.

In one embodiment, the treatment method is useful for treating a cancer selected from the group consisting of: Wilms Tumor and Women's Cancers.

In some embodiments, treatment of cancer comprises prevention of tumor growth in a cancer subject. In some embodiments, treatment of cancer comprises prevention of formation of cancer metastases in a cancer subject. In some embodiments, treatment of cancer comprises targeted treatment of minimal residual disease in a cancer subject known to have the minimal residual disease in a cancer or a subject at risk for having minimal residual disease.

This might be indicated after treatment of the primary tumor by surgery and/or after chemotherapy (radiotherapy) has been initiated or determined to be efficacious. Disseminated tumor cells may be in their dormant state and often cannot be attacked by chemotherapy (radiotherapy). A thus treated patient seemingly is in a healed state, and referred to as "minimal residual disease." Nevertheless, the dormant tumor cells have a potential to form metastases if they become metastasizing cells due to a growth stimulus after a longer dormant state.

As used herein, "minimal residual disease" denotes a small number of cancer cells that remain in a subject during treatment or after treatment when the subject is in remission (exhibiting no symptoms or signs of the disease). The methods described herein are preferably applied to a form of the diseases listed herein, including adult and childhood forms of these diseases.

In one embodiment, the treatment method is useful for treating an autoimmune disease. Autoimmune diseases include, but are not limited to alopecia areata, antiphospholipid, autoimmune hepatits, celiac disease, diabetes type 1, Graves' disease, Guillain-Barre syndrome, Hashimoto's disease, hemolytic anemia, idiopathic thrombocytopenic purpura, inflammatory bowel disease, inflammatory myopathies, multiple sclerosis, primary biliary cirrhosis, psoriasis, rheumatoid arthritis, scleroderma, Sjögren's syndrome, systemic lupus erythematosus, and vitiligo.

In one embodiment, the treatment method is useful for treating autoimmune and inflammatory disorders of the peripheral nerve system such as amyotrophic lateral sclerosis (Lou Gehrig's disease), based on various causes such as metabolic disorders that include diabetes, B12 and folate vitamin deficiencies, chemotherapy medications and medicines used to treat HIV, poisons that cause peripheral nerve damage, cancers that develop peripheral neuropathies as well as paraneoplastic syndromes, alcohol abuse, chronic kidney disease, injuries that cause compression on nerves and other lesions, infections such as Lyme disease, Guillain Barre syndrome, connective tissue disease, rheumatoid arthritis, Sjogren's syndrome, systemic lupus erythematosus, certain inflammatory conditions such as sarcoidosis, coeliac disease, hereditary diseases such as charcot marie tooth syndrome, Friedreich's ataxia, and/or idiopathic where no specific cause is found but inflammatory and/or autoimmune mechanisms are the cause of onset.

In one embodiment, the treatment method is useful for treating autoimmune and inflammatory disorders with ocular manifestations. Such ocular manifestations include, but are not limited to, ocular cicatricial pemphigoid, Mooren's corneal ulcer, various forms of uveitis, rheumatoid arthritis, systemic lupus erythematosus, polyarteritis nodosa, relapsing polychondritis, Wegener's granulomatosis, scleroderma, Behcet's disease, Reiter's disease, inflammatory bowel disease (ulcerative colitis and Crohn's disease) and ankylosing spondylitis, retinitis pigmentosa, macular degeneration, keratoconjunctivitis sicca, scleritis, episcleritis, keratitis, peripheral corneal ulceration, and less common entities such as choroiditis, retinal vasculitis, episcleral nodules, retinal detachments, and/or macular edema.

In one embodiment, the treatment method is useful for treating acute allograft rejection in transplant patients. In one embodiment, the treatment method is useful for treating ischemic stroke. In one embodiment, the treatment method is useful for treating inflammatory diseases including, but not limited to, arthritis, psoriasis, asthma, and colitis.

In one embodiment, a therapeutic agent includes a pharmaceutically acceptable mono-salt of compound (1) or an analog thereof (e.g., a compound of formula (10)). In one embodiment, a therapeutic agent includes a pharmaceutically acceptable di-salt of compound (1) or an analog thereof (e.g., a compound of formula (10)). As described herein, some of the analogs can be tri-salts In one embodiment, a therapeutic agent includes compound (1) or an analog thereof (e.g., a compound of formula (10)) in the form of a pharmaceutically acceptable mono- or di-salt selected from the group consisting of hydrochloride, hydrobromide, hydrogensulphate, sulfates, phosphates, fumarates, succinates, oxalates and lactates, bisulfates, hydroxyl, tartrate, nitrate, citrate, bitartrate, carbonate, malate, maleate, fumarate sulfonate, methylsulfonate, formate, acetate, and carboxylate. In one embodiment, a therapeutic agent includes compound (1) or an analog thereof in the form of a pharmaceutically acceptable mono- or di-salt selected from p-toluene-sulfonate, benzenesulfonate, methanesulfonate, oxalate, succinate, tartrate, citrate, fumarate and maleate. In one embodiment, a therapeutic agent includes compound (1) or an analog thereof in the form of a pharmaceutically acceptable mono- or di-salt having a counter ion selected from the group consisting of ammonium, sodium, potassium, calcium, magnesium, zinc, lithium, and/or with counter-ions such as methylamino, dimethylamino, diethylamino, triethylamino counter-ions, and combinations thereof. In one embodiment, a therapeutic agent includes compound described herein in the form of a halide di-salt, such as a di-hydrochloride salt or a di-hydrobromide salt.

In some embodiments of the treatment method, the second therapeutic agent includes an anti-cancer agent. In some embodiments of the treatment method, the second therapeutic agent is selected, without limitation, from acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bevacizumab, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflomithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-1b, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, zorubicin and combinations thereof.

In some embodiments of the treatment method, the second therapeutic agent is selected, without limitation, from hormone analogs and antihormones, aromatase inhibitors, LHRH agonists and antagonists, inhibitors of growth factors, growth factor antibodies, growth factor receptor antibodies, tyrosine kinase inhibitors; antimetabolites; antitumour antibiotics; platinum derivatives; alkylation agents;

antimitotic agents; tubuline inhibitors; PARP inhibitors, topoisomerase inhibitors, serine/threonine kinase inhibitors, tyrosine kinase inhibitors, protein protein interaction inhibitors, MEK inhibitors, ERK inhibitors, IGF-1R inhibitors, ErbB receptor inhibitors, rapamycin analogs, amifostin, anagrelid, clodronat, filgrastin, interferon, interferon alpha, leucovorin, rituximab, procarbazine, levamisole, mesna, mitotane, pamidronate and porfimer, 2-chlorodesoxyadenosine, 2-fluorodesoxy-cytidine, 2-methoxyoestradiol, 2C4,3-alethine, 131-1-TM-601, 3CPA, 7-ethyl-10-hydroxycamptothecin, 16-aza-epothilone B, A 105972, A 204197, abiraterone, aldesleukin, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, AMG-479 (ganitumab), ARRY 162, ARRY 438162, ARRY-300, ARRY-142886/AZD-6244 (selumetinib), ARRY-704/AZD-8330, AR-12, AR-42, AS-703988, AXL-1717, AZD-8055, AZD-5363, AZD-6244, ARQ-736, ARQ 680, AS-703026 (primasertib), avastin, AZD-2014, azacytidine, azaepothilone B, azonafide, BAY-43-9006, BAY 80-6946, BBR-3464, BBR-3576, bevacizumab, BEZ-235, biricodar dicitrate, BCX-1777, BKM-120, bleocin, BLP-25, BMS-184476, BMS-247550, BMS-188797, BMS-275291, BMS-663513, BMS-754807, BNP-1350, BNP-7787, BIBW 2992 (afatinib, tomtovok), BIBF 1120 (vargatef), BI 836845, BI 2536, BI 6727, BI 836845, BI 847325, BI 853520, BUB-022, bleomycinic acid, bleomycin A, bleomycin B, brivanib, bryostatin-1, bortezomib, brostallicin, busulphan, BYL-719, CA-4 prodrug, CA-4, CapCell, calcitriol, canertinib, canfosfamide, capecitabine, carboxyphthalatoplatin, CC1-779, CC-115, CC-223, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, CKI-27, clofarabin, colchicin, combretastatin A4, COT inhibitors, CHS-828, CH-5132799, CLL-Thera, CMT-3 cryptophycin 52, CTP-37, CTLA-4 monoclonal antibodies, CP-461, CV-247, cyanomorpholino-doxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, E7010, E-6201, edatrexat, edotreotide, efaproxiral, eflornithine, EGFR inhibitors, EKB-569, EKB-509, enzastaurin, enzalutamide, elsamitrucin, epothilone B, epratuzumab, ER-86526, erlotinib, ET-18-0CH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fotemustine, galarubicin, gallium maltolate, gefinitib, gemtuzumab, gimatecan, glufosfamide, GCS-100, GDC-0623, GDC-0941 (pictrelisib), GDC-0980, GDC-0032, GDC-0068, GDC-0349, GDC-0879, G17DT immunogen, GMK, GPX-100, gp100-peptide vaccines, GSK-5126766, GSK-690693, GSK-1120212 (trametinib), GSK-2118436 (dabrafenib), GSK-2126458, GSK-2132231A, GSK-2334470, GSK-2110183, GSK-2141795, GW2016, granisetron, herceptin, hexamethylmelamine, histamine, homoharringtonine, hyaluronic acid, hydroxyurea, hydroxyprogesterone caproate, ibandronate, ibritumomab, idatrexate, idenestrol, IDN-5109, IGF-1R inhibitors, IMC-1C11, IMC-Al2 (cixutumumab), immunol, indisulam, interferon alpha-2a, interferon alpha-2b, pegylated interferon alpha-2b, interleukin-2, INK-1117, INK-128, INSM-18, ionafarnib, ipilimumab, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, KW-2450, lobaplatin, leflunomide, lenograstim, leuprolide, leuporelin, lexidronam, LGD-1550, linezolid, lutetium texaphyrin, lometrexol, losoxantrone, LU 223651, lurtotecan, LY-S6AKT1, LY-2780301, mafosfamide, marimastat, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, motexaf in gadolinium, MS-209, MS-275, MX6, neridronate, neratinib, Nexavar, neovastat, nilotinib, nimesulide, nitroglycerin, nolatrexed, norelin, N-acetylcysteine, 06-benzylguanine, oblimersen, omeprazole, oncophage, oncoVEXGM-CSF, ormiplatin, ortataxel, OX44 antibodies, OSI-027, OSI-906 (linsitinib), 4-1BB antibodies, oxantrazole, oestrogen, panitumumab, patupilone, pegfilgrastim, PCK-3145, pegfilgrastim, PBI-1402, PBI-05204, PD0325901, PD-1 antibodies, PEG-paclitaxel, albumin-stabilized paclitaxel, PEP-005, PF-05197281, PF-05212384, PF-04691502, PHT-427, P-04, PKC412, P54, PI-88, pelitinib, pemetrexed, pentrix, perifosine, perillylalcohol, pertuzumab, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, R115777, RAF-265, ramosetron, ranpirnase, RDEA-119/BAY 869766, RDEA-436, rebecamycin analogs, receptor tyrosine kinase (RTK) inhibitors, revimid, RG-7167, RG-7304, RG-7421, RG-7321, RG 7440, rhizoxin, rhu-MAb, rinfabate, risedronate, rituximab, robatumumab, rofecoxib, RO-31-7453, RO-5126766, RO-5068760, RPR 109881A, rubidazone, rubitecan, R-flurbiprofen, RX-0201, S-9788, sabarubicin, SAHA, sargramostim, satraplatin, SB 408075, Se-015/Ve-015, SU5416, SU6668, SDX-101, semustin, seocalcitol, SM-11355, SN-38, SN-4071, SR-27897, SR-31747, SR-13668, SRL-172, sorafenib, spiroplatin, squalamine, suberanilohydroxamic acid, sutent, T 900607, T 138067, TAK-733, TAS-103, tacedinaline, talaporf in, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valrubicin, vatalanib, vincristine, vinflunine, virulizin, WX-UK1, WX-554, vectibix, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZD1839, ZSTK-474, zoledronat, zosuquidar, and combinations thereof.

In some embodiments of the treatment method, the second therapeutic agent is selected from the group consisting of tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxy-progesterone, octreotide, and combinations thereof. In some embodiments of the treatment method, the second therapeutic agent is selected, without limitation, from the group consisting of LHRH agonists and LHRH antagonists. In some embodiments, a LHRH agonist is selected from the group consisting of goserelin acetate, luprolide acetate, triptorelin pamoate and combinations thereof. In some embodiments, the second therapeutic agent includes a LHRH antagonist is selected from the group consisting of Degarelix, Cetrorelix, Abarelix, Ozarelix, Degarelix combinations thereof. In some embodiments of the treatment method, the second therapeutic agent includes an inhibitor of a growth factor. In some embodiments, the inhibitor of a growth factor is selected, without limitation, from the group consisting of inhibitors of: platelet derived growth factor (PDGF), fibroblast growth factor (FGF), vascular endothelial growth factor (VEGF), epidermal growth factor (EGF), insuline-like growth factors (IGF), human epidermal growth factor (HER), hepatocyte growth factor (HGF), and combinations thereof. In some embodiments, the human epidermal growth factor (HER) is selected from the group consisting of HER2, HER3, and HER4.

In some embodiments of the treatment method, the second therapeutic agent includes a tyrosine kinase inhibitor. In some embodiments of the treatment method, the tyrosine kinase inhibitor is selected, without limitation, from the group consisting of cetuximab, gefitinib, imatinib, lapatinib and trastuzumab, and combinations thereof. In some embodiments of the treatment method, the second therapeutic agent includes an aromatase inhibitor. In some embodiments of the treatment method, the aromatase inhibitor is selected from the group consisting of anastrozole, letrozole, liarozole, vorozole, exemestane, atamestane, and combinations thereof.

In some embodiments of the treatment method, the second therapeutic agent includes an antimetabolite. In some embodiments of the treatment method, the antimetabolite comprises an antifolate. In some embodiments of the treatment method, the antifolate is selected from the group consisting of methotrexate, raltitrexed, pyrimidine analogs, and combinations thereof. In some embodiments of the treatment method, the antimetabolite is a pyrimidine analog. In some embodiments of the treatment method, the pyrimidine analog is selected from the group consisting of 5-fluorouracil, capecitabin, gemcitabin, and combination thereof. In some embodiments of the treatment method, the antimetabolite is a purine analog or an adenosine analog. In some embodiments of the treatment method, the purine analog or adenosine analog is selected from the group consisting of mercaptopurine, thioguanine, cladribine and pentostatin, cytarabine, fludarabine, and combinations thereof. In some embodiments of the treatment method, the second therapeutic agent includes an antitumour antibiotic. In some embodiments of the treatment method, the antitumor antibiotic is selected from the group consisting of anthracyclins, doxorubicin, daunorubicin, epirubicin and idarubicin, mitomycin-C, bleomycin, dactinomycin, plicamycin, streptozocin and combinations thereof. In some embodiments of the treatment method, the second therapeutic agent includes a platinum derivative. In some embodiments of the treatment method, the platinum derivative is selected from the group consisting of cisplatin, oxaliplatin, carboplatin and combinations thereof. In some embodiments of the treatment method, the second therapeutic agent includes an alkylation agent. In some embodiments of the treatment method, the alkylation agent is selected from the group consisting of estramustin, meclorethamine, melphalan, chlorambucil, busulphan, dacarbazin, cyclophosphamide, ifosfamide, temozolomide, nitrosoureas, and combinations thereof. In some embodiments of the treatment method, the second therapeutic agent includes a nitrosourea. In some embodiments of the treatment method, the nitrosourea is selected from the group consisting of carmustin, lomustin, thiotepa, and combinations thereof. In some embodiments of the treatment method, the second therapeutic agent includes an antimitotic agent. In some embodiments of the treatment method, the antimitotic agent is selected from the group consisting of Vinca alkaloids and taxanes. In some embodiments of the treatment method, the taxane is selected from the group consisting of paclitaxel, docetaxel, and combinations thereof. In some embodiments of the treatment method, the Vinca alkaloids are selected from the group consisting of vinblastine, vindesin, vinorelbin, vincristine, and combinations thereof. In some embodiments of the treatment method, the second therapeutic agent includes a topoisomerase inhibitor. In some embodiments of the treatment method, the topoisomerase inhibitor is an epipodophyllotoxin. In some embodiments of the treatment method, the topoisomerase inhibitor, which is an epipodophyllotoxin selected from the group consisting of etoposide, etopophos, teniposide, amsacrin, topotecan, irinotecan, mitoxantron, and combinations thereof. In some embodiments of the treatment method, the second therapeutic agent includes a serine/threonine kinase inhibitor. In some embodiments of the treatment method, the serine/threonine kinase inhibitor is selected from the group consisting of PDK 1 inhibitors, B-Raf inhibitors, mTOR inhibitors, mTORC1 inhibitors, PI3K inhibitors, dual mTOR/PI3K inhibitors, STK 33 inhibitors, AKT inhibitors, PLK 1 inhibitors, inhibitors of CDKs, Aurora kinase inhibitors, and combinations thereof. In some embodiments of the treatment method, the second therapeutic agent includes a tyrosine kinase inhibitor. In some embodiments of the treatment method, the second therapeutic agent includes a PTK2/FAK inhibitor. In some embodiments of the treatment method, the second therapeutic agent includes a protein protein interaction inhibitor. In some embodiments of the treatment method, the protein protein interaction inhibitor is selected from the group consisting of IAP, Mcl-1, MDM2/MDMX and combinations thereof. In some embodiments of the treatment method, the second therapeutic agent includes a rapamycin analog. In some embodiments of the treatment method, the rapamycin analog is selected from the group consisting of everolimus, temsirolimus, ridaforolimus, sirolimus, and combinations thereof. In some embodiments of the treatment method, the second therapeutic agent is selected from the group consisting of amifostin, anagrelid, clodronat, filgrastin, interferon, interferon alpha, leucovorin, rituximab, procarbazine, levamisole, mesna, mitotane, pamidronate and porfimer, and combinations thereof. In some embodiments of the treatment method, the second therapeutic agent is selected from the group consisting of 2-chlorodesoxyadenosine, 2-fluorodesoxy-cytidine, 2-methoxyoestradiol, 2C4,3-alethine, 131-1-TM-601, 3CPA, 7-ethyl-10-hydroxycamptothecin, 16-aza-epothilone B, A 105972, A 204197, abiraterone, aldesleukin, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, AMG-479 (ganitumab), ARRY 162, ARRY 438162, ARRY-300, ARRY-142886/AZD-6244 (selumetinib), ARRY-704/AZD-8330, AR-12, AR-42, AS-703988, AXL-1717, AZD-8055, AZD-5363, AZD-6244, ARQ-736, ARQ 680, AS-703026 (primasertib), avastin, AZD-2014, azacytidine, azaepothilone B, azonafide, BAY-43-9006, BAY 80-6946, BBR-3464, BBR-3576, bevacizumab, BEZ-235, biricodar dicitrate, BCX-1777, BKM-120, bleocin, BLP-25, BMS-184476, BMS-247550, BMS-188797, BMS-275291, BMS-663513, BMS-754807, BNP-1350, BNP-7787, BIBW 2992 (afatinib, tomtovok), BIBF 1120 (vargatef), BI 836845, BI 2536, BI 6727, BI 836845, BI 847325, BI 853520, BUB- 022, bleomycinic acid, bleomycin A, bleomycin B, brivanib, bryostatin-1, bortezomib, brostallicin, busulphan, BYL-719, CA-4 prodrug, CA-4, CapCell, calcitriol, canertinib, canfosfamide, capecitabine, carboxyphthalatoplatin, CCI-779, CC-115, CC-223, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, CKI-27, clofarabin, colchicin, combretastatin A4, COT inhibitors, CHS-828, CH-5132799, CLL-Thera, CMT-3 cryptophycin 52, CTP-37, CTLA-4 monoclonal antibodies, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, E7010, E-6201, edatrexat, edotreotide, efaproxiral, eflornithine, EGFR inhibitors, EKB-569, EKB-509, enzastaurin, enzalutamide, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fotemustine, galarubicin, gallium maltolate, gefinitib, gemtuzumab, gimatecan, glufosfamide, GCS-100, GDC-0623, GDC-0941 (pictrelisib), GDC-0980, GDC-0032, GDC-0068, GDC-0349, GDC-0879, G17DT immunogen, GMK, GPX-100, gp100-peptide vaccines, GSK-5126766, GSK-690693, GSK-1120212 (trametinib), GSK-2118436 (dabrafenib), GSK-2126458, GSK-2132231A, GSK-2334470, GSK-2110183, GSK-2141795, GW2016, granisetron, herceptine, hexamethylmelamine, histamine, homoharringtonine, hyaluronic acid, hydroxyurea, hydroxyprogesterone caproate, ibandronate, ibritumomab, idatrexate, idenestrol, IDN-5109, IGF-1R inhibitors, IMC-1C11, IMC-A12 (cixutumumab), immunol, indisulam, interferon alpha-2a, interferon alpha-2b, pegylated interferon alpha-2b, interleukin-2, INK-1117, INK-128, INSM-18, ionafarnib, ipilimumab, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, KW-2450, lobaplatin, leflunomide, lenograstim, leuprolide, leuporelin, lexidronam, LGD-1550, linezolid, lutetium texaphyrin, lometrexol, losoxantrone, LU 223651, lurtotecan, LY-S6AKT1, LY-2780301, mafosfamide, marimastat, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, motexafin gadolinium, MS-209, MS-275, MX6, neridronate, neratinib, Nexavar, neovastat, nilotinib, nimesulide, nitroglycerin, nolatrexed, norelin, N-acetylcysteine, 06-benzylguanine, benzylguanine, oblimersen, omeprazole, oncophage, oncoVEXGM-CSF, ormiplatin, ortataxel, OX44 antibodies, OSI-027, OSI-906 (linsitinib), 4-1BB antibodies, oxantrazole, oestrogen, panitumumab, patupilone, pegfilgrastim, PCK-3145, pegfilgrastim, PBI-1402, PBI-05204, PD0325901, PD-1 antibodies, PEG-paclitaxel, albumin-stabilized paclitaxel, PEP-005, PF-05197281, PF-05212384, PF-04691502, PHT-427, P-04, PKC412, P54, PI-88, pelitinib, pemetrexed, pentrix, perifosine, perillylalcohol, pertuzumab, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, R115777, RAF-265, ramosetron, ranpirnase, RDEA-119/BAY 869766, RDEA-436, rebeccamycin analogs, receptor tyrosine kinase (RTK) inhibitors, revimid, RG-7167, RG-7304, RG-7421, RG-7321, RG 7440, rhizoxin, rhu-MAb, rinfabate, risedronate, rituximab, robatumumab, rofecoxib, RO-31-7453, RO-5126766, RO-5068760, RPR 109881A, rubidazone, rubitecan, R-flurbiprofen, RX-0201, S-9788, sabarubicin, SAHA, sargramostim, satraplatin, SB 408075, Se-015/Ve-015, SU5416, SU6668, SDX-101, semustin, seocalcitol, SM-11355, SN-38, SN-4071, SR-27897, SR-31747, SR-13668, SRL-172, sorafenib, spiroplatin, squalamine, suberanilohydroxamic acid, sutent, T 900607, T 138067, TAK-733, TAS-103, tacedinaline, talaporf in, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valrubicin, vatalanib, vincristine, vinflunine, virulizin, WX-UK1, WX-554, vectibix, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZD1839, ZSTK-474, zoledronat, zosuquidar, and combinations thereof.

In some embodiments, the other therapeutic agent comprises a steroid. Steroids include, but are not limited to, dexamethasone, prednisolone, methyl prednisolone, prednisone, hydrocortisone, triamcinolone, betamethasone, and cortivazol. In some embodiments, the other therapeutic agent comprises an anti-emetic. Anti-emetics include, but are not limited to, 5-HT3 receptor agonists (such as dolasetron, granisetron, ondansetron, tropisetron, palonosetron, and mirtazapine), dopamine agonists (such as domperidone, olanzapine, droperidol, haloperidol, chlorpromazine, prochlorperazine, alizapride, prochlorperazine, and metoclopramide), NK1 receptor antagonists (such as aprepitant and casopitant), antihistamines (such as cyclizine, diphenhydramine, dimenhydrinate, doxylamine, meclizine, promethazine, hydroxyzine), cannabinoids (such as cannabis, dronabinol, nabilone, and sativex), benzodiazepines (such as midazolam and lorazepam), anticholinergics (such as hyoscine), trimethobenzamide, ginger, emetrol, propofol, peppermint, muscimol, and ajwain.

Pharmaceutical compositions may be administered to a subject via any suitable route of administration. In one embodiment, the pharmaceutical composition is administered to a subject orally, parenterally, transdermally or transmucosally. In one embodiment, the pharmaceutical composition is administered to a subject parenterally. In one embodiment, the pharmaceutical composition is administered to a subject via a parenteral route of administration selected from the group consisting of intravenous (IV), subcutaneous (SC), and intramuscular (IM). In one embodiment, the pharmaceutical composition is administered to a subject via a route of administration selected from rectal and transdermal. In one embodiment, the pharmaceutical composition is administered to a subject in a dosage form selected from the group consisting of sterile solutions, suspensions, suppositories, tablets and capsules. In one embodiment, the pharmaceutical composition is administered to a subject in an oral dosage form selected from the group consisting of a tablet, caplet, capsule, lozenge, syrup, liquid, suspension and elixir. In one embodiment, the pharmaceutical composition is administered to a subject in an oral dosage form selected from the group consisting of tablets, hard shell capsules, soft gelatin capsules, beads, granules, aggregates, powders, gels, solids and semi-solids.

In some embodiments, the pharmaceutical composition is administered to a subject as a dosage form selected from the group consisting of sustained release forms, controlled release forms, delayed release forms and response release forms.

In some embodiments, the pharmaceutical composition is administered to a subject once daily. In some embodiments, the pharmaceutical composition is administered to a subject according to an infrequent dosing regimen (e.g., administered once per week or less frequently). In some embodiments, the pharmaceutical composition is administered to a subject according to a frequent dosing regimen (e.g., administered more than once per week). In some embodiments, the pharmaceutical composition is administered to a subject once weekly. In some embodiments, the pharmaceutical composition is administered to a subject once every four weeks. In some embodiments, the pharmaceutical composition is administered to a subject twice a week. In some embodiments, the pharmaceutical composition is administered to a subject once every two weeks. In some embodiments, the pharmaceutical composition is administered to a subject once every three weeks. In some embodiments, the pharmaceutical composition is administered to a subject in a repeated cycle of once weekly, once every two weeks, once every three weeks, once every four weeks or combinations thereof.

In one embodiment, the treatment method comprises administering to a subject in need of such treatment: (i) a first therapeutic agent including a compound comprising compound (1), compound (10) an analog thereof, or a pharmaceutically acceptable salt thereof in combination with (ii) a second therapeutic agent, wherein the first therapeutic agent and the second therapeutic agent are administered either simultaneously or sequentially; and further comprises assaying the expression of an endoplasmic reticulum (ER) stress response gene in a biological sample. In some embodiments, the endoplasmic reticulum stress response gene is selected from the group that includes, but is not limited to, C/EBP-Homologous Protein (CHOP), Activating Transcription Factor 3 (ATF3) and both CHOP and ATF3. In some embodiments, the endoplasmic reticulum stress response gene is selected from the group that includes, but is not limited to, ATF3, Activating Transcription Factor 4 (ATF4) CHOP, IRE1, Binding immunoglobulin protein (BiP), Eukaryotic translation initiation factor 2A (eIF2a), X-box binding protein 1 (XBP1). The biological sample may be tumor, peripheral blood mononuclear cells, or skin biopsy. The biological sample may be obtained before, during, or after drug administration. In some embodiments, the treatment method further comprises adjusting a dose of the first therapeutic agent to achieve induction of about 50%, 75%, 100%, 125%, 150%, 175%, 200%, 225%, 250%, 275%, 300%, 325%, 350%, 375%, 400%, 425%, 450%, 475%, 500%, 525%, 550%, 575%, 600%, or greater than 600% of one or more ER stress gene. In some embodiments, the treatment method further comprises adjusting a dose of the first therapeutic agent to achieve induction of about 50% to about 100%, about 100% to about 150%, about 150% to about 200%, about 200% to about 250%, about 250% to about 300%, about 300% to about 350%, about 350% to about 400%, about 400% to about 450%, about 450% to about 500%, about 500% to about 550%, about 550% to about 600%, or greater than 600% of ER stress genes. In some embodiments, the treatment method further comprises adjusting a dose of the first therapeutic agent to achieve induction of about 50% to about 100%, about 100% to about 200%, about 200% to about 300%, about 300% to about 400%, about 400% to about 500%, about 500% to about 600%, or greater than 600% of ER stress genes.

In one embodiment, the treatment method comprises administering to a subject in need of such treatment: (i) a first therapeutic agent including a compound comprising compound (1) or compound (10), an analog thereof, or a pharmaceutically acceptable salt thereof in combination with (ii) a second therapeutic agent, wherein the first therapeutic agent and the second therapeutic agent are administered either simultaneously or sequentially; and further comprises assaying the expression of proteasomal activity in a biological sample. In some embodiments the proteasomal activity may be chymotrysin-like, trypsin-like, and/or caspase-like activity. In some embodiments, the biological sample may be tumor, peripheral blood mononuclear cells, or skin cells. The biological sample may be obtained before, during, or after drug administration. In some embodiments, the treatment method further comprises adjusting the dose to achieve inhibition of about 20%, about 25%, about 30%, about 35%, about 40%, about 45%, about 50%, about 55%, about 60%, about 65%, about 70%, about 75%, about 80%, about 85%, about 90%, about 95%, or about 100% of the proteasomal activity. In some embodiments, the treatment method further comprises adjusting the dose to achieve inhibition of at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the proteasomal activity. In some embodiments, the treatment method further comprises adjusting the dose to achieve inhibition of about 20% to about 30%, about 30% to about 40%, about 40% to about 50%, about 50% to about 60%, about 60% to about 70%, about 70% to about 80%, about 80% to about 90%, or greater than 90% of the proteasomal activity.

In an aspect, provided herein are methods of treatment, which comprises administering to a subject in need of such treatment a combination of a first therapeutic agent including a compound of formula (1) or of formula (10), an analog thereof, or a pharmaceutically acceptable salt thereof (e.g., a di-salt or tri-salt) and a second therapeutic agent, the method comprising:

(i) administering to the subject the first therapeutic agent;

(ii) waiting until a predetermined waiting time has elapsed after the time of administration of the first therapeutic agent to the subject; and/or until adverse events are resolved or resolving; and (iii) administering the second therapeutic agent to the subject, wherein the predetermined waiting time is chosen so as to obtain a delayed therapeutic effect of the first therapeutic agent without an increased risk of possible combined toxic effects of the first and second therapeutic agents. In some embodiments of the treatment method, the predetermined waiting time is determined based on the clearance rate of the compound of the first therapeutic agent or a metabolite thereof. In some embodiments of the treatment method, the predetermined waiting time is determined by a quantitative assessment of renal function and parameters of renal. In some embodiments of the treatment method, the predetermined waiting time is determined by an assay for the determination of renal function, wherein the assay is selected from the group consisting of serum level the compound of the first therapeutic agent or a metabolite thereof; clearance rate of the compound of the first therapeutic agent or a metabolite thereof; 24-hour urinary clearance of the compound of the first therapeutic agent or a metabolite thereof.

In one embodiment of the treatment method, the predetermined waiting time substantially equals the time required for systemic clearance of the compound of the first therapeutic agent or a metabolite thereof from the subject's body. In one embodiment of the treatment method, the predetermined waiting time substantially equals the time required for renal clearance of the compound of the first therapeutic agent or a metabolite thereof from the subject's body. In one embodiment of the treatment method, the predetermined waiting time substantially equals the time required for hepatic clearance of the compound of the first therapeutic agent or a metabolite thereof from the subject's body. In one embodiment of the treatment method, the predetermined waiting time substantially equals the time required for total clearance of the compound of the first therapeutic agent or a metabolite thereof from the subject's body. In one embodiment of the treatment method, the predetermined waiting time is about 4 hours. In other embodiments the waiting time is 1 day. In some embodiments, the waiting time is until $C_{max}$ of the compound of the first therapeutic agent has passed. In other embodiments, the waiting time is after most of the adverse events are resolved or are resolving. In one embodiment of the treatment method, the predetermined waiting time is about 2 days, about 3 days, about 4 days, about 5 days, about 6 days, or about 7 days. In one embodiment of the treatment method, the predetermined waiting time is a range of about 1-7 days, about 1-6 days, about 1-5 days, about 1-4 days, about 1-3 days, or about 1 to 2 days. In one embodiment, the waiting time is up to 3 weeks. The preceeding are considered "therapeutic time periods."

When the order of administration is reversed, timing for the administration of the first therapeutic agent can be after the $C_{max}$ of the second therapeutic agent (i.e., the first administered drug) has passed. In one embodiment, administration of the first therapeutic agent can be after most or substantially all of the first administered drug has been eliminated from the body or the toxicity effects for the first administered drug are resolved or are resolving.

In some embodiments, the treatment method further comprises monitoring levels of the compound of the first therapeutic agent or a metabolite thereof in the subject using pharmacokinetic profiling. In some such embodiments, monitoring levels of the compound of the first therapeutic agent or a metabolite thereof in the subject using pharmacokinetic profiling comprises constructing a pharmacokinetic profile of the compound of the first therapeutic agent or a metabolite thereof for the subject using concentrations of the compound of the first therapeutic agent or a metabolite thereof in at least two samples obtained from the subject at time points suitable to construct a pharmacokinetic profile. In some embodiments of the method, which include monitoring levels of the compound of the first therapeutic agent or a metabolite thereof in the subject using pharmacokinetic profiling, samples are collected from the subject at point-of-care or point of use by sampling or self-sampling on point-of-care devices or point of use devices or on matrices suitable for storage of the samples prior to quantitation in a laboratory. In some embodiments of the treatment method, each of the point-of-care devices or point of use devices is capable of quantitating the compound of the first therapeutic agent or a metabolite thereof. In some embodiments of the method, which include monitoring levels of the compound of the first therapeutic agent or a metabolite thereof in the subject, one or more samples are collected from the subject at point-of-care or point of use by biopsy device for analysis at the point-of-care or point of use devices or for storage prior to analysis by a laboratory. In some embodiments of the method, a biopsy is taken after a time interval of 3-8 hours following administration the first therapeutic agent to the subject. In some embodiments of the method, a biopsy is taken after a time interval of 3-24 hours following administration of the first therapeutic agent to the subject. In some embodiments of the method, a biopsy is taken after a time interval of 8-24 hours following administration of the first therapeutic agent thereof to the subject. In some embodiments of the method, a biopsy is taken after a time interval of 2 days following administration of the first therapeutic agent to the subject. In some embodiments of the method, a biopsy is taken after a time interval of 3 days following administration of the first therapeutic agent to the subject. In some embodiments of the method, a biopsy is taken after a time interval of 4 days following administration of the first therapeutic agent to the subject. In some embodiments of the method, a biopsy is taken after a time interval of 1-7 days following administration of the first therapeutic agent.

In some embodiments of the treatment method, the pharmacokinetic profile includes pharmacokinetic parameters suitable for guiding dosing of the first therapeutic agent for the subject being treated. In some embodiments of the treatment method, maximum concentration of the first therapeutic agent in blood (whole blood, plasma, or serum) ("$C_{max}$") of the subject following its administration to the subject ranges from about 1000 ng/dL to 1500 ng/dL for a therapeutic time period. In some embodiments, $C_{max}$ is less than 1500 ng/dL and greater than 85 ng/dL for a therapeutic time period. In some embodiments of the treatment method, maximum concentration of the first therapeutic agent in blood (whole blood, plasma, or serum) ("$C_{max}$") of the subject following its administration to the subject ranges from about 1000 ng/mL to 1500 ng/mL for a therapeutic time period. In some embodiments, $C_{max}$ is less than 1500 ng/mL and greater than 85 ng/mL for a therapeutic time period.

In some embodiments, maximum concentration of the first therapeutic agent in blood (whole blood, plasma, or serum) ("$C_{max}$") of the subject following its administration to the subject is a $C_{max}$ of from about 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, or 1490 ng/dL to about 1500 ng/dL; from about 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 ng/dL to about 150 ng/dL; or from about 10, 10.5, 11, 11.5, 120, 12.5, 13, 13.5, 14, or 14.5 ng/dL to about 15 ng/dL.

In some embodiments, maximum concentration of the first therapeutic agent in blood (whole blood, plasma, or serum) ("$C_{max}$") of the subject following its administration is a $C_{max}$ of from about 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, or 1490 ng/mL to about 1500 ng/mL; from about 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 ng/mL to about 150 ng/mL; or from about 10, 10.5, 11, 11.5, 120, 12.5, 13, 13.5, 14, or 14.5 ng/mL to about 15 ng/mL.

In some embodiments, maximum concentration of the first therapeutic agent in blood (whole blood, plasma, or serum) ("$C_{max}$") of the subject following its administration is selected from about 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, or 1490 ng/dL. In some embodiments, maximum concentration of the first therapeutic agent in blood (whole blood, plasma, or serum) ("$C_{max}$") of the subject following its administration is selected from about 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 ng/dL. In some embodiments, maximum concentration of the first therapeutic agent in blood (whole blood, plasma, or serum) ("$C_{max}$") of the subject following its administration is selected from about 10, 10.5, 11, 11.5, 120, 12.5, 13, 13.5, 14, or 14.5 ng/dL.

In some embodiments, maximum concentration of the first therapeutic agent in blood (whole blood, plasma, or serum) ("$C_{max}$") of the subject following its administration is selected from about 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, or 1490 ng/mL. In some embodiments, maximum concentration of the first therapeutic agent in blood (whole blood, plasma, or serum) ("$C_{max}$") of the subject following its administration is selected from about 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 ng/mL. In some embodiments, maximum concentration of the first therapeutic agent in blood (whole blood, plasma, or serum) ("$C_{max}$") of the subject following its administration is selected from about 10, 10.5, 11, 11.5, 120, 12.5, 13, 13.5, 14, or 14.5 ng/mL.

In some embodiments, maximum concentration of the first therapeutic agent in blood (whole blood, plasma, or serum) ("$C_{max}$") of the subject following its administration is selected from about 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 385, 395, 405, 415, 425, 435, 445, 455, 465, 475, 485, 495, 505, 515, 525, 535, 545, 555, 565, 575, 585, 595, 605, 615, 625, 635, 645, 655, 665, 675, 685, 695, 705, 715, 725, 735, 745, 755, 765, 775, 785, 795, 805, 815, 825, 835, 845, 855, 865, 875, 885, 895, 905, 915, 925, 935, 945, 955, 965, 975, 985, 995, 1005, 1015, 1025, 1035, 1045, 1055, 1065, 1075, 1085, 1095, 1105, 1115, 1125, 1135, 1145, 1155, 1165, 1175, 1185, 1195, 1205, 1215, 1225, 1235, 1245, 1255, 1265, 1275, 1285, 1295, 1305, 1315, 1325, 1335, 1345, 1355, 1365, 1375, 1385, 1395, 1405, 1415, 1425, 1435, 1445, 1455, 1465, 1475, 1485, 1495, or 1500 ng/mL. In some embodiments, maximum concentration of the first therapeutic agent in blood (whole blood, plasma, or serum) ("$C_{max}$") of the subject following its administration is selected from about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 ng/mL. In some embodiments, maximum concentration of the first therapeutic agent in blood (whole blood, plasma, or serum) ("$C_{max}$") of the subject following its administration is selected from about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, or 14.5 ng/mL.

In some embodiments of the treatment method, the maximum concentration of the first therapeutic agent in blood (whole blood, plasma, or serum) ("$C_{max}$") of the subject following its administration to the subject ranges from about 85 ng/dL to 1500 ng/dL; from about 8.5 ng/dL to 150 ng/dL; or from about 0.85 ng/dL to 15 ng/dL. In some embodiments, maximum concentration of the first therapeutic agent in blood (whole blood, plasma, or serum) ("$C_{max}$") of the subject following its administration is selected from about 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 385, 395, 405, 415, 425, 435, 445, 455, 465, 475, 485, 495, 505, 515, 525, 535, 545, 555, 565, 575, 585, 595, 605, 615, 625, 635, 645, 655, 665, 675, 685, 695, 705, 715, 725, 735, 745, 755, 765, 775, 785, 795, 805, 815, 825, 835, 845, 855, 865, 875, 885, 895, 905, 915, 925, 935, 945, 955, 965, 975, 985, 995, 1005, 1015, 1025, 1035, 1045, 1055, 1065, 1075, 1085, 1095, 1105, 1115, 1125, 1135, 1145, 1155, 1165, 1175, 1185, 1195, 1205, 1215, 1225, 1235, 1245, 1255, 1265, 1275, 1285, 1295, 1305, 1315, 1325, 1335, 1345, 1355, 1365, 1375, 1385, 1395, 1405, 1415, 1425, 1435, 1445, 1455, 1465, 1475, 1485, or 1495 ng/dL to about 1500 ng/dL; from about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 ng/dL to about 150 ng/dL; or from about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, or 14.5 ng/dL to about 15 ng/dL.

In some embodiments of the treatment method, the maximum concentration of the first therapeutic agent in blood (whole blood, plasma, or serum) ("$C_{max}$") of the subject following its administration ranges from about 85 ng/mL to 1500 ng/mL; from about 8.5 ng/mL to 150 ng/mL; or from about 0.85 ng/mL to 15 ng/mL. In some embodiments, maximum concentration of the first therapeutic agent in blood (whole blood, plasma, or serum) ("$C_{max}$") of the subject following its administration is selected from about 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 385, 395, 405, 415, 425, 435, 445, 455, 465, 475, 485, 495, 505, 515, 525, 535, 545, 555, 565, 575, 585, 595, 605, 615, 625, 635, 645, 655, 665, 675, 685, 695, 705, 715, 725, 735, 745, 755, 765, 775, 785, 795, 805, 815, 825, 835, 845, 855, 865, 875, 885, 895, 905, 915, 925, 935, 945, 955, 965, 975, 985, 995, 1005, 1015, 1025, 1035, 1045, 1055, 1065, 1075, 1085, 1095, 1105, 1115, 1125, 1135, 1145, 1155, 1165, 1175, 1185, 1195, 1205, 1215, 1225, 1235, 1245, 1255, 1265, 1275, 1285, 1295, 1305, 1315, 1325, 1335, 1345, 1355, 1365, 1375, 1385, 1395, 1405, 1415, 1425, 1435, 1445, 1455, 1465, 1475, 1485, or 1495 ng/mL to about 1500 ng/mL; from about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 ng/mL to about 150 ng/mL; or from about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, or 14.5 ng/mL to about 15 ng/mL.

In some embodiments of the method, the total drug exposure over time, measured as the area under the curve ("AUC") of a plot of the concentration of the drug in blood (whole blood, plasma, or serum) of the subject following administration of the drug against time after administration of the drug ranges from about 150 ng hr/mL to about 8000 ng hr/mL; from about 15 ng hr/mL to about 800 ng hr/mL; or from about 1.5 ng hr/mL to about 80 ng hr/mL. In some embodiments, AUC is less than 8000 ng hr/mL and is greater than or equal to 150 ng hr/mL. In some embodiments, AUC is less than 800 ng hr/mL and is greater than or equal to 15 ng hr/mL. In some embodiments, AUC is less than 80 ng hr/mL and is greater than or equal to 1.5 ng hr/mL.

In some embodiments of the method, the total drug exposure over time is an AUC of from about 100 ng hr/mL to about 8000 ng hr/mL; from about 10 ng hr/mL to about 800 ng hr/mL; or from about 1 ng hr/mL to about 80 ng hr/mL. In some embodiments, the total drug exposure over time is an AUC of from about from about 150, 200, 400, 600, 800, 1000, 1200, 1400, 1600, 1800, 2000, 2200, 2400, 2600, 2800, 3000, 3200, 3400, 3600, 3800, 4000, 4200, 4400, 4600, 4800, 5000, 5200, 5400, 5600, 5800, 6000, 6200, 6400, 6600, 6800, 7000, 7200, 7400, 7600, or 7800 ng hr/mL to about 8000 ng hr/mL. In some embodiments, the total drug exposure over time is an AUC of from about 15, 20, 40, 60, 80, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, or 780 ng hr/mL to about 800 ng hr/mL. In some embodiments, the total drug exposure over time is an AUC of from about from about 1.5, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, or 78 ng hr/mL to about 80 ng hr/mL.

In some embodiments of the method the total drug exposure over time is an AUC of from about 100 ng hr/mL to about 8000 ng hr/mL, from about 10 ng hr/mL to about 800 ng hr/mL; or from about 1 ng hr/mL to about 80 ng hr/mL. In some embodiments, the total drug exposure over time is an AUC of from about from about 150 ng hr/mL to about 7800, 7600, 7400, 7200, 7000, 6800, 6600, 6400, 6200, 6000, 5800, 5600, 5400, 5200, 5000, 4800, 4600, 4400, 4200, 4000, 3800, 3600, 3400, 3200, 3000, 2800, 2600, 2400, 2200, 2000, 1800, 1600, 1400, 1200, 1000, 800, 600, 400, or 200 ng hr/mL. In some embodiments, the total drug exposure over time is an AUC of from about from about 15 ng hr/mL to about 780, 760, 740, 720, 700, 680, 660, 640, 620, 600, 580, 560, 540, 520, 500, 480, 460, 440, 420, 400, 380, 360, 340, 320, 300, 280, 260, 240, 220, 200, 180, 160, 140, 120, 100, 80, 60, 40, or 20 ng hr/mL. In some embodiments, the total drug exposure over time is an AUC of from about from about 1.5 ng hr/mL to about 78, 76, 74, 72, 70, 68, 66, 64, 62, 60, 58, 56, 54, 52, 50, 48, 46, 44, 42, 40, 38, 36, 34, 32, 30, 28, 26, 24, 22, 20, 18, 16, 14, 12, 10, 8, 6, 4, or 2 ng hr/mL. In some embodiments, the total drug exposure over time is an AUC of from about 100 ng hr/mL to about 200 ng hr/mL; from about 10 ng hr/mL to about 20 ng hr/mL; or from about 1 ng hr/mL to about 2 ng hr/mL.

In some embodiments of the method, the total drug exposure over time is an AUC selected from about 100, 150, 200, 400, 600, 800, 1000, 1200, 1400, 1600, 1800, 2000, 2200, 2400, 2600, 2800, 3000, 3200, 3400, 3600, 3800, 4000, 4200, 4400, 46000, 4800, 5000, 5200, 5400, 5600, 5800, 6000, 6200, 6400, 6600, 6800, 7000, 7200, 7400, 7600, 7800, and 8000 ng hr/mL. In some embodiments, the total drug exposure over time is an AUC selected from about 10, 15, 20, 40, 60, 80, 100, 120, 140, 160, 180, 200, 220, 240, 260, 280, 300, 320, 340, 360, 380, 400, 420, 440, 4600, 480, 500, 520, 540, 560, 580, 600, 620, 640, 660, 680, 700, 720, 740, 760, 780, and 800 ng hr/mL. In some embodiments of the method the total drug exposure over time is an AUC selected from about 1, 15, 2, 4, 6, 8, 10, 12, 14, 16, 18, 20, 22, 24, 26, 28, 30, 32, 34, 36, 38, 40, 42, 44, 460, 48, 50, 52, 54, 56, 58, 60, 62, 64, 66, 68, 70, 72, 74, 76, 78, and 80 ng hr/mL.

In another aspect, provided herein are methods of treatment, or use of a composition to treat a disease state, which comprises administering to a subject in need of such treatment a combination of a first therapeutic agent and a second therapeutic agent, the method comprising:

(i) administering to the subject the first therapeutic agent including a compound of formula (1) or of formula (10), an analog thereof, or a pharmaceutically acceptable salt thereof;

(ii) monitoring levels of the compound of the first therapeutic agent or a metabolite thereof in the subject using pharmacokinetic profiling; and (iii) administering the second therapeutic agent conditional on the level of the first therapeutic agent in the subject. In some embodiments of the method, the monitoring step includes constructing a pharmacokinetic profile of the compound of the first therapeutic agent or a metabolite thereof for the subject using concentrations of the compound of the first therapeutic agent or a metabolite thereof in a plurality of samples obtained from the subject at time points suitable to construct a pharmacokinetic profile. In some embodiments of the method, at least two samples are collected at point-of-care or point of use by sampling or self-sampling on point-of-care devices or point of use devices or on matrices suitable for storage of the samples prior to quantitation of the compound or a metabolite thereof by a laboratory. In some embodiments of the method, each point-of-care devices or point of use devices is capable of quantitating the compound or a metabolite thereof. In some embodiments of the method, the pharmacokinetic profile includes pharmacokinetic parameters suitable for guiding dosing of the compound or a salt thereof for the subject. In some embodiments of the method, the samples include from 2-12 samples. In some embodiments of the method, the samples are collected over a time period of up to 8 hours, up to 24 hours, up to 48 hours, or up to 72 hours. In some embodiments of the method, the pharmacokinetic parameters include at least one parameter selected from the group consisting of AUC, $AUC_{inf}$, $T_{max}$, $C_{max}$, time above threshold, steady state concentration, absorption rate, clearance rate, distribution rate, terminal T-1/2 or parameters drawn from noncompartmental pharmacokinetic (PK) or compartmental PK analysis, including physiological model-based compartmental PK analysis. In some embodiments of the method, the treatment method further comprises generating a report including the pharmacokinetic profile of the subject. In some embodiments of the method, the report includes a recommendation regarding dosing based on the pharmacokinetic profile of the subject. In some embodiments of the method, a reduction in dosage of compound (1), the analog thereof, or the pharmaceutically acceptable salt thereof is indicated to reduce risk of toxicity based on one or more pharmacokinetic parameters. In some embodiments of the method, the reduction in dosage of the compound or salt thereof is indicated based on time above threshold, wherein the threshold is the drug concentration above which toxicity occurs, or one or more of AUC, $AUC_{inf}$, mean residence time (MRT), exponentials defining the pharmacokinetic profile, volume of distribution at steady state (Vss), volume of distribution during the terminal phase (Vz) or combination of a group of pharmacokinetic variable to adequately describe the pharmacokinetic profile. In some embodiments of the method, a dose adjustment of the compound or salt thereof is indicated to increase efficacy based on one or more pharmacokinetic parameters. In some embodiments of the method, an increase in dosage of the compound or salt thereof is indicated based on one or more of AUC, $AUC_{inf}$, MRT, exponentials defining the pharmacokinetic profile, steady state volume (Vss) of distribution, volume of distribution during the terminal phase (Vz) or combination of a group of pharmacokinetic variables to adequately describe the pharmacokinetic profile. In some embodiments of the method, the dose of the compound or salt thereof is adjusted to within 5% to 25% of a desired target value. In some embodiments of the method, each of the samples is applied to the point-of-care device or the point of use device for determining the concentration of the compound or a metabolite thereof, wherein the point-of-care device or the point of use device comprises a lateral flow strip having a construction and composition such that an application of one or more of the samples to the lateral flow strip causes a fraction of the drug in the sample to bind to with a component of the lateral flow strip such that a detectable signal proportional to the concentration of the drug in the applied sample is produced. In some embodiments of the method, the samples are applied to matrices suitable for storage of the samples prior to quantitation by a laboratory. In some embodiments of the method, the samples are stored as dried blood spots. In some embodiments of the method, drug concentrations are measured by ELISA, LC MS MS, LC UV or LCMS. In some embodiments of the method, the pharmacokinetic parameters include at least one of steady state concentration, absorption, and terminal $T_{1/2}$. In some embodiments of the method, at least one of the samples is whole blood.

IX. MULTIMODAL THERAPEUTIC METHODS

In one aspect, provided herein are multimodal therapeutic methods in which administration of a compound of formula (1) or of formula (10), an analog thereof, or a pharmaceutically acceptable salt thereof to a subject in need of such treatment is supplemented by administration of other therapeutic modalities. In one embodiment, the multimodal therapeutic method comprises administering to a subject a pharmaceutical composition comprising a compound of formula (1) or of formula (10), an analog thereof, or a pharmaceutically acceptable salt thereof in conjunction with radiation therapy or after radiation is determined to not have been efficacious. In one embodiment, the multimodal therapeutic method comprises administering to a subject a pharmaceutical composition comprising a compound of formula (1) or of formula (10), an analog thereof, or a pharmaceutically acceptable salt thereof in conjunction with radiation therapy, wherein the pharmaceutical composition comprising the compound of formula (1) or of formula (10), an analog thereof, or a pharmaceutically acceptable salt thereof and the radiation therapy are administered concurrently or sequentially in any order. In one embodiment, the multimodal therapeutic method comprises administering to a subject a pharmaceutical composition comprising a compound of formula (1) or of formula (10), an analog thereof, or a pharmaceutically acceptable salt thereof in conjunction with radiation therapy in a sequential arrangement. In one embodiment, the multimodal therapeutic method comprises administering to a subject in need of such treatment a pharmaceutical composition comprising a compound of formula (1) or of formula (10), an analog thereof, or a pharmaceutically acceptable salt thereof thereof concurrently with radiation therapy. In one embodiment, the multimodal therapeutic method is used for the treatment of cancer. In one embodiment, the multimodal therapeutic method includes administering to a cancer subject in need of such treatment a pharmaceutical composition comprising a compound of formula (1) or of formula (10), an analog thereof, or a pharmaceutically acceptable salt thereof and irradiating cancer cells with a radiation beam. In one embodiment, the multimodal therapeutic method uses the technique of conformal radiotherapy (CRT) to deliver a dose volume histogram (DVH) prescribed to a cancer subject. In one embodiment, the multimodal therapeutic method uses the technique of intensity modulated radiation therapy (IMRT) to deliver radiation to cancer cells. In one embodiment, the multimodal therapeutic method uses techniques that compensate for motion of tumors in the subject during treatment (e.g., where doses of radiation must be administered to a thoracic tumor which moves as the patient breathes). For example, the multimodal therapeutic method use Four Dimensional Computed Tomography (4D CT) scanning techniques to adjust the delivered radiation field to compensate for tumor motion over the breathing cycle.

Any suitable type of radiation, including gamma radiation which is given fractionated, IMRT (intensity modulated radiation therapy), gamma knife, proton therapy and brachytherapy can be used with the multimodal therapeutic method. Radiation therapy and administering a compound of formula (1) or of formula (10), an analog thereof, or a pharmaceutically acceptable salt thereof can be used to treat brain tumors such as glioblastoma or disease that has metastasized to the brain from lung cancer. The multimodal therapeutic method can be used to treat lung cancer, pancreatic cancer, rectal cancer, breast cancer, sarcoma, prostate cancer, gynecological malignancies, and lymphoma. The gamma knife is used frequently to treat brain metastases. In one embodiment, the multimodal therapeutic method includes use of proton therapy to treat cancer, including brain tumors, prostate cancer and any tumor proximate vital organs where it is very important to minimize toxicity to nearby normal tissue.

In one embodiment, the multimodal therapeutic method includes administering to a cancer subject in need of such treatment a pharmaceutical composition comprising a compound of formula (1) or of formula (10), an analog thereof, or a pharmaceutically acceptable salt thereof in combination with adoptive cell therapy (e.g., CAR-T (JCAR 14, 15, 16, 17, KTE-C19, or CTL019); other T Cell (AFM13); or NK (CDNO-109 or NK-92)) either simultaneously or in combination.

In one embodiment, the multimodal therapeutic method eliminates minimal residual disease without adding to toxicity resulting from treatment by a compound of formula (1) or of formula (10), an analog thereof, or a pharmaceutically acceptable salt thereof. In one embodiment, the multimodal therapeutic method improves prognosis and/or reduces adverse side-effects associated with a disease state or condition in a subject undergoing treatment.

X. ADDITIONAL DERIVATIVES AND ANALOGS OF AND SALTS OF COMPOUND (1) AND RELATED COMPOUNDS

In one aspect, provided herein are analogs and related salts of compound (1) and processes of making the same. Persons skilled in the art will understand that the same general principles and concepts described above in conjunction with compounds (1), (10) and salts thereof, including principles and concepts related to methods and pharmaceutical compositions, apply with equal force to derivatives and analogs of and salts of compound (1) and salts thereof.

In one embodiment, the analogs have the structure of compound (25):

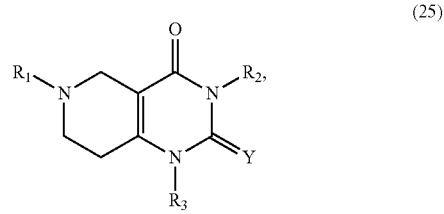

wherein Y represents $NR_4$ or O, and wherein $R_1$, $R_2$, $R_3$, and $R_4$ independently represent hydrogen, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In some embodiments, $R_1$, $R_2$, $R_3$, and $R_4$ are optionally substituted. In some embodiments, some or all hydrogens in $R_1$, $R_2$, $R_3$, and $R_4$ may be substituted by deuterium. In other embodiments, the analogs have the structure of compound (25), wherein $R_1$, $R_2$, $R_3$, and $R_4$ are independently selected from the group consisting of H, $C_{1-4}$alkyl, $C_{1-4}$alkylphenyl, $C_{1-4}$alkylphenylketone, $C_{1-4}$benzyl-piperazine, and $C_{1-4}$alkylthienyl wherein $C_{1-4}$alkyl, $C_{1-4}$alkylphenyl, $C_{1-4}$alkylphenylketone, and $C_{1-4}$benzyl-piperazine are optionally substituted with $C_{1-4}$alkyl, hydroxyl, or halo. In still other embodiments, the analogs have the structure of compound (25), wherein $R_1$, $R_2$, $R_3$, and $R_4$ are independently selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph.

In one embodiment, the analogs have the structure of compound (26):

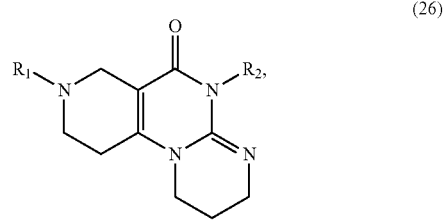

wherein $R_1$ and $R_2$ independently represent hydrogen, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In some embodiments, $R_1$ and $R_2$ are independently selected from the group consisting of H, $C_{1-4}$alkyl, $C_{1-4}$alkylphenyl, $C_{1-4}$alkylphenylketone, $C_{1-4}$benzyl-piperazine, and $C_{1-4}$alkylthienyl, wherein $C_{1-4}$alkyl, $C_{1-4}$alkylphenyl, $C_{1-4}$alkylphenylketone, and $C_{1-4}$benzyl-piperazine are optionally substituted with $C_{1-4}$alkyl, $C_{1-4}$alkoxyl, hydroxyl, perhalogenated $C_{1-4}$alkyl, or halo. In some embodiments, $R_1$ is selected from the group consisting of H, $CH_3$, $CH_2Ph$, $CH_2$-((2-Cl)-Ph), $CH_2$-(2- thienyl), CH$_2$CH$_2$Ph, CH$_2$CH$_2$(4-N-benzyl-piperazine), CH$_2$-(2,4-di F-Ph), CH$_2$-((2-CH$_3$)-Ph), CH$_2$CHOHPh, and (CH$_2$)$_3$CO-4F-Ph. In some embodiments, R$_2$ is selected from the group consisting of H, CH$_3$, CH$_2$Ph, CH$_2$-((2-Cl)-Ph), CH$_2$-(2-thienyl), CH$_2$CH$_2$Ph, CH2CH$_2$(4-N-benzyl-piperazine), CH$_2$-(2,4-di F-Ph), CH$_2$-((2-CH$_3$)-Ph), CH$_2$CHOHPh, and (CH$_2$)$_3$CO-4F-Ph.

In some embodiments, R$_1$ is a benzyl optionally substituted with one or more of the following substituents alone or in combination in the ortho, meta, and/or para positions of the benzyl ring: —CH$_3$, —NO$_2$, —OCH$_3$, —CXH$_2$, —CX$_2$H, —CX$_3$, —CH$_2$(CX$_3$), —CH(CX$_3$)$_2$, —C(CX$_3$)$_3$, —C$_p$X$_{2p+1}$, —OCX$_3$, or —OC$_p$X$_{2p+1}$, where p is an integer from 2 to 20 and where X represents a halogen including a fluorine, chlorine, bromine, or iodine atom, preferably, fluorine, chlorine, or bromine, more preferably, fluorine or chlorine. In some embodiments, R$_2$ is a benzyl substituted with one or more of the following substituents alone or in combination in the ortho, meta, and/or para positions of the benzyl ring: —CH$_3$, —NO$_2$, —OCH$_3$, —CXH$_2$, —CX$_2$H, —CX$_3$, —CH$_2$(CX$_3$), —CH(CX$_3$)$_2$, —C(CX$_3$)$_3$, —C$_p$X$_{2p+1}$, —OCX$_3$, or —OC$_p$X$_{2p+1}$, where p is an integer from 2 to 20 and where X represents a halogen.

In some embodiments, R$_1$ is a hydrogen. In some embodiments, R$_1$ is a substituted or an unsubstituted arylalkyl, such as a benzyl or phenylethyl group. In some embodiments, the arylalkyl is substituted with C$_{1-4}$alkyl, C$_{1-4}$alkoxyl, hydroxyl, perhalogenated C$_{1-4}$alkyl, or halo.

In some embodiments, R$_2$ is a substituted or an unsubstituted arylalkyl, such as a benzyl or phenylethyl group. In some embodiments, the arylalkyl is substituted with C$_{1-4}$alkyl, C$_{1-4}$alkoxyl, hydroxyl, perhalogenated C$_{1-4}$alkyl, or halo. In some embodiments, the arylalkyl is substituted with one or more substituents selected from the group consisting of halo, —CH$_3$, —CF$_3$, and —OCH$_3$. In some embodiments, R$_2$ is a substituted or an unsubstituted heterocycloalkylalkyl, such as a morpholinoalkyl or piperazinylalkyl group. In some embodiments, R$_2$ is a substituted or an unsubstituted heteroarylalkyl, such as an isoxazolidinyl-methyl or pyridylmethyl group. In some embodiments, the heterocycloalkylalkyl or heteroarylalkyl is substituted with C$_{1-4}$alkyl, C$_{1-4}$alkoxyl, hydroxyl, perhalogenated C$_{1-4}$alkyl, or halo. In some embodiments, the heterocycloalkylalkyl or heteroarylalkyl is substituted with one or more substituents selected from the group consisting of halo, —CH$_3$, —CF$_3$, and —OCH$_3$.

In one embodiment, the analogs have the structure of compound (27):

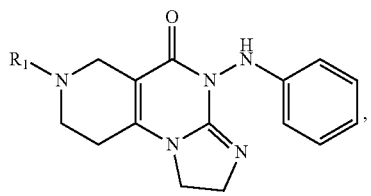

(27)

wherein R$_1$ represents hydrogen, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In some embodiments, R$_1$ is selected from the group consisting of H, C$_{1-4}$alkyl, C$_{1-4}$alkylphenyl, C$_{1-4}$alkylphenylketone, C$_{1-4}$benzyl-piperazine, and C$_{1-4}$alkylthienyl, wherein C$_{1-4}$alkyl, C$_{1-4}$alkylphenyl, C$_{1-4}$alkylphenylketone, and C$_{1-4}$benzyl-piperazine are optionally substituted with C$_{1-4}$alkyl, C$_{1-4}$alkoxyl, hydroxyl, perhalogenated C$_{1-4}$alkyl, or halo. In some embodiments, R$_1$ is selected from the group consisting of H, CH$_3$, CH$_2$Ph, CH$_2$-((2-Cl)-Ph), CH$_2$-(2-thienyl), CH$_2$CH$_2$Ph, CH$_2$CH$_2$(4-N-benzyl-piperazine), CH$_2$-(2,4-di F-Ph), CH$_2$-((2-CH$_3$)-Ph), CH$_2$CHOHPh, and (CH$_2$)$_3$CO-4F-Ph.

In some embodiments, R$_1$ is a benzyl optionally substituted with one or more of the following substituents alone or in combination in the ortho, meta, and/or para positions of the benzyl ring: —CH$_3$, —NO$_2$, —OCH$_3$, —CXH$_2$, —CX$_2$H, —CX$_3$, —CH$_2$(CX$_3$), —CH(CX$_3$)$_2$, —C(CX$_3$)$_3$, —C$_p$X$_{2p+1}$, —OCX$_3$, or —OC$_p$X$_{2p+1}$, where p is an integer from 2 to 20 and where X represents a halogen including a fluorine, chlorine, bromine, or iodine atom, preferably, fluorine, chlorine, or bromine, more preferably, fluorine or chlorine. In some embodiments, R$_1$ is a hydrogen. In some embodiments, R$_1$ is a substituted or an unsubstituted arylalkyl, such as a benzyl or phenylethyl group. In some embodiments, the arylalkyl is substituted with C$_{1-4}$alkyl, C$_{1-4}$alkoxyl, hydroxyl, perhalogenated C$_{1-4}$alkyl, or halo.

In one embodiment, the analogs have the structure of compound (28):

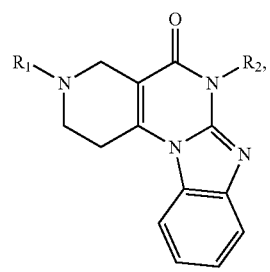

(28)

wherein R$_1$ and R$_2$ independently represent hydrogen, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In some embodiments, R$_1$ and R$_2$ are independently selected from the group consisting of H, C$_{1-4}$alkyl, C$_{1-4}$alkylphenyl, C$_{1-4}$alkylphenylketone, C$_{1-4}$benzyl-piperazine, and C$_{1-4}$alkylthienyl, wherein C$_{1-4}$alkyl, C$_{1-4}$alkylphenyl, C$_{1-4}$alkylphenylketone, and C$_{1-4}$benzyl-piperazine are optionally substituted with C$_{1-4}$alkyl, C$_{1-4}$alkoxyl, hydroxyl, perhalogenated C$_{1-4}$alkyl, or halo. In some embodiments, R$_1$ is selected from the group consisting of H, CH$_3$, CH$_2$Ph, CH$_2$-((2-Cl)-Ph), CH$_2$-(2-thienyl), CH$_2$CH$_2$Ph, CH$_2$-(2,4-di F-Ph), CH$_2$-((2-CH$_3$)-Ph), CH$_2$CHOHPh, CH$_2$CH$_2$(4-N-benzyl-piperazine), and (CH$_2$)$_3$CO-4F-Ph. In some embodiments, R$_2$ is selected from the group consisting of H, CH$_3$, CH$_2$Ph, CH$_2$-((2-Cl)-Ph), CH$_2$-(2-thienyl), CH$_2$CH$_2$Ph, CH$_2$CH$_2$(4-N-benzyl-piperazine), CH$_2$-(2,4-di F-Ph), CH$_2$-((2-CH$_3$)-Ph), CH$_2$CHOHPh, and (CH$_2$)$_3$CO-4F-Ph. In some embodiments, when R$_1$ represents CH$_2$Ph, R$_2$ does not represent CH$_2$-((2-CH$_3$)-Ph).

In some embodiments, R$_1$ is a benzyl optionally substituted with one or more of the following substituents alone or in combination in the ortho, meta, and/or para positions of the benzyl ring: —$CH_3$, —$NO_2$, —$OCH_3$, —$CXH_2$, —$CX_2H$, —$CX_3$, —$CH_2(CX_3)$, —$CH(CX_3)_2$, —$C(CX_3)_3$, —$C_pX_{2p+1}$, —$OCX_3$, or —$OC_pX_{2p+1}$, where p is an integer from 2 to 20 and where X represents a halogen including a fluorine, chlorine, bromine, or iodine atom, preferably, fluorine, chlorine, or bromine, more preferably, fluorine or chlorine. In some embodiments, $R_2$ is a benzyl substituted with one or more of the following substituents alone or in combination in the ortho, meta, and/or para positions of the benzyl ring: —$CH_3$, —$NO_2$, —$OCH_3$, —$CXH_2$, —$CX_2H$, —$CX_3$, —$CH_2(CX_3)$, —$CH(CX_3)_2$, —$C(CX_3)_3$, —$C_pX_{2p+1}$, —$OCX_3$, or —$OC_pX_{2p+1}$, where p is an integer from 2 to 20 and where X represents a halogen.

In some embodiments, $R_1$ is a hydrogen. In some embodiments, $R_1$ is a substituted or an unsubstituted arylalkyl, such as a benzyl or phenylethyl group. In some embodiments, the arylalkyl is substituted with $C_{1-4}$alkyl, $C_{1-4}$alkoxyl, hydroxyl, perhalogenated $C_{1-4}$alkyl, or halo.

In some embodiments, $R_2$ is a substituted or an unsubstituted arylalkyl, such as a benzyl or phenylethyl group. In some embodiments, the arylalkyl is substituted with $C_{1-4}$alkyl, $C_{1-4}$alkoxyl, hydroxyl, perhalogenated $C_{1-4}$alkyl, or halo. In some embodiments, the arylalkyl is substituted with one or more substituents selected from the group consisting of halo, —$CH_3$, —$CF_3$, and —$OCH_3$. In some embodiments, $R_2$ is a substituted or an unsubstituted heterocycloalkylalkyl, such as a morpholinoalkyl or piperazinylalkyl group. In some embodiments, $R_2$ is a substituted or an unsubstituted heteroarylalkyl, such as an isoxazolidinylmethyl or pyridylmethyl group. In some embodiments, the heterocycloalkylalkyl or heteroarylalkyl is substituted with $C_{1-4}$alkyl, $C_{1-4}$alkoxyl, hydroxyl, perhalogenated $C_{1-4}$alkyl, or halo. In some embodiments, the heterocycloalkylalkyl or heteroarylalkyl is substituted with one or more substituents selected from the group consisting of halo, —$CH_3$, —$CF_3$, and —$OCH_3$.

In one embodiment, the analogs have the structure of compound (29):

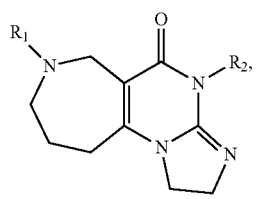

(29)

wherein $R_1$ and $R_2$ independently represent hydrogen, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In some embodiments, $R_1$ and $R_2$ are independently selected from the group consisting of H, $C_{1-4}$alkyl, $C_{1-4}$alkylphenyl, $C_{1-4}$alkylphenylketone, $C_{1-4}$benzyl-piperazine, and $C_{1-4}$alkylthienyl, wherein $C_{1-4}$alkyl, $C_{1-4}$alkylphenyl, $C_{1-4}$alkylphenylketone, and $C_{1-4}$benzyl-piperazine are optionally substituted with $C_{1-4}$alkyl, $C_{1-4}$alkoxyl, hydroxyl, perhalogenated $C_{1-4}$alkyl, or halo. In some embodiments, $R_1$ is selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph. In some embodiments, $R_2$ is selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph. In some embodiments, when $R_1$ represents $CH_2Ph$, $R_2$ does not represent $CH_2$-((2-$CH_3$)-Ph).

In some embodiments, $R_1$ is a benzyl optionally substituted with one or more of the following substituents alone or in combination in the ortho, meta, and/or para positions of the benzyl ring: —$CH_3$, —$NO_2$, —$OCH_3$, —$CXH_2$, —$CX_2H$, —$CX_3$, —$CH_2(CX_3)$, —$CH(CX_3)_2$, —$C(CX_3)_3$, —$C_pX_{2p+1}$, —$OCX_3$, or —$OC_pX_{2p+1}$, where p is an integer from 2 to 20 and where X represents a halogen including refers to a fluorine, chlorine, bromine, or iodine atom, preferably, fluorine, chlorine, or bromine, more preferably, fluorine or chlorine. In some embodiments, $R_2$ is a benzyl substituted with one or more of the following substituents alone or in combination in the ortho, meta, and/or para positions of the benzyl ring: —$CH_3$, —$NO_2$, —$OCH_3$, —$CXH_2$, —$CX_2H$, —$CX_3$, —$CH_2(CX_3)$, —$CH(CX_3)_2$, —$C(CX_3)_3$, —$C_pX_{2p+1}$, —$OCX_3$, or —$OC_pX_{2p+1}$, where p is an integer from 2 to 20 and where X represents a halogen.

In some embodiments, $R_1$ is a hydrogen. In some embodiments, $R_1$ is a substituted or an unsubstituted arylalkyl, such as a benzyl or phenylethyl group. In some embodiments, the arylalkyl is substituted with $C_{1-4}$alkyl, $C_{1-4}$alkoxyl, hydroxyl, perhalogenated $C_{1-4}$alkyl, or halo.

In some embodiments, $R_2$ is a substituted or an unsubstituted arylalkyl, such as a benzyl or phenylethyl group. In some embodiments, the arylalkyl is substituted with $C_{1-4}$alkoxyl, $C_{1-4}$alkoxyl, hydroxyl, perhalogenated $C_{1-4}$alkyl, or halo. In some embodiments, the arylalkyl is substituted with one or more substituents selected from the group consisting of halo, —$CH_3$, —$CF_3$, and —$OCH_3$. In some embodiments, $R_2$ is a substituted or an unsubstituted heterocycloalkylalkyl, such as a morpholinoalkyl or piperazinylalkyl group. In some embodiments, $R_2$ is a substituted or an unsubstituted heteroarylalkyl, such as an isoxazolidinylmethyl or pyridylmethyl group. In some embodiments, the heterocycloalkylalkyl or heteroarylalkyl is substituted with $C_{1-4}$alkyl, $C_{1-4}$alkoxyl, hydroxyl, perhalogenated $C_{1-4}$alkyl, or halo. In some embodiments, the heterocycloalkylalkyl or heteroarylalkyl is substituted with one or more substituents selected from the group consisting of halo, —$CH_3$, —$CF_3$, and —$OCH_3$.

In one embodiment, the analogs have the structure of compound (30):

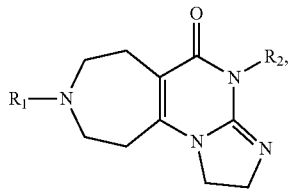

(30)

wherein $R_1$ and $R_2$ independently represent hydrogen, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In some embodiments, $R_1$ and $R_2$ are independently selected from the group consisting of H, $C_{1-4}$alkyl, $C_{1-4}$alkylphenyl, $C_{1-4}$alkylphenylketone, $C_{1-4}$benzyl-piperazine, and $C_{1-4}$alkylthienyl, wherein $C_{1-4}$alkyl, $C_{1-4}$alkylphenyl, $C_{1-4}$alkylphenylketone, and $C_{1-4}$benzyl-piperazine are optionally substituted with $C_{1-4}$alkyl, $C_{1-4}$alkoxyl, hydroxyl, perhalogenated $C_{1-4}$alkyl, or halo. In some embodiments, $R_1$ is selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph. In some embodiments, $R_2$ is selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph. In some embodiments, when $R_1$ represents $CH_2Ph$, $R_2$ does not represent $CH_2$-((2-$CH_3$)-Ph).

In some embodiments, $R_1$ is a benzyl optionally substituted with one or more of the following substituents alone or in combination in the ortho, meta, and/or para positions of the benzyl ring: —$CH_3$, —$NO_2$, —$OCH_3$, —$CXH_2$, —$CX_2H$, —$CX_3$, —$CH_2(CX_3)$, —$CH(CX_3)_2$, —$C(CX_3)_3$, —$C_pX_{2p+1}$, —$OCX_3$, or —$OC_pX_{2p+1}$, where p is an integer from 2 to 20 and where X represents a halogen including refers to a fluorine, chlorine, bromine, or iodine atom, preferably, fluorine, chlorine, or bromine, more preferably, fluorine or chlorine. In some embodiments, $R_2$ is a benzyl substituted with one or more of the following substituents alone or in combination in the ortho, meta, and/or para positions of the benzyl ring: —$CH_3$, —$NO_2$, —$OCH_3$, —$CXH_2$, —$CX_2H$, —$CX_3$, —$CH_2(CX_3)$, —$CH(CX_3)_2$, —$C(CX_3)_3$, —$C_pX_{2p+1}$, —$OCX_3$, or —$OC_pX_{p+1}$, where p is an integer from 2 to 20 and where X represents a halogen.

In some embodiments, $R_1$ is a hydrogen. In some embodiments, $R_1$ is a substituted or an unsubstituted arylalkyl, such as a benzyl or phenylethyl group. In some embodiments, the arylalkyl is substituted with $C_{1-4}$alkyl, $C_{1-4}$alkoxyl, hydroxyl, perhalogenated $C_{1-4}$alkyl, or halo.

In some embodiments, $R_2$ is a substituted or an unsubstituted arylalkyl, such as a benzyl or phenylethyl group. In some embodiments, the arylalkyl is substituted with $C_{1-4}$alkyl, $C_{1-4}$alkoxyl, hydroxyl, perhalogenated $C_{1-4}$alkyl, or halo. In some embodiments, the arylalkyl is substituted with one or more substituents selected from the group consisting of halo, —$CH_3$, —$CF_3$, and —$OCH_3$. In some embodiments, $R_2$ is a substituted or an unsubstituted heterocycloalkylalkyl, such as a morpholinoalkyl or piperazinylalkyl group. In some embodiments, $R_2$ is a substituted or an unsubstituted heteroarylalkyl, such as an isoxazolidinylmethyl or pyridylmethyl group. In some embodiments, the heterocycloalkylalkyl or heteroarylalkyl is substituted with $C_{1-4}$alkyl, $C_{1-4}$alkoxyl, hydroxyl, perhalogenated $C_{1-4}$alkyl, or halo. In some embodiments, the heterocycloalkylalkyl or heteroarylalkyl is substituted with one or more substituents selected from the group consisting of halo, —$CH_3$, —$CF_3$, and —$OCH_3$.

In one embodiment, the analogs have the structure of compound (31):

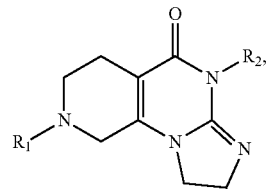

(31)

wherein $R_1$ and $R_2$ independently represent hydrogen, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In some embodiments, $R_1$ and $R_2$ are independently selected from the group consisting of H, $C_{1-4}$alkyl, $C_{1-4}$alkylphenyl, $C_{1-4}$alkylphenylketone, $C_{1-4}$benzyl-piperazine, and $C_{1-4}$alkylthienyl, wherein $C_{1-4}$alkyl, $C_{1-4}$alkylphenyl, $C_{1-4}$alkylphenylketone, and $C_{1-4}$benzyl-piperazine are optionally substituted with $C_{1-4}$alkyl, $C_{1-4}$alkoxyl, hydroxyl, perhalogenated $C_{1-4}$alkyl, or halo. In some embodiments, $R_1$ is selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph. In some embodiments, $R_2$ is selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph. In some embodiments, when $R_1$ represents $CH_2Ph$, $R_2$ does not represent $CH_2$-((2-$CH_3$)-Ph).

In some embodiments, $R_1$ is a benzyl optionally substituted with one or more of the following substituents alone or in combination in the ortho, meta, and/or para positions of the benzyl ring: —$CH_3$, —$NO_2$, —$OCH_3$, —$CXH_2$, —$CX_2H$, —$CX_3$, —$CH_2(CX_3)$, —$CH(CX_3)_2$, —$C(CX_3)_3$, —$C_pX_{2p+1}$, —$OCX_3$, or —$OC_pX_{2p+1}$, where p is an integer from 2 to 20 and where X represents a halogen including refers to a fluorine, chlorine, bromine, or iodine atom, preferably, fluorine, chlorine, or bromine, more preferably, fluorine or chlorine. In some embodiments, $R_2$ is a benzyl substituted with one or more of the following substituents alone or in combination in the ortho, meta, and/or para positions of the benzyl ring: —$CH_3$, —$NO_2$, —$OCH_3$, —$CXH_2$, —$CX_2H$, —$CX_3$, —$CH_2(CX_3)$, —$CH(CX_3)_2$, —$C(CX_3)_3$, —$C_pX_{2p+1}$, —$OCX_3$, or —$OC_pX_{2p+1}$, where p is an integer from 2 to 20 and where X represents a halogen.

In some embodiments, $R_1$ is a hydrogen. In some embodiments, $R_1$ is a substituted or an unsubstituted arylalkyl, such as a benzyl or phenylethyl group. In some embodiments, the arylalkyl is substituted with $C_{1-4}$alkyl, $C_{1-4}$alkoxyl, hydroxyl, perhalogenated $C_{1-4}$alkyl, or halo.

In some embodiments, $R_2$ is a substituted or an unsubstituted arylalkyl, such as a benzyl or phenylethyl group. In some embodiments, the arylalkyl is substituted with $C_{1-4}$alkyl, $C_{1-4}$alkoxyl, hydroxyl, perhalogenated $C_{1-4}$alkyl, or halo. In some embodiments, the arylalkyl is substituted with one or more substituents selected from the group consisting of halo, —$CH_3$, —$CF_3$, and —$OCH_3$. In some embodiments, $R_2$ is a substituted or an unsubstituted heterocycloalkylalkyl, such as a morpholinoalkyl or piperazinylalkyl group. In some embodiments, $R_2$ is a substituted or an unsubstituted heteroarylalkyl, such as an isoxazolidinylmethyl or pyridylmethyl group. In some embodiments, the heterocycloalkylalkyl or heteroarylalkyl is substituted with $C_{1-4}$alkyl, $C_{1-4}$alkoxyl, hydroxyl, perhalogenated $C_{1-4}$alkyl, or halo. In some embodiments, the heterocycloalkylalkyl or heteroarylalkyl is substituted with one or more substituents selected from the group consisting of halo, —$CH_3$, —$CF_3$, and —$OCH_3$.

XI. EXAMPLES

It should be understood that the description and specific examples provided below are intended for purposes of illustration only and are not intended to limit the scope of the present disclosure. The following examples are intended to illustrate the embodiments disclosed and are not to be construed as being limitations thereto. Additional compounds, other than those described below, may be prepared using the following reaction schemes described above or appropriate variations or modifications thereof.

Example 1. Synthesis of 2-Chlorobenzylamino-2-imidazoline hydriodide

To a stirred solution of 2-methylthio-2-imidazoline hydriodide (244 mg, 1.00 mMol) in dry dioxane (2.0 mL) was added 2-chlorobenzylamine (141 mg, 1.0 mMol). The reaction mixture was stirred for 90 min at 70 C. under an atmosphere of argon. The solution was cooled to room temperature, filtered on a sintered funnel, washed with cold dioxane (2 mL) and dried under vacuum. The white solid compound 4.HI ($R_2$=2-chlorobenzyl) was obtained (242 mg, 72%) and used without further purification.

Example 2. Synthesis of 2-Chlorobenzylamino-2-imidazoline

To a stirred solution of 2-chlorobenzylamino-2-imidazoline hydriodide (242 mg, 0.72 mMol) in water (3 mL), was added 1.0 N sodium hydroxide (2 mL) at 7° C. The reaction mixture was stirred for 30 min at 7° C. under argon. After that methylene chloride (5 mL) was added and the mixture stirred for another 5 min. The reaction mixture was extracted with methylene chloride (2×2.5 mL), The organic layer was dried over anhydrous $Na_2SO_4$, filtered and evaporated. The resulting free base (150 mg, 100%) was obtained as a viscous liquid and was used for the next reaction without any further purification. MS(ESI) 210(M+H).

Example 3. Synthesis of Methyl-1-benzyl 4-oxo-3-piperidine carboxylate (Compound (6))

To a stirred methyl-1-benzyl 4-oxo-3-piperidine carboxylate hydrochloride (5.7 g, 20 mMol) in ethyl acetate (50 mL), was added triethylamine (6 mL) at 7° C. The reaction mixture was stirred for 30 min at 7° C. under atmosphere of argon. The reaction mixture was extracted with ethyl acetate (2×50 mL) washed with water (50 mL). The organic layer was dried over anhydrous $Na_2SO_4$, filtered and evaporated. The resulting free base residue (5, $R_1$=benzyl) as a viscous oil was used in the next reaction without any further purification MS(ESI) 248(M+H).

Example 4. Synthesis of ONC902 (Compound (14)

To a solution of 2-chlorobenzylamino-2-imidazoline (150 mg, 0.72 mMol), methyl 1-benzyl 4-oxo-3-piperidine carboxylate (5, $R_1$=benzyl) (195 mg, 0.79 mMol) in 1-butanol (2 mL) was added PPTS (10 mg) and the mixture was stirred at room temperature for 48 h. After that the reaction mixture was refluxed at 125° C. to 130° C. for 2 h. The solvents were removed under vacuum, extracted with ethyl acetate (10 mL), washed with saturated sodium bicarbonate solution (2×10 mL) and water (10 mL). The organic layer was dried over anhydrous $Na_2SO_4$, filtered and evaporated. The crude free base was purified by RP HPLC (10%-40% acetonitrile/water) to give ONC902 TFA salt as a white solid (228 mg, 50% yield) MS(ESI) 407 (M+H).

The same process was used starting with different benzylamines to prepare various analogs, e.g., ONC903, 904, 905, 906, 912, 210, 211, 212, 213, 214, 217, 218, 219, 220, 221, 222, 223, 224, 225, and 226.

Example 5. Synthesis of ONC907 (Compound (19)

To a suspension of 60% sodium hydride (3.5 g, 88 mMol) in dry toluene (50 mL), dimethyl carbonate (4.32 g, 48.0 mMol) was added dropwise in 0.5 h at room temperature under an atmosphere of nitrogen. After addition of a few drops of methanol, a solution of 1-text-butoxycarbonyl-4-piperidone (4.8 g, 24 mMol) dissolved in dry toluene (20 mL) was added dropwise to the reaction mixture while stirring at 80° C. over 1h. The reaction mixture was stirred for 3 h at the same temperature and then cooled to 0° C. (ice bath) and adjusted to pH 6-6.5 with acetic acid. The resulting cold mixture was diluted with water (10 mL) and adjusted to pH 8 with 5% sodium hydroxide solution. The toluene layer was separated and the aqueous layer was extracted with toluene (20 mL). The combined organic layer was dried over anhydrous sodium sulfate, and concentrated under reduced pressure The compound was dried in vacuum to give methyl-1-tert-butoxycarbonyl-4-oxo-3-piperidine carboxylate (5.0 g, 80%). The compound obtained was carried to next reaction without any further purification.

2-methybenzylamino-2-imidazoline (190 mg, 1 mMol), methyl 1-tert-butoxycarbonyl-4-oxo-3-piperidine carboxylate (315 mg, 1.1 mMol) in 1-butanol (2 mL) was added PPTS (10.0 mg) and the mixture was stirred at room temperature for 48 h. After that the reaction mixture was refluxed at 125° C. to 130° C. for 2h. The solvents were removed under vacuum, extracted with ethyl acetate (10 mL), washed with saturated sodium bicarbonate solution (2×10 mL) and water (10 mL). The organic layer was dried over anhydrous $Na_2SO_4$, filtered and evaporated. The crude free base was cleaved with 10% trifluoroacetic acid in dichloromethane, purified by RP HPLC (10%-40% acetonitrile/water) to give ONC907 (262 mg, 50%) TFA salt as a white solid MS(ESI) 297 (M+H).

Example 6. Synthesis of ONC909 (Compound (21)

A mixture of ONC907 (100 mg, 0.2 mMol), phenylethyl bromide (55.0 mg, 0.28 mMol) and potassium carbonate (150 mg, 1.0 mMol) in N,N-dimethylformamide (3 mL) was heated to 70° C. for 12 h. The solvents were removed under vacuum, extracted with ethyl acetate (10 mL), washed with water (5 mL). The organic layer was dried over anhydrous $Na_2SO_4$, filtered and evaporated. The crude free base was purified by RP HPLC (10%-40% acetonitrile/water) to give ONC909 (62 mg, 50%) TFA salt as a white solid MS(ESI) 401 (M+H).

The same process was used starting with different halides to give ONC910 and 214. Compounds 227, 228, 229, 230, 231, 232, 233, 234, 235, and 236 were prepared using the analogous process from Examples 1 and 5 starting with a different benzylamine. Then treating the intermediate compound where $R_1$ is H with different halides as above.

Compound ONC911 was prepared from ONC910 by treatment with TFA.

Compound (72) was prepared by reacting the precursor NH compound prepared in analogy to Example 5 and treating it with styrene oxide.

Example 7. Synthesis of ONC908 (Compound (20)

To a solution of 2-methylbenzylamino-2-imidazoline (190.0 mg, 1.0 mmol), methyl 1-methyl 4-oxo-3-piperidine carboxylate (185.0 mg, 1.0 mMol) in 1-butanol (2.0 mL) was added PPTS (10.0 mg) and the mixture was stirred at room temperature for 48 h. After that the reaction mixture was refluxed at 125° C. to 130° C. for 2h. The solvents were removed under vacuum, extracted with ethyl acetate (10 mL), washed with saturated sodium bicarbonate solution (2×10 mL) and water (10 mL). The organic layer was dried over anhydrous $Na_2SO_4$, filtered and evaporated. The crude free base was purified by HPLC 10%-40% acetonitrile and water to give ONC908 (270.0 mg, 50%) TFA salt as a white solid MS(ESI) 311 (M+H).

Example 8. Synthesis of ONC201 (Compound (1)

To a stirred 800 mL saturated $NaHCO_3$ in a 2 L round bottom flask, compound (3) (239.7 g, 0.845 mol, 1.6 equiv) was added in portions. n-Butanol (500 mL) was added to the resulting mixture and the mixture was stirred for 30 min and then transferred to a separating funnel. The organic phase, containing compound (4), was separated and transferred to a 2 L three-neck round bottom flask equipped with mechanical stirring, $N_2$ inlet, a thermocouple, a condenser and a Dean-Stark trap. Compound (5) (100 g, 0.528 mol, 1 equiv) and pyridinium p-toluenesulfonate (PPTS) (6.63 gm 0.026 mol, 5 mol %) were added to the contents of the flask. The resulting mixture was heated to reflux for 6 hours. Water in the reaction mixture was separated into the Dean-Stark trap as necessary. Refluxing temperature increased from 93° C. to 118° C. Reaction progress was monitored by HPLC. When the peak area of compound (1) on HPLC remained constant with the reaction time, the reaction was stopped.

Example 9. Synthesis of Di-Salt of ONC201 (Compound (1).2HCl)

Without isolation of the compound (1), the reaction mixture from Example 8 was washed with 500 mL of water and diluted with methyl tert-butyl ether (MTBE) (800 mL). The organic phase was washed with water (500 mL×2) and transferred to a 3 L three-neck round bottom flask equipped with mechanical stirring, $N_2$ inlet, a thermocouple, a condenser and a Dean-Stark trap. While agitating the reaction mixture, 1 N HCl in dioxane-MTBE solution was added dropwise (4 N HCl in dioxane: 300 mL, 1.2 mol, 2.27 equiv; MTBE: 1200 mL) until no more solid precipitated out of the reaction mixture upon addition of HCl. The reaction mixture was heated to reflux at 60-65° C. for 2 hours. Water was separated into the Dean-Stark trap as necessary. Upon cooling to room temperature, the solid precipitate was filtered through a sintered glass funnel and washed with n-butanol-MTBE (1:2, 600 mL) and MTBE (600 mL) respectively. The solid was dried in the vacuum oven at 65° C. overnight (16 hours) to afford 200 g yellow solid.

To a 2 L three-neck round bottom flask equipped with mechanical stirring, N2 inlet, a thermocouple and a condenser, the above solid (200 g) was added, followed by ethanol (1000 mL). The mixture was heated to reflux at 78° C. for 2 hours. Upon cooling to room temperature, the solid was filtered through a sintered glass funnel and washed with ethanol (200 mL×3). The wet solid was dried in the vacuum oven at 85° C. for 3 days until the residual solvent met specification. 120 g of compound (2) was obtained as a white solid in a yield of 49%, with HPLC purity 99.7%.

Example 10. Activity of Analogs of Compound (1)

A number of exemplary analogs of compound (1) were prepared based on the syntheses described here. For each of these compounds, the viability of human cancer cells at 72 hours post-treatment with the compound was measured. The change in potency (relative to ONC201) was determined and is presented in the table below.

Relative Potency of Analogs of Compound (1)

| No. | Identifier | $R_1$ | $R_2$ | Relative Potency* |
|---|---|---|---|---|
| 1 | ONC201 | $CH_2Ph$ | $CH_2$-((2-$CH_3$)—Ph) | N/A |
| 14 | ONC902 | $CH_2Ph$ | $CH_2$(2-Cl—Ph) | B |
| 15 | ONC903 | $CH_2Ph$ | $CH_2$-(2-thienyl) | C |
| 16 | ONC904 | $CH_2Ph$ | $CH_2CH_2Ph$ | B |
| 17 | ONC905 | $CH_2Ph$ | $CH_2CH_2$(4-N-benzyl-piperazine) | C |
| 18 | ONC906 | $CH_2Ph$ | $CH_2$-(2,4-di F—Ph) | A |
| 19 | ONC907 | H | $CH_2$-((2-$CH_3$)—Ph) | C |
| 20 | ONC908 | $CH_3$ | $CH_2$-((2-$CH_3$)—Ph) | B |
| 21 | ONC909 | $CH_2CH_2Ph$ | $CH_2$-((2-$CH_3$)—Ph) | B |
| 32 | ONC910 | $(CH_2)_3$—NH—BOC | $CH_2$-((2-$CH_3$)—Ph) | B |
| 33 | ONC911 | $(CH_2)_3$—$NH_2$ | $CH_2$-((2-$CH_3$)—Ph) | B |
| 41 | ONC210 | $CH_2Ph$ | $CH_2$-(3,5-di F—Ph) | A |
| 51 | ONC211 | $CH_2Ph$ | $CH_2$-(3,4-di Cl—Ph) | A |
| 52 | ONC212 | $CH_2Ph$ | $CH_2$-(4-$CF_3$—Ph) | A |
| 53 | ONC213 | $CH_2Ph$ | $CH_2$-(3,4-di F—Ph) | A |
| 54 | ONC214 | $CD_2C_6D_5$ | $CH_2$-((2-$CH_3$)—Ph) | B |
| 43 | ONC217 | $CH_2Ph$ | $CH_2$(2-F—Ph) | B |
| 55 | ONC218 | $CH_2Ph$ | $CH_2$(2-$CH_3$, 4-F—Ph) | A |
| 56 | ONC219 | $CH_2Ph$ | $CH_2$-(2,4-di Cl—Ph) | A |
| 57 | ONC220 | $CH_2Ph$ | $CH_2$-((4-$OCH_3$)—Ph) | A |
| 35 | ONC222 | $CH_2Ph$ | $CH_2$-(3-isoxazolidinyl) | B |
| 36 | ONC224 | $CH_2Ph$ | $CH_2CH_2$-(4-morpholinyl) | A |

-continued

| No. | Identifier | R₁ | R₂ | Relative Potency* |
|---|---|---|---|---|
| 38 | ONC221 | H | $CH_2$-(4-$CF_3$—Ph) | A |
| 72 | ONC225 | $CH_2Ph$ | $CH_2$-(2-F, 4-$CF_3$—Ph) | A |

*Relative to the potency of ONC201; A Indicates a potency increase of >2-fold of ONC201;
B Indicates potency that is within 2-fold of ONC201; and C Indicates a potency decrease of >2-fold of ONC201.

In addition, a single dose of compound (52) by oral or intraperitoneal administration to human colon cancer xenograft-bearing mice resulted in a significant reduction of tumor volume compared to vehicle-treated control cohorts. Compound (52) has a wide therapeutic window, as it is well tolerated at doses at least up to 225 mg/kg in mice.

Example 11. Dosing Regimens

Compound (1) is administered to tumor-bearing mice, according to one of the following dosing regimens using a 7 day recurring cycle.
1) Day 1: 200 mg/kg orally;
2) Day 1/Day 4: 100 mg/kg orally per dose;
3) Day 1/Day 2: 100 mg/kg orally per dose; or
4) Day 1: 2 doses split 6 hours apart at 100 mg/kg orally per dose.

The efficacy of the dosing regimens are assessed and compared.

Example 12. Preliminary Determination of Interactions with Compound (1)

The preliminary spectrum of compound (1) in the human colon carcinoma cell line HCT116 was determined.

Briefly, compound (33) (ONC911) was immobilized at different immobilization densities to sepharose beads. For analysis by quantitative mass spectrometry, HCT116 human colon carcinoma cells were grown in media with different forms of isotopically labeled amino acids (SILAC=stable isotope labeling by amino acids in cell culture). The corresponding proteomes can be distinguished by the introduced mass difference. Binding experiments were performed in duplicate with a partial switch of labels to exclude labeling artifacts. Bound proteins were completely eluted from the affinity matrices, separated by SDS-PAGE and subjected to tryptic digestion. Recovered peptides were analyzed by LC-MS/MS on an LTQ Orbitrap Velos mass spectrometer (Thermo Fisher). Raw data generated by LC-MS/MS were processed by MaxQuant to obtain quantitative protein abundance data.

Quantified proteins were analyzed for enrichment of proteins compared to the control matrix and competition of bound protein by incubation with compound (1). Such a binding and displacement pattern would be expected of a specific target protein.

Results

First, HCT116 cells were cultivated and metabolically labeled by SILAC. Efficient SILAC encoding with incorporation rates of the isotopic variants of arginine and lysine exceeding 95% was achieved. Sufficient cells were prepared for subsequent experiments. Cell extracts were generated by detergent mediated cell lysis. In addition, remaining cell nuclei were extracted by lysis in the presence of 400 mM NaCl in order to include nuclear proteins. The cytosolic and nuclear extracts were combined.

The linker compound (33) (ONC911) was immobilized via its amino group to sepharose beads. Bead with four different immobilization densities of 6 mM, 3 mM, 1 mM and 0.3 mM were prepared. These matrices were used to enrich proteins from HCT116 extracts and to investigate displacement of bound proteins by 50 μM of compound (1).

In total, ~3600 proteins were identified. Specific enrichment of proteins by immobilized compound (33) (ONC911) was observed for all coupling densities and replicates.

The number of candidates increased with the immobilisation density. Table 3 summarizes the target candidates of compound (1). At the highest coupling density (6 mM) enrichment by the affinity matrix and consistent displacement over two replicates by compound (1) was observed for 14 proteins. At a coupling density of 3 mM two potential target candidates were identified, both of which were shared with the high coupling density. At the lower coupling densities (1 and 0.3 mM) two and one protein behaved consistently as targets, respectively.

In addition, several proteins showed enrichment by the affinity matrix and displacement by compound (1), but displacement was observed in only one of the two replicates per coupling density. Such proteins are designated as "OK (with outlier)" in Table 3.

In summary, immobilized compound (33) (ONC911) appears to be functional and is able to specifically enrich proteins from a cell lysate. Additionally, distinct competition with 50 μM of compound (1) was observed.

TABLE 3

| Uniprot ID | Protein Names | Gene Names | Target Classification 0.3 mM | Target Classification 1 mM | Target Classification 3 mM | Target Classification 6 mM |
|---|---|---|---|---|---|---|
| Q7Z739 | YTH domain-containing family protein 3 | YTHDF3 | OK (with outlier) | OK (with outlier) | OK | OK |
| P35637 | RNA-binding protein FUS | FUS | OK (with outlier) | | OK | OK |
| P52597 | Heterogenous nuclear ribonucleoprotein F | HNRNPF | | OK (with outlier) | OK (with outlier) | OK |
| Q96D17 | U5 small nuclear ribonucleoprotein 40 kDa protein | SNRNP40 | OK (with outlier) | | OK (with outlier) | OK |

TABLE 3-continued

| Uniprot ID | Protein Names | Gene Names | Target Classification 0.3 mM | Target Classification 1 mM | Target Classification 3 mM | Target Classification 6 mM |
|---|---|---|---|---|---|---|
| P08621 | U1 small nuclear ribonucleoprotein 70 kDa | SNRNP70 | | | OK (with outlier) | OK |
| Q9NZR1 | Tropomodulin-2 | TMOD2 | | | | OK |
| Q01082 | Spectrin beta chain, non-erythrocytic 1 | SPTBN1 | | | | OK |
| Q9Y5A9 | YTH domain-containing family protein 2 | YTHDF2 | | | | OK |
| Q13813 | Spectrin beta chain, non-erythrocytic 1 | SPTAN1 | | | | OK |
| A1L390 | Pleckstrin homology domain-containing family G member 3 | PLEKHG3 | | | | OK |
| P09234 | U1 small nuclear ribonucleoprotein C | SNRPC | | | | OK |
| Q86XK2 | F-box only protein 11 | FBXO11 | | | | OK |
| O15427 | Monocarboxylate transporter 4 | SLC16A3 | | | | OK |
| P09012 | U1 small nuclear ribonucleoprotein A | SNRPA | | | | OK |
| Q9Y520 | Protein PRRC2C | PRRC2C | OK (with outlier) | OK | | |
| Q9GZS1 | DNA-directed RNA polymerase I subunit RPA49 | POLR1E | | OK | | |
| P61962 | DDB1- and CUL4-associated factor 7 | DCAF7 | OK | | | |
| O43172 | U4/U6 small nuclear ribonucleoprotein Prp4 | PRPF4 | OK (with outlier) | OK (with outlier) | OK (with outlier) | OK (with outlier) |
| P62314 | Small nuclear ribonucleoprotein Sm D1 | SNRPD1 | | | OK (with outlier) | OK (with outlier) |
| Q13523 | Serine/threonine-protein kinase PRP4 homolog | PRPF4B | | | OK (with outlier) | OK (with outlier) |
| P52701 | DNA mismatch repair protein Msh6 | MSH6 | | | | OK (with outlier) |
| Q02880 | DNA topoisomerase 2-alpha | TOP2B | | | | OK (with outlier) |
| P11388 | DNA topoisomerase 2-beta | TOP2A | | | | OK (with outlier) |
| P12268 | Inosine-5-monophosphate dehydrogenase 2 | IMPDH2 | | | | OK (with outlier) |
| Q9NR56 | Muscleblind-like protein 1 | MBNL1 | | | | OK (with outlier) |
| Q9BQ67 | Glutamate-rich WD repeat-containing protein 1 | GRWD1 | | | | OK (with outlier) |
| P08579 | U2 small nuclear ribonucleoprotein B | SNRPB2 | | | | OK (with outlier) |
| Q8IVT2 | Mitotic interactor and substrate of PLK1 | MISP | | | | OK (with outlier) |
| O75940 | Survival of motor neuron-related splicing fator 30 | SMNDC1 | | | | OK (with outlier) |
| P15924 | Desmoplakin | DSP | | | | OK (with outlier) |
| Q14157 | Ubiquitin-associated protein 2-like | UBAP2L | | | | OK (with outlier) |
| O75083 | WD repear-containing protein 1 | WDR1 | | | | OK (with outlier) |
| P06737 | Glycogen phosphorylase, liver form | PYGL | | | | OK (with outlier) |

Uniprot ID: Best Uniprot identifier;
Protein name: Protein name according to Uniprot.

Target classification: Evaluation of the respective protein at the indicated coupling density of compound ONC216. "OK" indicates that the respective protein was consistently enriched and competed over 2 independent replicate experiments. "OK (with outlier)" indicates enrichment by the affinity matrix and displacement by Compound (1), but displacement was observed in only one of the two replicates.

Example 13. GPCR Antagonism of Compound (1)

ONC201 was evaluated in a whole cell, functional assay of a β-Arrestin G protein-coupled receptor (GPCR) activity that directly measure dopamine receptor activity by detecting the interaction of β-Arrestin with the activated GPCR that can serve as a reporter. For each dopamine receptor (DRD1, DRD2S, DRD2L, DRD3, DRD4, and DRD5), cell lines overexpressing the reporter constructs were expanded from freezer stocks. Cells were seeded in a total volume of 20 μL into white walled, 384-well microplates and incubated at 37° C. prior to testing. with antagonist followed by agonist challenge at the $EC_{80}$ concentration. Intermediate dilution of sample stocks was performed to generate 5× sample in assay buffer. 3.5 μL of 5× sample was added to cells and incubated at 37° C. or room temperature for 30 minutes. Vehicle concentration was 1%. 5 μL of 6×$EC_{80}$ agonist in assay buffer was added to the cells and incubated at 37° C. or room temperature for 90 or 180 minutes prior to assay readout. % Antagonism was calculated using the following formula %

Antagonism=100%×(1—(mean RLU of test sample—mean RLU of vehicle control)/(mean RLU of EC$_{80}$ control—mean RLU of vehicle control).

Example 14. Assessing Compound (1) Interactions with Efflux and Transporter Proteins The ability of ONC201 to interfere with transporter protein activity is evaluated to determine the dosing regimens for ONC201 in combination with substrates on transporter proteins. The timing or dose level of ONC201 in combination with another therapeutic agent may be modified based on these assay results. Transporter proteins include OATP1B1, OATP1B3, OAT1, OAT3, OCT1, OCT2, MATE1 and MATE2-f solute carriers (SLC).

The ability of ONC201 to interfere with the efflux proteins was evaluated to determine if ONC201 could inhibit the ability of these proteins to efflux small molecule substrates. Inhibiting these efflux proteins could increase the efficacy of efflux protein substrates by combining with ONC201 to increase its intracellular concentrations or to alter its biodistribution. Efflux proteins include MDR1 and BCRP.

The interaction of ONC201 with the human MDR1 and BCRP transporter was investigated in vitro using MDR1 and BCRP over-expressing Madin-Darby canine kidney (MDCKII-MDR1 and MDCKII-BCRP) and the parental cells (MDCKII). The bidirectional permeability of respective probe substrates in MDCKII-MDR1 and -BCRP and MDCKII monolayers was performed to investigate if ONC201 is an inhibitor for MDR1 and BCRP. Digoxin and prazosin were used as the probe substrates for MDR1 and BCRP, respectively.

The inhibition assay results are summarized in Table 4 below. ONC201 is an inhibitor of MDR1 and BCRP at 200 micromolar. The combination of ONC201 with substrates of MDR1 or BCRP may increase the efficacy of the substrate by increasing intracellular concentrations of the substrate or altering its biodistribution.

TABLE 4

| Transporter (Probe Substrate) | Inhibitor | Probe Substrate Apparent Permeability ($10^{-6}$ cm/s) in Corresponding Transporter Test System | | Efflux Ratio | % Inhibition (Efflux Ratio) |
|---|---|---|---|---|---|
| | | A-B | B-A | | |
| MDR1 (Digoxin) | None | 1.61 | 25.3 | 15.72 | 0.0 |
| | 200 µM ONC201 | 4.69 | 11.16 | 2.38 | 90.6 |
| | 10 µM Valspodar (PC) | 4.31 | 6.36 | 1.48 | 96.8 |
| BCRP (Prazosin) | None | 2.37 | 71.37 | 30.10 | 0.0 |
| | 200 µM ONC201 | 9.54 | 60.53 | 6.34 | 81.6 |
| | 1 µM Ko134 (PC) | 24.70 | 34.31 | 1.39 | 98.7 |

A-B: apical-to-basolateral;
B-A: basolateral-to-apical;
PC: positive control

Example 15. Assessing Inhibitory Potential of Compound (1) for P450 Enzymes

The potential of ONC201 to induce human cytochrome P450 (CYP) enzymes with attention to the three major inducible drug-metabolizing enzymes, i.e. CYP 1A2, 2B6, and 3A4, using cryopreserved plateable human hepatocytes was evaluated.

The experimental CYP induction results of ONC201 are summarized in Table 5 below. ONC201 did not induce P450 to an effect that was ≥20% of positive controls in this assay. Therefore can be used in combination of other drugs without changing the activity of CYP enzymes.

TABLE 5

Induction of CYP mRNA in Cyropreserved Human Hepatocytes with Various Treatments

| | | mRNA Induction Fold[a] with Different Treatments | | | | |
|---|---|---|---|---|---|---|
| CYP | Donor | ONC201 2 µM | ONC201 20 µM | ONC201 200 µM | NC[b] | PC[c] |
| 1A2 | CDP | 1.56 | 0.21 | 0.03 | 1.16 | 28.71 |
| | NHI | 2.85 | 0.50 | 0.18 | 1.31 | 35.53 |
| | EJW | 1.91 | 0.26 | 0.02 | 1.34 | 31.06 |
| 2B6 | CDP | 1.46 | 1.01 | 1.41 | 1.16 | 8.56 |
| | NHI | 3.69 | 2.56 | 1.81 | 1.37 | 14.38 |
| | EJW | 2.46 | 1.39 | 0.34 | 1.27 | 8.98 |
| 3A4 | CDP | 2.09 | 3.13 | 1.27 | 1.03 | 44.18 |
| | NHI | 3.79 | 2.91 | 0.84 | 1.37 | 62.38 |
| | EJW | 3.39 | 8.42 | 0.51 | 0.93 | 85.90 |

[a]CYP mRNA induction fold values were calculated using a standard $\Delta\Delta C_T$ method with 18S gene as the reference gene and target (CYP) gene expression of hepatocytes treated with vehicle control as the baseline.
[b]NC: Negative control - flumazenil (25 µM) was used as the negative control treatment
[c]PC: Positive control - omeprazole (50 µM), phenobarbital (750 µM) and rifampin (25 µM) were used as the positive control treatment for CYP 1A2, 2B6 and 3A4, respectively.
Data is calculated from triplicate measurements.

The inhibitory potentials of ONC201 against seven (7) human cytochrome P450s (CYP), i.e. CYP1A2, 2B6, 2C8, 2C9, 2C19, 2D6, and 3A4, were investigated in vitro in pooled human liver microsomes (HLM) using eight (8) CYP isoform specific marker substrate reactions. They were CYP1A2-mediated phenacetin 0 deethylation, CYP2B6-mediated bupropion hydroxylation, CYP2C8-mediated amodiaquine N deethylation, CYP2C9-mediated diclofenac 4' hydroxylation, CYP2C19 mediated S mephenytoin 4' hydroxylation, CYP2D6-mediated bufuralol 1' hydroxylation, CYP3A4 mediated midazolam 1' hydroxylation, and testosterone 6β hydroxylation.

ONC201 inhibited CYP isozymes (CYP 1A2, 2B6, 2C8, 2C9, 2C19, 2D6 and 3A4) with IC$_{50}$ values ranging from 34.9 to 428.6 µM (4 to 48-fold above Cmax of 9 µM; 40-480-fold above average plasma concentration at 24-hours of 0.9 µM) and the inhibition was not significantly time-dependent (See Table 6). These results indicate that ONC201 can be administered with most other drugs without safety concerns related to drug-drug interactions.

TABLE 6

| CYP | Marker Substrate (Conc.) | Isoform-Catalyzed Reaction | Direct Inhibition IC$_{50}$[a] (µM) | Time-dependent Inhibition IC$_{50}$[a] (µM) |
|---|---|---|---|---|
| 1A2 | Phenacetin (50 µM) | O-deethylation | 428.6 | >500[b] |
| 2B6 | Bupropion (50 µM) | hydroxylation | 51.3 | 97.7 |
| 2C8 | Amodiaquine (2 µM) | N-deethylation | 34.9 | 31.4 |
| 2C9 | Diclofenac (5 µM) | 4'-hydroxylation | 103.2 | 107.3 |
| 2C19 | S-mephenytoin (20 µM) | 4'-hydroxylation | 85.3 | 82.8 |
| 2D6 | Bufuralol (10 µM) | 1'-hydroxylation | 82.7 | 174.4 |

TABLE 6-continued

| CYP | Marker Substrate (Conc.) | Isoform-Catalyzed Reaction | Direct Inhibition $IC_{50}^a$ (µM) | Time-dependent Inhibition $IC_{50}^a$ (µM) |
|---|---|---|---|---|
| 3A4 | Midazolam (2.5 µM) | 1'-hydroxylation | 73.3 | 85.8 |
| 3A4 | Testosterone (50 µM) | 6β-hydroxylation | 49.3 | 24.0 |

$^a$$IC_{50}$ values for Error! Reference source not found. were determined by fitting normalized data to sigmoidal inhibitory non-linear regression model using GRAPHPAD PRISM ®.
$^b$>500 - no inhibition >50% within the concentration range tested (1.5-500 µM).

Example 16. Human Clinical Trial of Oral ONC201 in Patients with Refractory Solid Tumors ONC201 induces apoptosis in tumor, but not normal, cells at doses that trigger high levels of cell death in human cancer cells. The safety profile of ONC201 in GLP safety studies in rats and dogs was consistent with the preferential cytotoxicity of ONC201 in tumor over normal cells in vitro. Thus the in vitro and in vivo profiles of ONC201 indicate a wide therapeutic window that is highly desirable for cancer therapeutics. A schedule of every 21 days was selected for the clinical studies based on preclinical results that indicate sustained PD in tumors and after initial preliminary experiments suggesting that more frequent dosing did not appear to substantially increase the in vivo efficacy.

Based on the compelling efficacy and safety profile of ONC201, as well as the novel engagement of signaling pathways that are important for many cancers, the clinical introduction of ONC201 in patients with advanced cancers was undertaken. The primary objective of this first-in-human, phase I dose-escalation study was to determine the recommended phase II dose (RP2D) of ONC201 administered orally in patients with advanced cancers, as well as to evaluate the safety and tolerability of the drug. Secondary objectives included assessments of pharmacokinetics, pharmacodynamics and preliminary anti-tumor activity of ONC201.

Briefly, this phase I, open-label study treated 10 patients during dose escalation with histologically-confirmed advanced solid tumors. An additional 10 patients have been accrued in an ongoing expansion phase to increase the safety experience. Patients received ONC201 orally every 3 weeks at doses from 125 to 625 mg using an accelerated titration design.

The RP2D was defined as 625 mg that achieved a $C_{max}$ of 1.5-7.5 mg/mL (~3.9-19.4 mM). Plasma concentrations saturated at 375 mg, suggesting dose escalation above 625 mg was not warranted. No Grade >1 drug-related adverse events occurred. During the dose escalation phase, the mean number of cycles (21 days) was 3.1. The expansion phase with 10 patients confirmed the safety of ONC201 at the RP2D. PK analysis revealed a half-life of 9.6 hours and an AUC of 25 h·µg/L. Prolonged induction of serum caspase-cleaved keratin 18 and induction of TRAIL was observed. Eight of 10 patients had stable disease and one patient with prostate adenocarcinoma experienced prolonged stable disease, remaining on study for 27 weeks. One additional patient with endometrial cancer underwent a mixed response.

ONC201 is extremely well tolerated, possesses a favorable PK profile with saturable absorption of micromolar plasma concentrations, and exhibits signs of clinical activity when orally administered at 625 mg every 3 weeks.

Patients and Methods
Ethics

The study was carried at the Robert Wood Johnson University Hospital/Rutgers Cancer Institute of New Jersey (CINJ) in accordance with the Declaration of Helsinki and the International Conference on Harmonization Good Clinical Practice Guidelines and was approved by relevant regulatory committees and the Institutional Review Board of CINJ. Patients provided written, informed consent for their study participation.

Patient Population

Patients of 18 years of age or older with advanced solid tumors who had no standard treatment or were resistant to standard treatments, ECOG performance status of ≥1, and assessable disease by RECIST 1.1 criteria were eligible. If patients had received radiation therapy, they had to have one measurable lesion outside the irradiated area. Patients had to have finished all prior cytotoxic chemotherapy at least 4 weeks, alkylating agents at least 6 weeks, molecularly targeted agents at least 28 days, and radiotherapy at least 14 days prior to the first dose. All prior treatment related adverse events Grade ≤2 except alopecia and neuropathy had to have been resolved. Patients had to have exhibited normal marrow and organ function as defined by the following parameters: absolute neutrophil count ≥1,500/mcL; platelets ≥100,000/mcL; hemoglobin ≥9.0 mg/dL without transfusion in 2 prior weeks; total bilirubin within normal range (for patients with liver metastases, serum bilirubin ≤1.5×ULN); AST (SGOT)/ALT (SGPT)≤2.5×upper limit of normal; and measured or estimated creatinine clearance ≥40 mL/min/1.73 m$^2$ for patients with creatinine levels above normal. Exclusion criteria included symptomatic brain metastases or asymptomatic brain metastases treated with steroids, prior bevacizumab treatment, prior allergic reactions to compounds similar to ONC201, uncontrolled intercurrent illnesses, combination retroviral therapy for HIV, active cardiac disease/history of cardiac dysfunction, stroke or seizures in the last 3 months, impairment of GI function that may alter absorption of ONC201, pregnancy and treatment with hematopoietic colony-stimulating growth factor ≤2 weeks prior to beginning treatment.

Study Design and Toxicity Assessment

The design was an open-label, dose-escalation phase I trial of monoagent ONC201 in patients with advanced, refractory tumors who had exhausted or refused standard treatment options for their respective indications. Capsules (125 mg) of ONC201 were provided by Oncoceutics Inc (Philadelphia, Pa.). ONC201 was administered orally once every 21-day cycle using an accelerated dose escalation design. The oral starting dose was 125 mg (10% of no-observed-adverse-event-level in rats and dogs). The study was conducted with a single patient accelerated dose escalation design that was designed to stop if any patient experienced a Grade ≥2 adverse event that was at least possibly related to ONC201. In this case a traditional 3+3 dose escalation design would have been used. Dose escalation could proceed after the previously dosed cohort completed one treatment cycle and met the criteria to proceed with the next dose level. Enrollment at each subsequent dose level required that all patients enrolled at the prior dose level completed Cycle 1 dosing and were evaluated 21 days later to assess safety. Dose levels proceeded from 125 mg to 250 mg, 375 mg, 500 mg and finally to 625 mg.

Following determination of the RP2D, an expansion phase of up to 22 patients was initiated to enroll additional patients at the RP2D to increase the robustness of the safety data generated by the trial.

All toxicities were evaluated based on the Common Terminology Criteria for Adverse Events version 4. DLT was defined as a drug-related adverse event or abnormal laboratory result that occurred in the first cycle of treatment that met any of the following criteria: ≥Grade 3 non-hematological toxicity; ≥Grade 3 nausea, vomiting, or diarrhea that has persisted for ≥72 hours despite optimal anti-emetic or antidiarrheal therapy; Grade 3-4 AST/ALT in combination with a Grade 2 elevation in bilirubin; Grade 4 neutropenia lasting =7 days; Grade 4 neutropenia and fever of >38.5° C.; Grade 3 neutropenia with >Grade 3 infection; thrombocytopenia of any grade if associated with clinically significant bleeding; Grade 4 thrombocytopenia; or Grade 4 anemia and was assessed as unrelated to disease, disease progression, inter-current illness, or concomitant medications; and is determined by the investigator to be "possibly related", "probably related" or "definitely related" to the administration of ONC201.

Safety Assessments

Safety assessments including complete blood count, serum chemistry, and toxicity were evaluated at baseline, followed by weekly during the first 2 cycles, and then every 3 weeks afterward. Electrocardiograph monitoring was carried out just before ONC201 administration, followed by 15 minutes, 1 hour and 2 hours, after drug administration. Adverse events were graded using the CTCAE version 4.0. Tumor responses were assessed using RECIST every 2 cycles.

Pharmacokinetic Analyses

Plasma samples for PK were collected at baseline, 30 minutes, 2 hours, 4 hours, 6 hours, 24 hours, 48 hours, and 168 hours following the first dose of ONC201 and before doses prior to treatment in cycles 2-6. PK was analyzed by LC-MS/MS using a validated GLP method to detect ONC201 in human plasma. PK analysis was performed using PHOENIX® WINNONLIN® Version 6.3 (PHARSIGHT®, St. Louis, Mo.).

Statistical Analysis

Descriptive statistics were used for the analysis of safety and tumor response data.

Pharmacodynamic Analyses

Blood samples for PD were collected at 6 hours, days 2, 3, 8, and 15 after ONC201 treatment for cycle 1, and pre-dose on the day of drug administration for cycle 2 and 3. Serum levels of cleaved cytokeratin 18 (cCK18) were assessed using the M30 assay and serum levels of total cytokeratin 18 (CK18) were assessed using the M65 assay (Perviva A. B., Sweden). Assessments of other tumor-specific markers were also evaluated per standard of care.

Tumor Type In Vitro Sensitivity

The in vitro activity of ONC201 was evaluated in 1020 genetically annotated cell lines that from the Genomic of Drug Sensitivity in Cancer (http://www.cancerrxgene.org) collection. $IC_{50}$ values were determined by cell viability assays at 72 hours post-treatment as reported previously. The estimated $IC_{50}$ values were averaged across multiple cell lines for each tumor type. Tumor types were categorized into three different groups that represented tertiles of average $IC_{50}$ values. These groups are referred to as "high", "low" and "medium" in Table 11 based on their tertile classification within the ONC201 sensitivity spectrum.

Results

Patient Characteristics

During the dose escalation phase, 10 evaluable patients were enrolled in this study. Patient characteristics are listed in Table 7. Following the completion of the dose escalation phase, an additional 10 patients were enrolled in an ongoing expansion phase (Table 8).

TABLE 7

Patient demographics and safety experience with ONC201 administered every three weeks in dose escalation phase.

| Pat # | Tumor Type | Age (years) | Sex | Weight (Kg) | ONC201 (mg) | Adverse Events Grade 1 | Grade 2-4 |
|---|---|---|---|---|---|---|---|
| 1 | NSCLC | 80 | F | 47.3 | 125 | Fever (Possibly-related) | 0 |
| 2 | Appendiceal adenocarcinoma | 47 | M | 77.8 | 250 | 0 | 0 |
| 3 | Uterine cancer | 72 | F | 48 | 375 | 0 | 0 |
| 4 | Renal cancer | 62 | M | 123 | 500 | 0 | 0 |
| 5 | Breast cancer | 55 | F | 87 | 625 | 0 | 0 |
| 6 | Prostate adenocarcinoma | 69 | M | 92.4 | 625 | 0 | 0 |
| 7 | Small cell lung cancer | 70 | M | 55 | 625 | 0 | 0 |
| 8 | Colon adenocarcinoma | 71 | M | 73.5 | 625 | 0 | 0 |
| 9 | Spindle cell sarcoma | 74 | F | 95.2 | 625 | 0 | 0 |
| 10 | Ovarian | 68 | F | 61 | 625 | 0 | 0 |
| | Median | 69.5 | | 75.7 | | | |

TABLE 8

Patient demographics and safety experience in the expansion phase with ONC201 RP2D (625 mg every three weeks).

| Pat # | Tumor Type | Age (years) | Sex | Weight (Kg) | No. of Doses | Adverse Events Grade 1 | Grade 2-4 |
|---|---|---|---|---|---|---|---|
| 11 | Uterine cancer | 67 | F | 72.7 | 5* | 0 | 0 |
| 12 | Uterine cancer | 56 | F | 47.7 | 5* | 0 | |
| 13 | Ovarian cancer | 64 | F | 49.3 | 2 | Vomiting (possibly related) | 0 |
| 14 | Gall bladder cancer | 75 | F | 60.6 | 4* | 0 | 0 |
| 15 | Desmoplastic small round cell tumor (DSRCT) | 26 | M | 49.3 | 2 | 0 | 0 |
| 16 | Colon cancer | 48 | M | 84.5 | 2 | 0 | 0 |
| 17 | Prostate adenocarcinoma | 69 | M | 82.2 | 3* | 0 | 0 |
| 18 | Ovarian cancer | 56 | F | 62.7 | 2 | 0 | 0 |
| 19 | Prostate adenocarcinoma | 67 | M | 118.2 | 3* | 0 | 0 |
| 20 | Uterine Cancer | 60 | F | 82.7 | 2* | 0 | 0 |
| | Median | 62 | | 67.7 | 3 | | |

*Indicates patient remains on study.

Dose Escalation Method, Determination of RP2D and Safety

Dose cohorts are listed in Table 9. 625 mg was the highest dose reached and was determined to be the RP2D. The only adverse event during the dose escalation phase that was possibly attributed to ONC201 was a low grade fever in one patient. One patient enrolled in the top dose cohort was replaced due to rapid disease progression in cycle 1.

The only adverse event among the 10 patients enrolled in the expansion phase that was possibly attributed to ONC201 was vomiting in one patient. Both of these adverse events were Grade 1 and reversed rapidly. Laboratory studies and physical exams did not reveal any drug-related abnormalities. Similarly, cardiovascular assessments revealed no drug-related effects.

TABLE 9

Dose-escalation and expansion cohorts with ONC201 dosed every 3 weeks.

| Cohort | Dose of ONC201 (mg) | Number of Patients |
|---|---|---|
| 1 | 125 | 1 |
| 2 | 250 | 1 |
| 3 | 375 | 1 |
| 4 | 500 | 1 |
| 5 | 625 | 6 |
| Expansion | 625 | 10 |
| Total | | 20 |

Pharmacokinetics

Figure 5A:
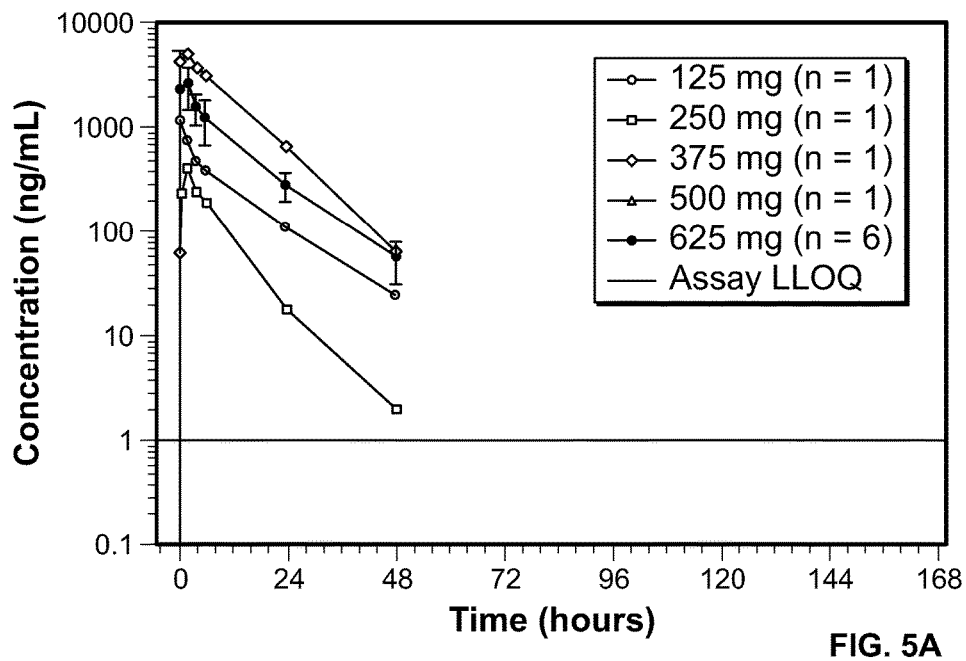
FIGS. 5A-5B shows the mean ONC201 plasma concentrations versus time following the first dose of ONC201. Concentrations are shown as (A) the mean for each dose cohort, or (B) for individuals treated at 625 mg. Error bars indicate standard deviation.
Figure 5B:
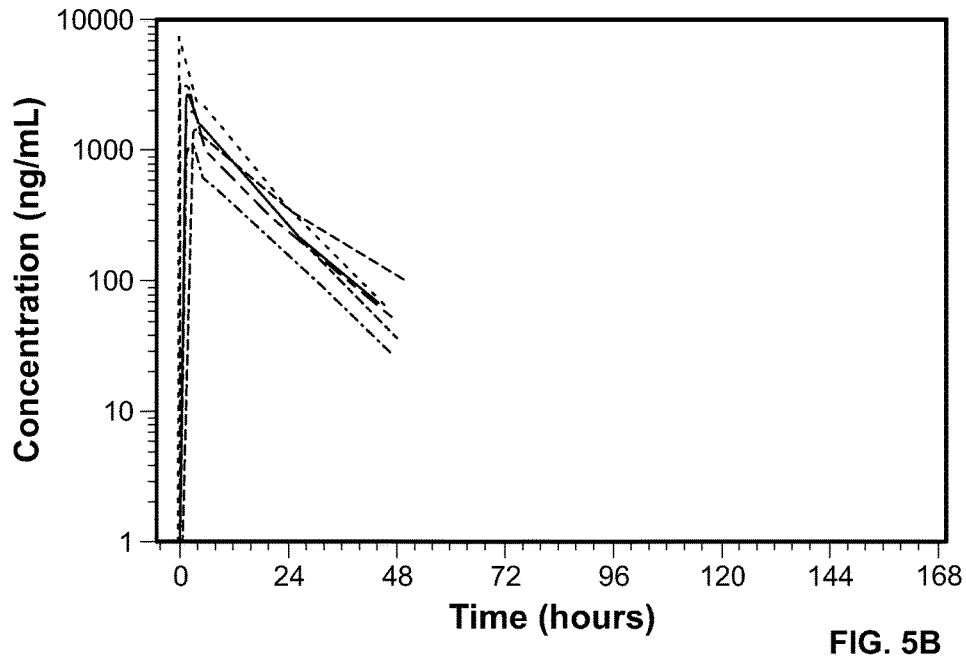
Figure 6A:
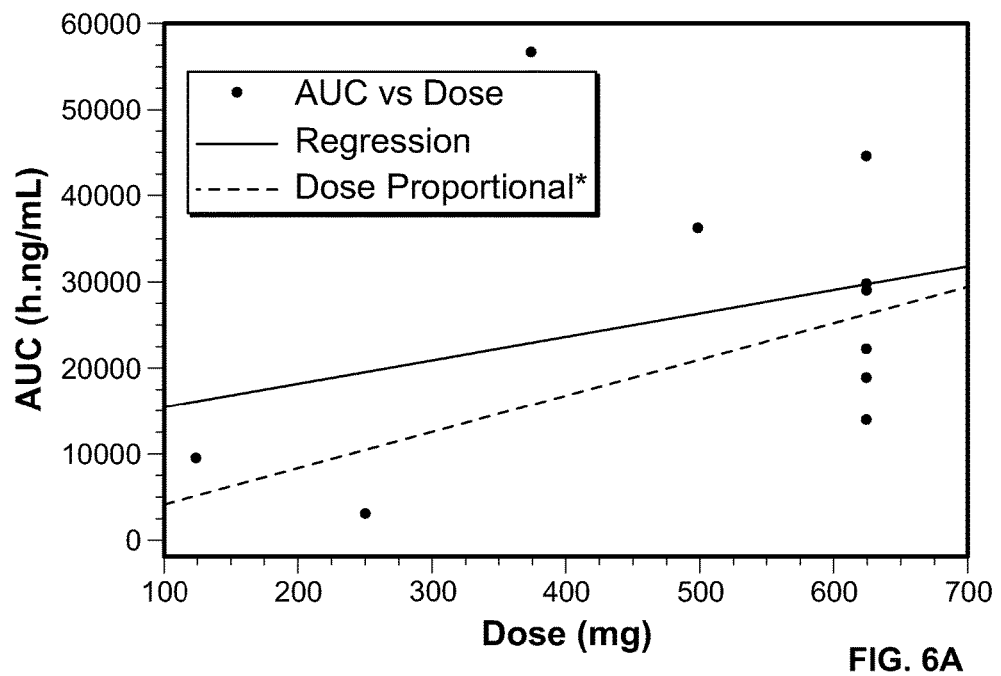
FIGS. 6A-6B illustrates individual measurements of ONC201 (A) AUC and (B) Cmax versus dose. *Anticipated dose proportionality line based on men for 625 mg dose group.
Figure 6B:
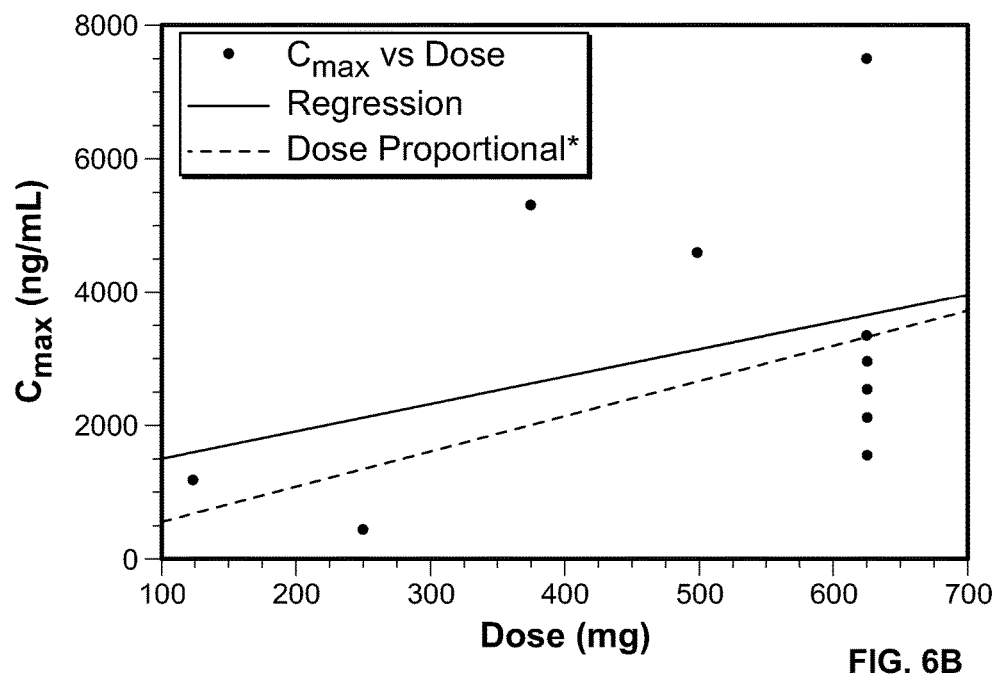

Plasma collected at serial time points was used to analyze the systemic exposure levels of ONC201 in patients (FIG. 5). PK parameters were determined for all patients and summarized for the top-dose cohort (Table 10). While dose escalation involved single patient cohorts, systemic exposure to ONC201, as determined by AUC and $C_{max}$, appeared to saturate at a dose of 375 mg (FIG. 6). For the top dose cohort, the mean $C_{max}$ was 3312 (SD 2133) ng/mL, which occurred on average 1.8 hours following administration. The mean $V_z$ was 381 (SD 164) L, consistent with a large distributive volume. Mean AUC was 26.3 (SD 10.8) h·µg/mL, and mean CL/F was 27.19 (SD 10.95) L/h. The mean $t_{1/2}$ was 9.62 (SD 1.76) hours.

TABLE 10

Mean ONC201 pharmacokinetic parameters determined in patients receiving 625 mg ONC201 every three weeks.

| | $C_{max}$ (ng/mL) | $T_{max}$ (h) | $T_{lag}$ (h) | $AUC_{last}$ (h·ng/L) | $\lambda_z$ ($h^{-1}$) | $t_{1/2}$ (h) | AUC (h·ng/m) | $V_z/F$ (L) | CL/F (L/h) |
|---|---|---|---|---|---|---|---|---|---|
| N | 6 | 6 | 6 | 6 | 6 | 6 | 6 | 6 | 6 |
| Mean | 3312 | 1.79 | 0.05 | 25515 | 0.074 | 9.62 | 26344 | 381 | 27.19 |
| SD | 2133 | 1.30 | 0.12 | 10677 | 0.013 | 1.76 | 10763 | 164 | 10.95 |
| Min | 1530 | 0.37 | 0.00 | 13490 | 0.055 | 7.71 | 13868 | 156 | 14.03 |
| Median | 2725 | 1.91 | 0.00 | 24265 | 0.072 | 9.60 | 25620 | 404 | 24.83 |
| Max | 7470 | 3.95 | 0.30 | 43830 | 0.090 | 12.55 | 44555 | 616 | 45.07 |
| CV % | 64.4 | 72.4 | 244.9 | 41.8 | 17.4 | 18.3 | 40.9 | 42.9 | 40.3 |
| Geo. Mean | 2894 | 1.34 | — | 23777 | 0.073 | 9.49 | 24601 | 348 | 25.41 |
| Geo. CV % | 58.0 | 113.5 | — | 42.9 | 18.0 | 18.0 | 42.4 | 52.9 | 42.4 |

Generally, CL/F was observed to be variable but consistent across all the dose groups. There were no apparent relationships between drug CL/F and patient sex and age. Noticeable, shallow trends were observed with patient weight and BSA. An overall increase in CL/F was observed as weight and BSA increased. Although a slight upward trend was observed, there was no strong correlation between CL/F and $CL_{CR}$.

Stronger correlations were observed with the distributive volume estimate ($V_Z$) and patient weight and BSA. A pronounced increase in $V_Z$ was observed with increasing patient weight. A greater than 2-fold increase in $V_Z$ is predicted from this trend with an increase in weight from 50 to 100 kg. A similar trend was observed between Vz and BSA. The effect of patient weight was further explored on dose-normalized exposure parameters. Trends of decreasing exposure with increasing weight were observed in plots of $C_{max}$/Dose and AUC/Dose versus patient weight. Weight normalized CL/F was plotted versus Dose, showing a similar trend to un-normalized CL/F, but with significantly less variability across patients in the 625 mg dose group.

Patient Responses

Table 11 lists patient outcomes for the 10 evaluable patients enrolled in the dose escalation phase. Out of 10 evaluable patients completed at least 2 cycles, 4 patients completed at least 4 cycles, and 1 patient received 8 cycles and remains on therapy. On average, patients received 3.1 doses of ONC201. Among the 10 patients enrolled in the expansion phase, 6 patients remain on therapy.

Pharmacodynamics

Given the heterogeneity of the tumor types in the enrolled patients, no widely used biomarker was available to uniformly assay all patient samples. In particular, the serum M30 assay is able to detect a caspase-cleaved form of cytokeratin-18 that occurs during apoptosis, which is useful in a heterogeneous study of solid tumors because most solid tumors express cytokeratin-18. The M30 sandwich ELISA has been used extensively in clinical trials as biomarkers of cell death induced by a variety of different cancer chemotherapeutic agents in a spectrum of different solid tumors. In addition to the serum M30 assay, the M65 sandwich ELISA assay, which has also been used in clinical studies to detect increases in total cytokeratin 18 that can occur with tumor necrosis and disease progression, was used to differentiate tumor apoptosis from necrosis.

Figure 7A:
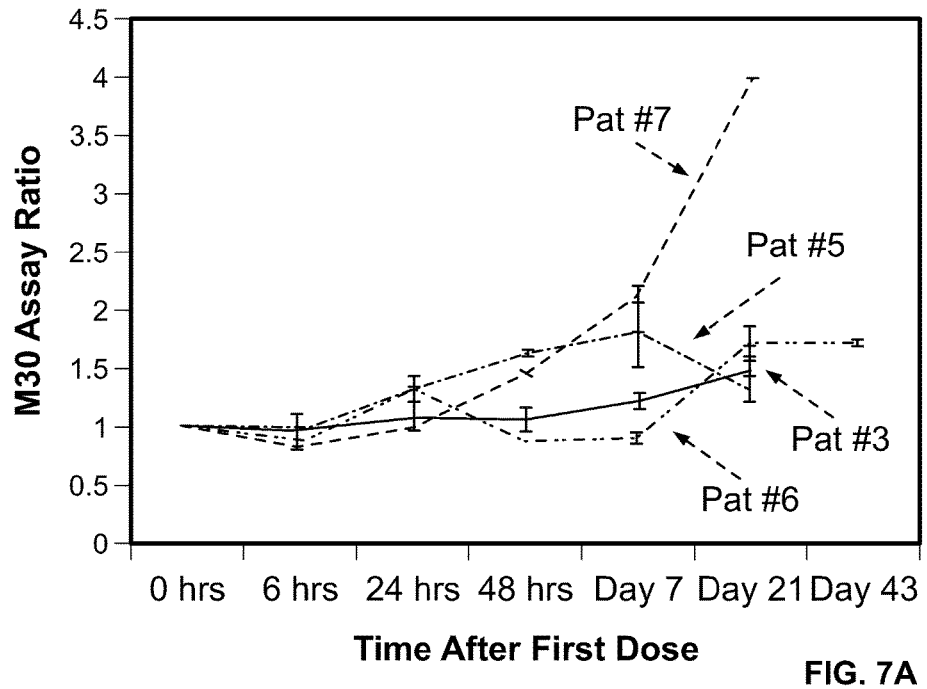
FIGS. 7A-7B shows the M30 Assay Ratio (A) versus the time after the first dose for four patients and (B) versus tumor type.
Figure 7B:
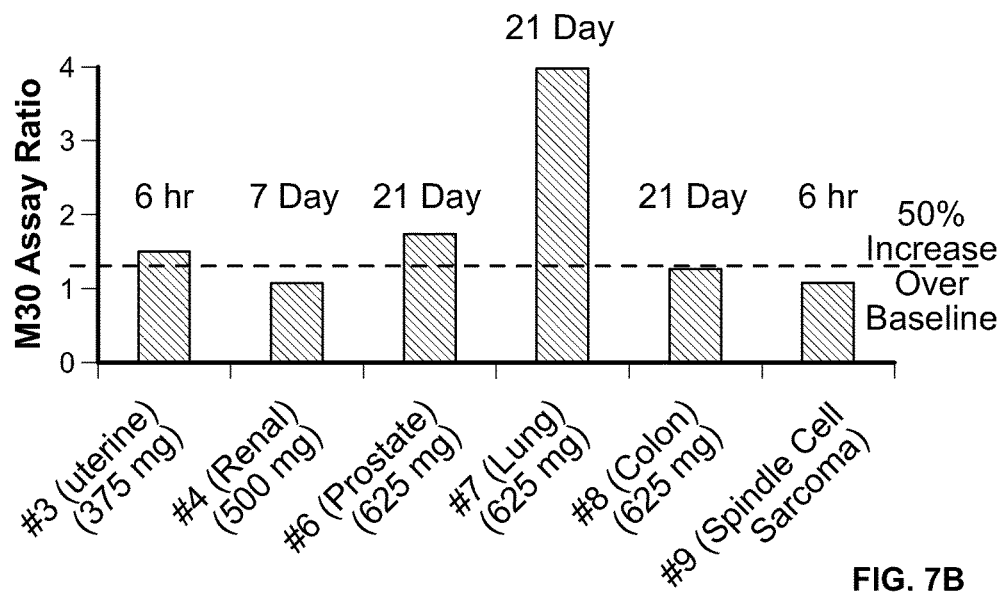
Figure 8:
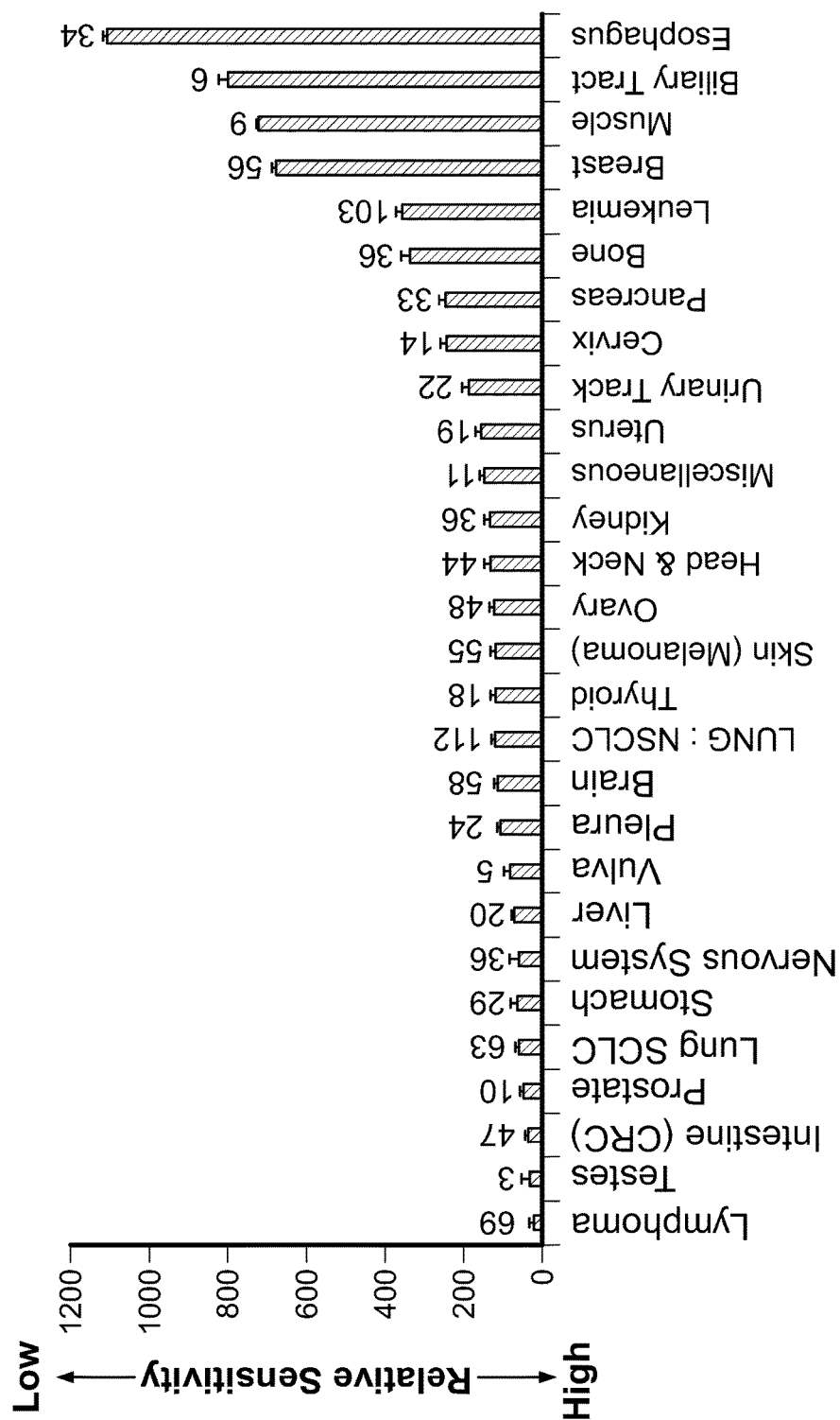
FIG. 8 illustrates the in vitro sensitivity to ONC201 for various tumor types as determined in a large collection of cell lines from the Genomic of Drug Sensitivity in Cancer program (GDSC).

As expected, the patient with rapid clinical progression who was on study for one cycle exhibited increases in the M65, but not in the M30 assay. In contrast, the patient who has remained on study through 8 cycles exhibited increases in the M30, but not in the M65, assay. Four of the patients enrolled in the dose escalation phase of the study had an induction in the M30 assay after a single dose of ONC201, most often on day 21 post-treatment (FIG. 7). To attempt to further understand the relevance of the observed the heterogeneous M30 induction, the in vitro sensitivity of the tumor types determined in a large collection of cell lines from the Genomic of Drug Sensitivity in Cancer program (GDSC) was compared with those of the study patients (FIG. 8). Interestingly these patients who experienced induction in

TABLE 11

Clinical responses and pharmacodynamic in the dose escalation phase.

| Pat # | Tumor Type | ONC201 Strength (mg) | No. of doses | Best Overall response* | Time on Study (weeks) | M30 Induction (>50%) | Tumor Type In Vitro Sensitivity |
|---|---|---|---|---|---|---|---|
| 1 | NSCLC | 125 | 4 | SD | 12 | No | Med |
| 2 | Appendiceal cancer | 250 | 4 | SD | 12 | No | N/A |
| 3 | Uterine cancer | 375 | 2 | MR | 6 | Yes | Med |
| 4 | Renal cancer | 500 | 2 | SD | 6 | No | Med |
| 5 | Breast cancer | 625 | 2 | SD | 6 | Yes | Low |
| 6 | Prostate adenocarcinoma | 625 | 9 | SD | 27 | Yes | High |
| 7 | Small cell lung cancer | 625 | 2 | SD | 6 | Yes | High |
| 8 | Colon adenocarcinoma | 625 | 4 | SD | 12 | Yes | High |
| 9 | Spindle cell sarcoma | 625 | 2 | SD | 6 | No | Low |
| 10 | Ovarian | 625 | 1 | PD | 3 | No | Med |

*MR—mixed response, SD—stable disease, PD—Progressive disease. Tumor type in vitro sensitivity categorization is described in the methods section.

Clinical and laboratory results indicated that the drug possessed biological activity in the treated patients. Patient #3, a 72 year old patient with advanced clear cell endometrial cancer had a mixed response with multiple nodes decreasing by >30% along with the development of new nodes. Patient #4, a 62-year-old male with renal cancer and bone metastasis with debilitating pain in the clavicle experienced relief from his clavicular pain. Patient #6, a 69-year-old patient with prostate adenocarcinoma experienced prolonged stable disease and was on study for 27 weeks. Patient #8, a 71-year old colon cancer patient had stable disease for 12 weeks with 4 doses of ONC201.

M30 were also the 3 patients with tumor types that exhibited high in vitro sensitivity to ONC201 (Table 11).

Given the downstream induction of TRAIL by ONC201 in preclinical models, serum TRAIL levels were also quantified using ELISA assays. Half of the patients exhibited a modest (~20%) increase in serum TRAIL that mostly peaked within the first 24 hours of drug administration.

Discussion

This Example is the first study of ONC201, an investigational cancer therapy, in humans. The primary objective of the study was to determine the RP2D of oral ONC201 administered every 3 weeks to patients with solid tumors who have exhausted all treatment options. As anticipated by the benign preclinical safety profile of ONC201, no drug-related >grade 1 toxicities were observed at micromolar plasma concentrations that are effective in preclinical models in any patient. Due to the excellent safety profile of the drug, the study allowed progression to the next dose levels without requiring additional patient enrollments and was completed without digressing from the accelerated titration design. This study determined 625 mg administered once every 3 weeks as the RP2D on the absence of toxicity and the fact that this dose achieves therapeutic plasma concentration. This RP2D exceeds the saturation threshold observed at 375 mg and thus does not require adjustment for body-surface-area area to consistently achievable target blood levels. The RP2D has been confirmed in an expansion phase with an additional 10 patients evaluable for safety.

The pharmacokinetic profile of ONC201 indicates significant absorption of the drug with oral administration that was rapid, as indicated by the 1.8 hour mean. Importantly, the PK parameters such as $C_{max}$ and AUC in the top dose cohort treated at the RP2D exceeded those associated with the NOAEL in GLP toxicology studies. The observation that systemic exposure to ONC201 saturated at 2 dose levels below the RP2D is suggestive of saturation of absorption. Since saturation of absorption occurs at a dose that yields therapeutic plasma concentrations that are apparently well tolerated, this may function as a safety feature. These observations support the decision to discontinue further dose escalation of ONC201 beyond the RP2D while providing a safety margin around the target dose.

Given that the primary endpoint of the study was based on clinical safety in a group of highly heterogeneous patients with aggressive cancers, it is noteworthy that some patients showed some evidence of clinical benefit. These included a patient with treatment-resistant clear cell endometrial cancer who had a mixed response, 2 patients who had alleviation of symptoms associated with sites of tumor manifestation, and 2 patients (adenocarcinomas of prostate and colon) with stable disease for >2 months. In this clinical trial, treatment was terminated following disease progression using RECIST criteria, which stipulates a 20% increase in tumor size. The signs of anti-tumor activity and absence of any meaningful side effects in this trial indicate that ONC201 may offer clinical benefit without imposing the typical toxicities that anticancer therapies impose on patients.

Similar to preclinical findings, PD measurements with the M30 assay revealed that the effects of ONC201 were sustained over time in several patients. Serum TRAIL induction was noted in 2 patients; however, this assay was limited to the detection of serum soluble TRAIL as biopsies were not available. The ONC201 PK profile together with its sustained PD effects yields an opportunity for combination regimens with staggered administration that minimizes drug-drug interaction risks while maintaining synergistic biological activity. Synergistic interactions between ONC201 and approved cancer therapies have been identified with taxanes, bevacizumab, bortezomib, and sorafenib.

In conclusion, we have shown that ONC201 is very well tolerated at the RP2D of 625 mg and exhibits signs of biological activity in patients with advanced solid tumors.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

All references, including publications, patent applications, and patents, cited herein are hereby incorporated by reference to the same extent as if each reference were individually and specifically indicated to be incorporated by reference and were set forth in its entirety herein.

What is claimed is:

1. A compound having formula (10)

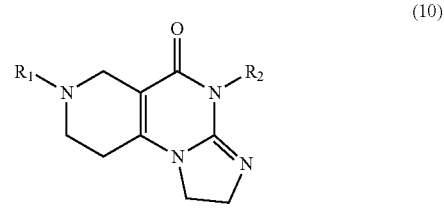

or a pharmaceutically acceptable salt thereof;
wherein $R_1$ and $R_2$ are independently selected from the group consisting of H, $C_{1-4}$alkyl, $C_{1-4}$alkylphenyl, $C_{1-4}$alkylphenylketone, $C_{1-4}$benzyl-piperazine, $C_{1-4}$alkylthienyl, $C_{1-4}$alkylpyridinyl, $C_{1-4}$alkylisoxazolidinyl, $C_{1-4}$alkylmorpholinyl, $C_{1-4}$alkylthiazolyl, and $C_{1-4}$alkylpyrazinyl wherein $C_{1-4}$alkyl, $C_{1-4}$alkylphenyl, $C_{1-4}$ alkylphenylketone, $C_{1-4}$benzyl-piperazine, $C_{1-4}$alkylthienyl, $C_{1-4}$alkylpyridinyl, $C_{1-4}$alkylisoxazolidinyl, $C_{1-4}$alkylmorpholinyl, $C_{1-4}$alkylthiazolyl, and $C_{1-4}$alkylpyrazinyl are optionally substituted with $C_{1-4}$alkyl, $C_{1-4}$alkoxyl, hydroxyl, perhalogenated $C_{1-4}$alkyl, or halogen, and
wherein $R_2$ is a substituted or an unsubstituted heteroarylalkyl.

2. A compound having formula (40)

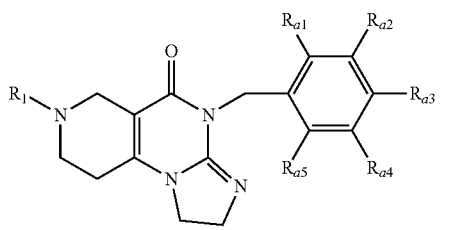

or a pharmaceutically acceptable salt thereof;
wherein $R_1$ is a hydrogen; and
wherein $R_{a1}$, $R_{a2}$, $R_{a3}$, $R_{a4}$, and $R_{a5}$ are each independently selected from the group consisting of hydrogen, X, —$CH_3$, —$NO_2$, —$OCH_3$, —CN, —$CXH_2$, —$CX_2H$, $C_2$-$C_4$ alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR'''$, $SR'''$, $NR'''R''$, $NR'''C(O)R''$, $SOR'''$, $SO_2R'''$, $C(O)R'''$, and $C(O)OR'''$;
where $R'''$ and $R''$ are independently selected from hydrogen or a $C_1$-$C_4$ alkyl;
p is an integer from 2 to 20; and
X represents a halogen.

3. A compound having formula (40)

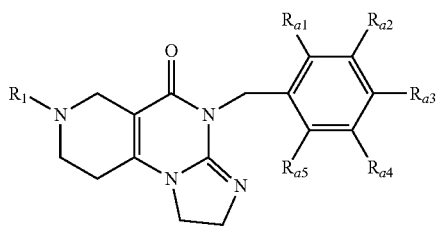

or a pharmaceutically acceptable salt thereof;
wherein $R_{a3}$ is fluorine; and
wherein $R_{a1}$, $R_{a2}$, $R_{a4}$, and $R_{a5}$ are each independently selected from the group consisting of hydrogen, X, —$CH_3$, —$NO_2$, —$OCH_3$, —CN, —$CXH_2$, —$CX_2H$, $C_2$-$C_4$ alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR'''$, $SR'''$, $NR'''R''$, $NR'''C(O)R''$, $SOR'''$, $SO_2R'''$, $C(O)R'''$, and $C(O)OR'''$;
where $R'''$ and $R''$ are independently selected from hydrogen or a $C_1$-$C_4$ alkyl;
p is an integer from 2 to 20; and
X represents a halogen.

4. A compound having formula (50)

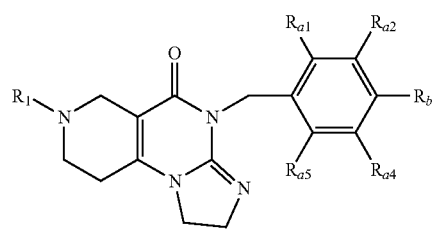

or a pharmaceutically acceptable salt thereof; wherein
$R_1$ is a hydrogen; and
$R_b$ is selected from the group consisting of X, —$CH_3$, —$NO_2$, —$OCH_3$, —CN, —$CXH_2$, —$CX_2H$, $C_2$-$C_4$ alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR'''$, $SR'''$, $NR'''R''$, $NR'''C(O)R''$, $SOR'''$, $SO_2R'''$, $C(O)R'''$, and $C(O)OR'''$;
$R_{a1}$, $R_{a2}$, $R_{a4}$, and $R_{a5}$ are each independently selected from the group consisting of hydrogen, X, —$CH_3$, —$NO_2$, —$OCH_3$, —CN, —$CXH_2$, —$CX_2H$, $C2$-$C4$ alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR'''$, $SR'''$, $NR'''R''$, $NR'''C(O)R''$, $SOR'''$, $SO_2R'''$, $C(O)R'''$, and $C(O)OR'''$;
where $R'''$ and $R''$ are independently selected from hydrogen or a $C_1$-$C_4$ alkyl;
p is an integer from 2 to 20;
and X represents a halogen.

5. A compound having the following structure:

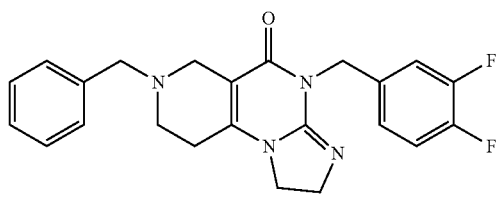 [SMILES: O=C1C2=C(CCN(Cc3ccccc3)C2)N2CCN=C2N1Cc1ccc(F)c(F)c1]

or a pharmaceutically acceptable salt thereof.

6. A compound having formula (45)

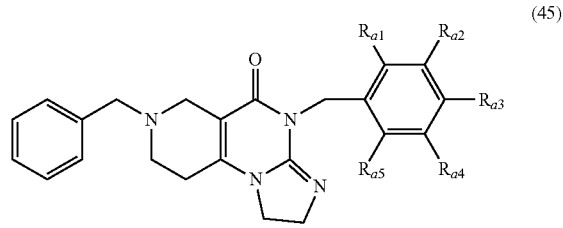

or a pharmaceutically acceptable salt thereof; wherein
$R_{a1}$, $R_{a4}$, $R_{a5}$, are each hydrogen; and $R_{a2}$ and $R_{a1}$ are each chlorine.

7. A compound having formula (45)

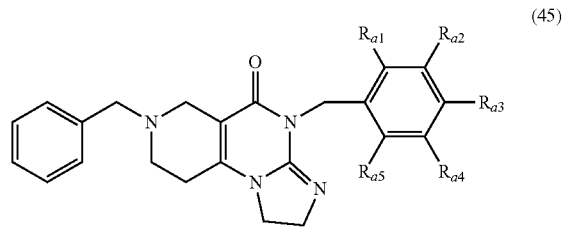

or a pharmaceutically acceptable salt thereof; wherein
$R_{a1}$, $R_{a3}$, and $R_{a5}$ are each hydrogen; and wherein $R_{a2}$ and $R_{a4}$ are fluorine.

8. A compound having formula (45)

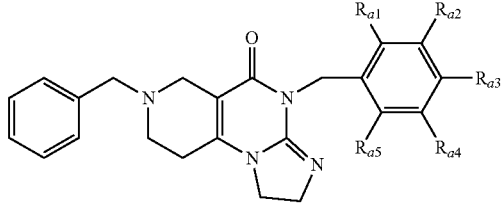

or a pharmaceutically acceptable salt thereof; wherein $R_{a2}$, $R_{a4}$, $R_{a5}$, are each hydrogen; and wherein $R_{a1}$ and $R_{a3}$ are Cl.

9. A compound having formula (45)

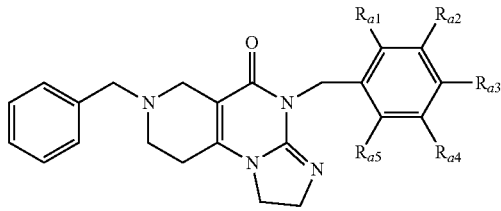

or a pharmaceutically acceptable salt thereof; wherein $R_{a2}$, $R_{a4}$, $R_{a5}$, are each hydrogen; and wherein $R_{a1}$ is a methyl and $R_{a3}$ is a fluorine.

10. A compound having formula (45)

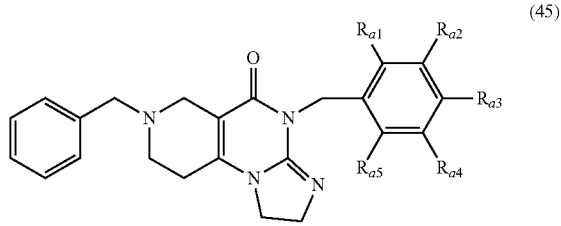

or a pharmaceutically acceptable salt thereof; wherein $R_{a2}$, $R_{a4}$, $R_{a5}$, are each hydrogen; and wherein $R_{a1}$ is a fluorine and $R_{a3}$ is a $CF_3$.

11. A compound having formula (60)

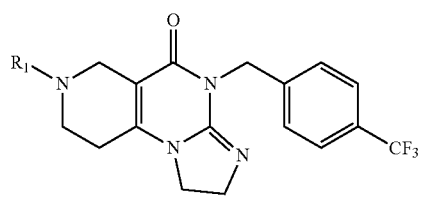

or a pharmaceutically acceptable salt thereof, wherein $R_1$ is selected from H, $CH_2$-(4-$CF_3$-Ph), $CH_2$-(4-F-Ph), $CH_2$—($OCH_3$-Ph), (4-F-Ph)-4-oxobutyl, $CH_2$-3-pyridyl, $CH_2$-4-methyl-2-thiazolyl, $CH_2$-2-pyrazinyl and $CH_2$-(3,4-di Cl-Ph).

12. A pharmaceutical composition comprising the compound according to claim 5 or a pharmaceutically acceptable salt thereof, and a pharmaceutically acceptable carrier.

13. A composition comprising a salt of the compound of claim 5.

14. The composition according to claim 13, wherein the salt is a di-salt.

15. The composition according to claim 14, wherein the di-salt is a hydrochloride di-salt.

* * * * *